US005874283A

United States Patent [19]
Harrington et al.

[11] Patent Number: 5,874,283
[45] Date of Patent: Feb. 23, 1999

[54] MAMMALIAN FLAP-SPECIFIC ENDONUCLEASE

[75] Inventors: John Joseph Harrington, 13700 Fairhill Rd. #514, Shaker Heights, Ohio 44120; Chih-Lin Hsieh; Michael R. Lieber, both of 11616 Clayton Rd., St. Louis, Mo. 63131

[73] Assignees: John Joseph Harrington, Cleveland, Ohio; Michael R. Lieber; Chih-Lin Hsieh, both of Arcadia, Calif.

[21] Appl. No.: 455,968

[22] Filed: May 30, 1995

[51] Int. Cl.$^6$ .............. C12N 1/20; C12N 9/22; C07H 21/04; C07K 1/00

[52] U.S. Cl. .............. 435/252.3; 435/199; 435/252.33; 435/320.1; 435/69.1; 536/23.2; 536/23.5; 530/350

[58] Field of Search .............. 435/252.3, 199, 435/69.1, 252.33, 320.1; 536/23.2, 23.5; 530/350

[56] References Cited

U.S. PATENT DOCUMENTS

| | | | |
|---|---|---|---|
| 5,324,830 | 6/1994 | Resnick et al. | 536/23.2 |
| 5,359,047 | 10/1994 | Donahue et al. | 536/23.5 |

OTHER PUBLICATIONS

Chow and Fraser, "Purification and Properties of Single Stand DNA–binding Endo–Exonuclease of *Neurospora crassa*," *J. Biol. Chem.*, 258:12010–12018 (1983).

Chow and Resnick, "Purification and Characterization of an Endo–exonuclease from *Saccharomyces cerevisiae* That is Influenced by the RAD52 Gene," *J. Biol. Chem.*, 262:17659–17667 (1987).

Chow and Resnick, "An endo–exonuclease activity of yeast that requires a functional RAD52 gene," *Molec. Gen. Genet.*, 211:41–48 (1988).

Habraken et al., "Yeast excision repair gene RAD2 encodes a single-stranded DNA endonuclease," *Nature*, 366:365–368 (1993).

Harosh et al., "Purification and Characterization of Rad3 ATPase/DNA Helicase from *Saccharomyces cerevisiae*," *J. Biol. Chem.*, 264:20532–20539 (1989).

Harrington and Lieber, "Functional domains within FEN–1 and RAD2 define a family of structure–specific endonucleases: implications for nucleotide excision repair," *Genes and Devel.*, 8:1344–1355 (1994).

Harrington and Lieber, "The characterization of a mammalian DNA structure–specific endonuclease," *EMBO Journal*, 13:1235–1246 (1994).

Harrington and Lieber, "DNA Structural Elements Required for FEN–1 Binding," *J. Biol. Chem.*, 270:1–6 (1995).

Hiraoka et al., "Sequence of Human FEN–1, a Structure–Specific Endonuclease, and Chromosomal Localization of the gene (FEN1) in Mouse and Human," *Genomics*, 25:220–225 (1995).

Koa et al., "Endo–exonuclease of *Aspergillus nidulans*," *Biochem. Cell Biol*, 68:387–392 (1990).

Lyamichev et al., "Structure–Specific Endonucleolytic Cleavage of Nucleic Acids by Eubacterial DNA Polymerases," *Science*, 260:778–783 (1993).

Park et al., "RAD25 (SSL2), the yeast homolog of the human xeroderma pigmentosum group B DNA repair gene, is essential for viability," *Proc. Natl. Acad. Sci.*, 89:11416–11420 (1992).

Sung et al., "RAD3 protein of *Saccharomyces cerevisiae* is a DNA helicase," *Proc. Natl. Acad. Sci.*, 84:8951–8955 (1987).

Szankasi and Smith, "A Role for Exonuclease I from *S. pombe* in Mutation Avoidance and Mismatch Correction," *Science*, 267:1166–1168 (1995).

Tomkinson et al., "Yeast DNA repair and recombinant proteins Rad1 and Rad10 constitute a single–stranded–DNA endonuclease," *Nature*, 362:860–862 (1993).

Hiroaka et al. Genomics 25(1): 220–5, Jan. 1, 1995.

Murray et al. Molecular and Cellular Biology 14(7): 4878–88, Jul. 1994.

*Primary Examiner*—Robert A. Wax
*Assistant Examiner*—Tekchand Saidha
*Attorney, Agent, or Firm*—Townsend & Townsend & Crew

[57] ABSTRACT

Compositions comprising human FEN-1(flap) endonucleases, nucleic acids encoding them, and methods for their use are provided.

6 Claims, 7 Drawing Sheets

FIGURE 1A

MGIQGLAKLIADVAPSAIRENDIKSYFGRKVAIDASMSI
YQFLIAVRQGGDVLQNEEGETTSHLMGMFYRTIRMMENG
IKPVYVFDGKPPQLKSGELAKRSERRAEAEKQLQQAQAA
GAEQEVEKFTKRLVKVTKQHNDECKHLLSLMGIPYLDAP
SEAEASCAALVKAGKVYAAATEDMDCLTFGSPVLMRHLT
ASEAKKLPIQEFHLSRILQELGLNQEQFVDLCILLGSDY
CESIRGIGPKRAVDLIQKHKSIEEIVRRLDPNKYPVPEN
WLHKEAHQLFLEPEVLDPESVELKWSEPNEEELIKFMCG
EKQFSEERIRSGVKRLSKSRQGSTQGRLDDFFKVTGSLS
SAKRKEPEPKGSTKKKAKTGAAGKFKRGK

FIGURE 1B

```
ATGGGAATTC AAGGCCTGGC CAAACTAATT GCTGATGTGG CCCCCAGTGC CATCCGGGAG
AATGACATCA AGAGCTAϵTT TGGCCGTAAG GTGGCCATTG ATGCCTCTAT GAGCATTTAT
CAGTTCCTGA TTGCTGTTCG CCAGGGTGGG GATGTGCTGC AGAATGAGGA GGGTGAGACC
ACCAGCCACC TGATGGGCAT GTTCTACCGC ACCATTCGCA TGATGGAGAA CGGCATCAAG
CCCGTGTATG TCTTTGATGG CAAGCCGCCA CAGCTCAAGT CAGGCGAGCT GGCCAAACGC
AGTGAGCGGC GGGCTGAGGC AGAGAAGCAG CTGCAGCAGG CTCAGGCTGC TGGGGCCGAG
CAGGAGGTGG AAAAATTCAC TAAGCGGCTG GTGAAGGTCA CTAAGCAGCA CAATGATGAG
TGCAAACATC TGCTGAGCCT CATGGGCATC CCTTATCTTG ATGCACCCAG TGAGGCAGAG
GCCAGCTGTG CTGCCCTGGT GAAGGCTGGC AAAGTCTATG CTGCGGCTAC CGAGGACATG
GACTGCCTCA CCTTCGGCAG CCCTGTGCTA ATGCGACACC TGACTGCCAG TGAAGCCAAA
AAGCTGCCAA TCCAGGAATT CCACCTGAGC CGGATTCTGC AGGAGCTGGG CCTGAACCAG
GAACAGTTTG TGGATCTGTG CATCCTGCTA GGCAGTGACT ACTGTGAGAG TATCCGGGGT
ATTGGGCCCA AGCGGCTGT GGACCTCATC CAGAAGCACA AGAGCATCGA GGAGATCGTG
CGGCGACTTG ACCCCAACAA GTACCCTGTG CCAGAAAATT GGCTCCACAA GGAGGCTCAC
CAGCTCTTCT TGGAACCTGA GGTGCTGGAC CCAGAGTCTG TGGAGCTGAA GTGGAGCGAG
CCAAATGAAG AAGAGCTGAT CAAGTTCATG TGTGGTGAAA AGCAGTTCTC TGAGGAGCGA
ATCCGCAGTG GGTCAAGAG GCTGAGTAAG AGCCGCCAAG GCAGCACCCA GGGCCGCCTG
GATGATTTCT TCAAGGTGAC CGGCTCACTC TCTTCAGCTA AGCGCAAGGA GCCAGAACCC
AAGGGATCCA CTAAGAAGAA GGCAAAGACT GGGGCAGCAG GAAGTTTAA AAGGGGAAAA
TAAA
```

FIGURE 2A

MGIHGLAKLIADVAPSAIRENDIKSYFGRKVAIDASMSIY
QFLIAVRQGGDVLQNEEGETTSLMGMFYRTIRMENGIKPV
YVFDGKPPQLKSGELAKRSERRAEAEKQLQQAQEAGMEEE
VEKFTKRLVKVTKQHNDECKHLLSLMGIPYLDAPSEAEAS
CAALAKAGKVYAAATEDMDCLTFGSPVLMRHLTASEAKKL
PIQEFHLSRVLQELGLNQEQFVDLCILLGSDYCESIRGIG
AKRAVDLIQKHKSIEEIVRRLDPSKYPVPENWLHKEAQQL
FLEPEVVDPESVELKWSEPNEEELVKFMCGEKQFSEERIR
SGVKRLSKSRQGSTQGRLDDFFKVTGSLSSAKRKEPEPKG
PAKKKAKTGGAGKFRRGK

FIGURE 2B

```
ATGGGAATTC ACGGCCTTGC CAAACTAATT GCTGATGTGG CCCCCAGTGC CATCCGTGAG
AATGACATCA AGAGCTACTT TGGTCGTAAA GTGGCCATCG ATGCCTCCAT GAGCATCTAC
CAGTTCCTGA TTGCTGTTCG TCAGGGTGGG GATGTGCTGC AGAACGAGGA GGGTGAGACC
ACCAGCCTGA TGGGCATGTT ATGGCAAACC ATCCGCATGG AGAATGGCAT CAAGCCTGTG
TACGTCTTTG ATGGCAAACC ACCACAGCTG AAGTCAGGCG AGCTGGCCAA GCGCAGTGAG
AGGCGCGCCG AGGCTGAGAA GCAACTGCAG CAGGCTCAGG AGGCTGGGAT GGAGGAGGAG
GTGGAGAAGT TCACCAAGAG GCTCGTGAAG GTCACCAAGC AACACAATGA TGAGTGCAAA
CACCTCGTGA GCCTCATGGG CATCCCTTAC CTTGATGCAC CAGCGAGGC AGAGGCCAGC
TGTGCTGCCC TGGCAAAGGC TGGCAAAGTC TATGCTGCGG CCACGGAGGA CATGGACTGC
CTCACTTTTG GCAGCCCCGT GCTAATGCGA CACTTAACTG CCAGTGAGGC CAAGAAGCTG
CCCATCCAAG AGTTCCATCT GAGCCGCGTC CTGCAGGAGC TGGGTCTGAA CCAGGAGCAG
TTTGTGGATC TGTGCATCCT GCTGGGTAGC GACTACTGCG AGAGCATCCG TGGCATTGGC
GCCAAGCGGG CTGTGGATCT CATCCAGAAA CATAAGAGCA TCGAGGAGAT CGTGAGGCGG
CTGGACCCCA GCAAGTACCC CGTTCCAGAG AACTGGCTCC ACAAGGAAGC CCAGCAGCTC
TTCCTGGAGC CAGAAGTAGT GGACCCAGAG TCTGTGGAGC TGAAGTGGAG CGAGCCAAAT
GAAGAAGAGT TGGTCAAATT TATGTGTGGT GAAAAGCAGT TTTCTGAAGA GCGAATTCGC
AGTGGGGTCA AGCGGCTGAG TAAGAGCCGC CAGGGCAGCA CCCAGGGACG CCTCGATGAT
TTCTTCAAGG TGACAGGCTC ACTCTCCTCA GCTAAGCGCA AGGAGCCAGA ACCCAAGGGG
CCTGCTAAGA AGAAAGCAAA GACTGGGGGA GCGGGGAAGT TCCGAAGGGG AAAATAAACC
TGTCCTTCCC CTCCACTGTC CTTGACCCCA GGCTGTCTAT CTGTTTTGTA CCCTGCGCTG
CAGCACATCC CTCTTGTCCC TCGTCTTGAG GAGAGTTCAT TGCTTCCAGC GCTCGCCTTC
AGAGCTTTCC CTCTCTTGAC CCTGTGGCAG GAAGGCCGTA GCTCTGCTTT TTCTCATTTT
TAGCTCAGGA AAGATGTCAG GCTCAAACCA CTTCTCAGGT TAATGGACAC TGTAGTCATT
GTTCTGTGCA ACTGCGAGCA ATGTCTTAAG GAAGAAGAAG ATAAAGCCGG GAGCGAGGCT
GGAGATAGTT TCCCAGCTGG CCAGCTGGTG GAGGAGAGGT GACTAGAACC TGACTGACTA
CTGCTCCTTC TAATTTCACT GTCCCTGAAA GATGCCCATC AGCCTGGGAT TCGCTGATGG
AAGAACTGCA AAGAGACGCA GCAGAGAGAA GTCTGGCTGA CAACAGATTT AGTACTGACC
AGCTGATTTT TGTGGGCAGA AATTTGAACT TGCTGCCTGC TGAGTCCAGT AGTTGTGCAG
GGAGTGAGAT GGCAGTGTTT AAGTTTTGAT TTGTAGTTTT TTGTTTTTGT CTCTCCCCTC
TCCAGTGTTG GGGATTGACC CCAGGGCAAA GGCATTAAGT GTGCCACTGA CCTGTGCCTC
CAAGTGATGT TCTGACAGCC TTTCTGAGGC AATCAATTGA ATTGAGGTTT TGGGAGAAGA
AACTGTTGTT CATAGGCTAT TTCTATTTTA AAGATGTGA AGAGAAAAAA AAAACAATAA
AATTATAAAA
```

FIGURE 3A

MGIKGLNAIISEHVPSAIRKSDIKSFFGRKVAIDASMSLYQ
FLIAVRQQDGGQLTNEAGETTSHLMGMFYRTLRMIDNGIKP
CYVFDGKPPDLKSHELTKRSSRRVETEKKLAEATTELEKMK
QERRLVKVSKEHNEEAQKLLGLMGIPYIIAPTEAEAQCAEL
AKKGKVYAAASEDMDTLCYRTPFLLRHLTFSEAKKEPIHEI
DTELVLRGLDLTIEQFVDLCIMLGCDYCESIRGVGPVTALK
LIKTHGSIEKIVEFIESGESNNTKWKIPEDWPYKQARMLFL
DPEVIDGNEINLKWSPPKEKELIEYLCDDKKFSEERVKSGI
SRLKKGLKSGIQGRLDGFFQVVPKTKEQLAAAAKRAQENKK
LNKNKNKVTKGR

FIGURE 3B

```
ATGGGTATTA AAGGTTTGAA TGCAATTATA TCGGAACATG TTCCCTCTGC TATCAGGAAA
AGCGATATCA AGAGCTTTTT TGGCAGAAAG GTTGCCATCG ATGCCTCTAT GTCTCTATAT
CAGTTTTTAA TTGCTGTAAG ACAGCAAGAC GGTGGGCAGT TGACCAATGA AGCCGGTGAA
ACAACGTCAC ACTTGATGGG TATGTTTTAT AGGACACTGA GAATGATTGA TAACGGTATC
AAGCCTTGTT ATGTCTTCGA CGGCAAACCT CCAGCTTTGA AATCTCATGA GTTGACAAAG
CGGTCTTCAA GAAGGGTGGA AACAGAAAAA AAACTGGCAG AGGCAACAAC AGAATTGGAA
AAGATGAAGC AAGAAAGAAG ATTGTTGAAG GTCTCAAAAG AGCATAATGA AGAAGCCCAA
AAATTACTAG GACTAATGGG AATCCCATAT ATAATAGCGC CAACGGAAGC TGAGGCTCAA
TGTGCTGAGT TGGCAAAGAA GGGAAAGGTG TATGCCGCAG CAAGTGAAGA TATGGACACA
CTCTGTTATA GAACACCCTT CTTGTTGAGA CATTTGACTT TTTCAGAGGC CAAGAAGGAA
CCGATTCACG AAATAGATAC TGAATTAGTT TTGAGAGGAC TCGACTTGAC AATAGAGCAG
TTTGTTGATC TTTGCATAAT GCTTGGTTGT GACTACTGTG AAAGCATCAG AGGTGTTGGT
CCAGTGACAG CCTTAAAATT GATAAAAACG CATGGATCCA TCGAAAAAAT CGTGGAGTTT
ATTGAATCTG GGGAGTCAAA CAACACTAAA TGGAAAATCC CAGAAGACTG GCCTTACAAA
CAAGCAAGAA TGCTGTTTCT TGACCCTGAA GTTATAGATG GTAACGAAAT AAACTTGAAA
TGGTCGCCAC CAAAGGAGAA GGAACTTATC GAGTATTTAT GTGATGATAA GAAATTCAGT
GAAGAAAGAG TTAAATCTGG TATATCAAGA TTGAAAAAAG GCTTGAAATC TGGCATTCAG
GGTAGGTTAG ATGGGTTCTT CCAAGTGGTG CCTAAGACAA GGAACAGCT GGCTGCTGCG
GCGAAAAGAG CACAAGAAAA TAAAAAATTG AACAAAAATA AGAATAAAGT CACAAAGGGA
AGAAGATGA
```

FIGURE 4A

MGVHSFWDIAGPTARPVRLESLEDKRMAVDASIWIYQFLKA
VRDQEGNAVKNSHITGFFRRICKLLYFGIRPVFVFDGGVPV
LKRETIRQRKERRQGKRESAKSTARKLQQQMKDKRDSDEVT
MDMIKEVQELLSRFGIPYITAPMEAEAQCAELLQLNLVDGI
ITDDSDVFLGGTKIYKNMFHEKNYVEFYDAESILKLLGLD
RKNMIELAQLLGSDYTNGLKGMGPVSSIEVIAEFGNLKNFK
DWYNNGQFDKRKQETENKFEKDLRKKLVNNEIILDDDFPSV
MVYDAYMRPEVDHDTTPFWGVPDLDMLRSFMKTQLGWPHE
KSDEILIPLIRDVNKRKKKGKQKRINEFFPREYISGDKKLN
TSKRISTATGKLKKRKM

FIGURE 4B

```
ATGGGTGTGC ATTCATTTTG GGATATTGCA GGTCCTACGG CAAGACCGGT CAGGCTGGAA
TCCTTGGAAG ATAAGAGAAT GGCAGTAGAT GCCTCCATTT GGATATATCA GTTTTTGAAA
GCTGTCCGTG ATCAGGAGGG GAATGCAGTG AAGAATTCTC ATATTACTGG GTTCTTTAGA
AGAATTTGTA AGCTATTATA CTTTGGCATT AGGCCGGTAT TCGTCTTTGA TGGTGGTGTG
CCCGTATTGA AAAGGGAAAC AATACGGCAG AGGAAAGAAA GAAGACAGGG AAAACGAGAG
AGTGCGAAAT CCACCGCTAG GAAGCTGCAA CAACAGATGA AGGATAAAAG AGATTCGGAT
GAGGTAACTA TGGATATGAT CAAAGAAGTG CAAGAATTAC TATCGAGGTT TGGAATCCCC
TATATCACTG CGCCTATGGA AGCTGAAGCA CAGTGTGCGG AATTGTTACA ACTAAACCTT
GTCGATGGTA TAATTACCGA TGACAGTGAT GTTTTCCTAT TTGGAGGTAC AAAGATCTAC
AAAAATATGT TCCACGAAAA GAACTATGTT GAATTTTATG ATGCGGAATC TATTTTAAAA
TTATTGGGCT TGGATAGAAA GAATATGATT GAGTTGGCAC AGCTTTTAGG GAGCGATTAC
ACGAATGGAT TGAAGGGTAT GGGTCCCGTT TCAAGCATTG AAGTGATTGC AGAATTTGGA
AACCTAAAAA ATTTTAAAGA CTGGTATAAT AATGGGCAGT TTGATAAACG TAAGCAAGAA
ACGGAAAATA AATTTGAAAA AGACCTGAGA AAAAAACTGG TAAATAACGA AATTATCTTA
GATGATGATT TTCCTAGCGT CATGGTTTAT GATGCGTATA TGAGACCAGA AGTCGATCAC
GATACCACGC CGTTTGTTTG GGGGGTACCA GATCTCGATA TGCTTCGTTC ATTCATGAAG
ACTCAACTAG GTTGGCCACA CGAAAAGTCT GATGAAATTC TCATTCCCTT AATTAGAGAT
GTTAATAAAC GCAAAAAGAA GGGGAAGCAA AAAAGGATTA ATGAATTTTT TCCAAGGGAG
TACATATCTG GTGATAAGAA GCTCAATACA AGTAAGAGAA TTTCAACCGC AACAGGTAAA
CTAAAGAAAA GAAAGATGTA A
```

```
TCGCGGAAGCTGTGAAAGCGGCAGACGGAACAGCACCGGGCTAGCCCGGCTTTGGCCATTCTGCTCCGAACATTCCTATTGTTGCCATTGCTCCTGTGCTACC
ATG GGA ATT CAC GGC CTT GCC ATC CTA ATT GCC CCC AGT GCC ATC CGT GAG AAT GAC ATC AAG AGC TAC
 M   G   I   H   G   L   A   I   L   I   A   P   S   A   I   R   E   N   D   I   K   S   Y
TTT GGT CGC AAA GTG GCC GAT GCC ATC TAC CAG TTC CTG ATT GCT GTT CGT CAG GGT GGG GAT GTG
 A   I   D   A   S   R   E   N   D   V   I   Y   Q   F   L   I   A   V   R   Q   G   G   D   V
CTG CAG AAC GAG GAG GGT GAG ACC ACC AGC ATG ATG TAC CGT ATC CGC ATG GAG AAT GGC CGC GAG
 L   Q   N   E   E   G   E   T   T   S   L   M   F   Y   R   T   I   R   M   E   N   G   R   A   E
CCT GTG TAC GTC TTT GAT GGC CAG CTG AAA CCA CAG TCA GGC CTG AAG CGC AGT GAG CGC AGG AAG GAG
 P   V   Y   V   F   D   G   Q   L   K   P   Q   S   G   L   K   R   S   E   R   R   K   E
GCT GAG CAA CTG CAG CAG AAT GAT GAG CAG GCT GAG CAC CAC CTC ATC GGC ATC CCT TAC CTT GAT GCA CCC AGC AAG
 A   E   Q   L   Q   Q   N   D   E   Q   A   E   H   H   L   M   G   I   P   Y   L   D   A   P   S   K
GTC ACC AAG CAA CAC TGT GCT GCC AAA GCT AAG GCT CTG TAT GCG GCG AAG AAG CTG TGC ATC GAT GCA TGG ACT
 V   T   K   Q   H   C   A   K   A   K   A   L   Y   A   A   K   K   L   C   I   D   A   W   T
GCA GAG GCC AGC CCC GTG CTG CTA ATG CGA CAC CTT ACT CAG GAG CAC ATC CAA CCC ATC GAG TTC CAT CTG AGC
 A   E   A   S   P   V   L   L   M   R   H   L   T   Q   E   H   I   Q   P   I   E   F   H   L   S
TTT GGC AGC CCC GTC CAG CAG CTG GGT AGC AAG CGC AAG CTG TGC ATC CTG CTG AGC GAC TAC TGC GAG
 F   G   S   P   V   Q   Q   L   G   S   K   R   K   L   C   I   L   L   S   D   Y   C   E
CGC GTC CTG CAG GAG CTA ATG CGG AGC CAG AAG CAT AAG CAG CAG AGC ATC GAG GAG ATC GTG AGG CGG
 R   V   L   Q   E   L   M   R   S   Q   K   H   K   Q   Q   S   I   E   E   I   V   R   R
AGC ATC CGT GGC ATT TAC CCC GTT CCA GAG GAA GCC CAG CAG CTC TTC CTG GAG CCA GAA GTA
 S   I   R   G   I   Y   P   V   P   E   E   A   Q   Q   L   F   L   E   P   E   V
CTG GAC CCC AGC AAG TAC CCC AAC TGG CTC CAC AAG GAG
 L   D   P   S   K   Y   P   N   W   L   H   K   E
```

FIG. 5A

```
GTG GAC CCA GAG TCT GTG GAG CTG AAG TGG AGC GAG CCA AAT GAA GAG TTG GTC AAA TTT ATG TGT GGT GAA AAG
 V   D   P   E   S   V   E   L   K   W   S   E   P   N   E   E   L   V   K   F   M   C   G   E   K

CAG TTT TCT GAA GAG CGA ATT CGC AGT GGG GTC AAG AGC CTG AAG AGC CAG GGC GGA CGC CTC
 Q   F   S   E   E   R   I   R   S   G   V   K   S   L   R   Q   G

GAT GAT TTC AAG GTC ACA GGC TCA CTC TCC TCA GCT AAG CGC AAG GAG CCA GAA CCC AAG GGG CCT GCT AAG AAG
 D   D   F   K   V   T   G   S   L   S   A   K   R   K   E   P   E   P   K   G   P   A   K   K

AAA GCA AAG ACT GGG GGA GCG GGG TTC CGA AGG GGA AAA AAA TAA
 K   A   K   T   G   G   A   G   F   R   R   G   K   K   *

GGC TGT CTA TCT GTT TTG TAC CCT CGG CTG CAG CAC ATC CCT CTT GTC CCT CGT GAG GAG AGT TCA TTG CTT CCA

GCG CTG CCC TTC AGA GCT TTC CTC TTG ACC CTG TGG CAG GGC CGT AGC TCT GCT TTT TCT CAT TTT TAG CTC

AGG AAA GAT GTC AGG CTC AGG GAT AAA GCC CTC AAA CCA CTT GTA GTC ATT GTT CTG TGC AAC TGC GAG CAA TGT

CTT AAG GAA GAA GAT AAA GCC GGG AGC GAG CTG TCC CCA GCT GGA AGT TTC AAA GAT AGT AGT GGG CAG GAG TGA

CTA GAA CCT GAC TGA CTA CTG CTT CTA ATT TCA CTG CTG ACA ACA GAT TTA GTA CTG ACC CAT CAG CCT CGC TGG

AAG AAC TGC AAA GAG ACG CAG CAG GTC TGG GTA GTT CCA AGT CTG GTG CAG TGG AGA GAA GTC ACC AGT TTG TGG GCA

GAA ATT TGA ACT TGC TGC TCT CTG CTG CCC AGT TTC TGA CAG CCT TGG GGC GAT TGA CCC CAG AAT CAA TTG GAT TTG TAG

TTT TTT GTT TTT GTC ATG TTC TGC TCT CCC TCC AGT CAG CCT TGA GGT TTT GGG AAA GGC ATT AAG TGT GCC ACT GAC CTG

TGC CTC CAA GTG ATG TTC TGA CAG CCT TTC TGA CAG CCT TGA AAT CAA TTG AAT TGA AGA AGA AAC TGT TGT TCA

TAG GCT ATT TCT ATT TTA AAA GAT GTG AAG AGA AAA AAA CAA TAA AAT TAT AAA A
```

FIG. 5B

MAMMALIAN FLAP-SPECIFIC ENDONUCLEASE

TECHNICAL FIELD

The invention provides novel polypeptides which are substantially identical to a naturally-occurring mammalian flap-specific endonuclease, polynucleotides encoding such polypeptides, polynucleotide derivatives of naturally-occurring mammalian flap-endonuclease genes and MRNA, antibodies which are reactive with such polypeptides, polynucleotide hybridization probes and PCR amplification probes for detecting polynucleotides which encode such novel polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting a pathological condition in a patient, methods and compositions for diagnostic polynucleotide hybridization and/or amplification, methods for screening for antineoplastic agents and carcinogens, methods for diagnostic staging of neoplasia, methods for producing recombinant flap endonuclease for use as research or diagnostic reagents, methods for producing antibodies reactive with the novel polypeptides, and methods for producing transgenic nonhuman animals expressing the novel polypeptides encoded by a transgene. The invention also provides novel molecular cloning techniques and reagents involving cleavage of a flap or nick with a flap endonuclease.

BACKGROUND

DNA can be damaged by a variety of environmental insults, including antitumor drugs, radiation, carcinogens, mutagens and other genotoxins. Chemical changes in the component nucleotides or of DNA secondary and tertiary structure which arise from such external causes are all considered herein to be DNA modification or damage. In addition, it is recognized that certain chemical and/or structural modifications in DNA may occur naturally, and may play a role in, for example, DNA replication, expression, or the coordinate regulation of specific genes. It has been proposed that some types of DNA modification or damage arising from external sources are similar to, or even mimic, certain types of natural DNA chemical and/or structural modification.

DNA damage can lead to mutations and cancer, as well as cell death; the latter is exploited in chemo- and radiotherapeutics. A better understanding of DNA chemical and structural modifications, including DNA damage, would also be helpful in that it might serve as the basis for developing an enhanced ability to repair or otherwise modify the effects of such damage, leading in turn to improved organismal or tissue resistance to DNA damaging agents.

DNA Repair and Endonuclease Activity

Nucleotide excision repair (NER) is a major pathway by which damaged nucleotides are removed from DNA. The biochemical steps leading to the repair of damaged DNA bases include recognition of damage, incision and removal of the damaged strand, DNA synthesis to replace the excised nucleotides, and ligation. Genetic studies in yeast have identified seven repair genes that are absolutely required for the initial DNA incisions to occur. These genes have been shown to encode nucleases (RAD1/10 and RAD2) (Habraken et al. (1993) *Nature* 366: 365; Tomkinson et al. (1993) *Nature* 362: 860), helicases (RAD3 and RAD25) (Sung et al. (1987) *Proc. Natl. Acad. Sci. (USA)* 84: 8951; Harosh et al. (1989) *J. Biol. Chem.* 264: 20532; Park et al. (1992) *Proc. Natl. Acad. Sci. (USA)* 89: 11416), and a damage recognition protein (RAD14). Current models indicate specific branched DNA structures at the site of DNA damage in yeast. The resulting branched DNA structures may then be cleaved by the single-stranded endonucleases, RAD1/10 and RAD2.

U.S. Pat. No. 5,359,047 reports a mammalian cellular factor that selectively recognizes and binds DNA damaged or modified by the anticancer drug, cis-diamminedichloroplatinum (II) (cisplatin). This DNA structure-specific recognition protein (SSRP) recognizes and selectively binds to a structural motif present in damaged DNA characteristic of DNA damaged by therapeutically active platinum compounds.

U.S. Pat. No. 5,324,830 reports a chimeric enzyme comprised of an endo-exonuclease, RhoNUC, from *S. cerevisiae* which functions in both repair and recombination (Chow and Resnick (1987) *J. Biol. Chem.* 262: 17659; and Chow and Resnick (1988) *Molec. Gen. Genet.* 211: 41). Repair processes in the yeast *Saccharomyces cerevisiae* are under extensive genetic control involving over 50 genes; among these are genes that function in recombinational repair as well as normal meiotic and mitotic recombination (Kunz and Haynes (1981) *Annu. Rev. Genet.* 15: 57; Game, J. C. (1983) in: *Yeast Genetics, Fundamental and Applied Aspects* (eds. Spencer, J. F. T., Spencer, D., and Smith, A.) pgs. 109–137, Springer-Verlag New York, Inc., New York, and Resnick, M. A. (1987) in: *Meiosis* (ed. Moens, P.), pgs. 157–212, Academic Press, New York).

Nuclease activity associated with the *Escherichia coli* recBCD proteins is required for much of host recombination and also for chi stimulated lambda bacteriophage (Chaudhury and Smith (1984) *Proc. Natl. Acad. Sci. (USA)* 81: 7850). Holloman and Holliday (1973) *J. Biol. Chem.* 248: 8107 have described nuclease alpha from the eucaryote *Ustilago maydis* that is required for recombination and DNA repair. An endo-exonuclease from *Neurospora crassa* has also been implicated in recombination and repair (Chow and Fraser (1979) *Can. J. Biochem.* 57: 889; Chow and Fraser (1983) *J. Biol. Chem.* 258: 12010; and Ramotar et al. (1987) *J. Biol. Chem.* 262: 425). The phenotypes of mutants deficient or altered in this specific nuclease activity include meiotic sterility and sensitivity to ultraviolet light, X-rays, and/or alkylating agents (Fraser, M. J., et al. (1990) in: *DNA Repair and Mutagenesis in Eucaryotes* (Generoso et al., eds) pgs. 63–74, Plenum Publishing Corp., New York). A similar endo-exonuclease has also been isolated from *Aspergillus nidulans* (Koa et al. (1990) *Biochem. Cell. Biol.* 68: 387–392) and from mammalian mitochondria (Tomkinson et al. (1986) *Nucl. Acids Res.* 14: 9579.

Recombination and Endonuclease Activity

Homologous recombination (or general recombination) is defined as the exchange of homologous segments anywhere along a length of two DNA molecules. An essential feature of general recombination is that the enzymes responsible for the recombination event can presumably use any pair of homologous sequences as substrates, although some types of sequence may be favored over others. Both genetic and cytological studies have indicated that such a crossing-over process occurs between pairs of homologous chromosomes during meiosis in higher organisms.

Alternatively, in site-specific recombination, exchange occurs at a specific site, as in the integration of phage λ into the E. coli chromosome and the excision of λ DNA from it. Site-specific recombination involves specific sequences of the phage DNA and bacterial DNA. Within these sequences there is only a short stretch of homology necessary for the recombination event, but not sufficient for it. The enzymes involved in this event generally cannot recombine other pairs of homologous (or nonhomologous) sequences, but act specifically on the particular phage and bacterial sequences.

Although both site-specific recombination and homologous recombination are useful mechanisms for genetic engineering of DNA sequences, targeted homologous recombination provides a basis for targeting and altering essentially any desired sequence in a duplex DNA molecule, such as targeting a DNA sequence in a chromosome for replacement by another sequence. Site-specific recombination has been proposed as one method to integrate transfected DNA at chromosomal locations having specific recognition sites (O'Gorman et al. (1991) *Science* 251: 1351; Onouchi et al. (1991) *Nucleic Acids Res.* 19: 6373). Unfortunately, since this approach requires the presence of specific target sequences and recombinases, its utility for targeting recombination events at any particular chromosomal location is severely limited in comparison to targeted general recombination.

For these reasons and others, targeted homologous recombination has been proposed for treating human genetic diseases. Human genetic diseases include: (1) classical human genetic diseases wherein a disease allele having a mutant genetic lesion is inherited from a parent (e.g., adenosine deaminase deficiency, sickle cell anemia, thalassemias), (2) complex genetic diseases like cancer, where the pathological state generally results from one or more specific inherited or acquired mutations, and (3) acquired genetic disease, such as an integrated provirus (e.g., hepatitis B virus). However, current methods of targeted homologous recombination are inefficient and produce desired homologous recombinants only rarely, necessitating complex cell selection schemes to identify and isolate correctly targeted recombinants.

A primary step in homologous recombination is DNA strand exchange, which involves a pairing of a DNA duplex with at least one DNA strand containing a complementary sequence to form an intermediate recombination structure containing heteroduplex DNA (see, Radding, C. M. (1982) *Ann. Rev. Genet.* 16: 405; U.S. Pat. No. 4,888,274). The heteroduplex DNA may take several forms, including a triplex form wherein a single complementary strand invades the DNA duplex (Hsieh et al. (1990) *Genes and Development* 4: 1951) and, when two complementary DNA strands pair with a DNA duplex, a classical Holliday recombination joint or chi structure (Holliday, R. (1964) *Genet. Res.* 5: 282) may form, or a double-D loop. Once formed, a heteroduplex structure may be resolved by strand breakage and exchange, so that all or a portion of an invading DNA strand is spliced into a recipient DNA duplex, adding or replacing a segment of the recipient DNA duplex. Alternatively, a heteroduplex structure may result in gene conversion, wherein a sequence of an invading strand is transferred to a recipient DNA duplex by repair of mismatched bases using the invading strand as a template (*Genes*, 3rd Ed. (1987) Lewin, B., John Wiley, New York, N.Y.; Lopez et al. (1987) *Nucleic Acids Res.* 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules makes targeted homologous recombination a powerful method in genetic engineering and gene manipulation.

The ability of mammalian and human cells to incorporate exogenous genetic material into genes residing on chromosomes has demonstrated that these cells have the general enzymatic machinery for carrying out homologous recombination required between resident and introduced sequences. These targeted recombination events can be used to correct mutations at known sites, replace genes or gene segments with defective ones, or introduce foreign genes into cells. The efficiency of such gene targeting techniques is related to several parameters: the efficiency of DNA delivery into cells, the type of DNA packaging (if any) and the size and conformation of the incoming DNA, the length and position of regions homologous to the target site (all these parameters also likely affect the ability of the incoming homologous DNA sequences to survive intracellular nuclease attack), the efficiency of recombination at particular chromosomal sites and efficient and correct resolution (repair) of overlapped recombination joints and intermediate recombination structures.

Unfortunately, exogenous sequences transferred into eukaryotic cells undergo homologous recombination with homologous endogenous sequences only at very low frequencies, and are so inefficiently recombined that large numbers of cells must be transfected, selected, and screened in order to generate a desired correctly targeted homologous recombinant (Kucherlapati et al. (1984) *Proc. Natl. Acad. Sci. (U.S.A.)* 81: 3153; Smithies, O.(1985) *Nature* 317: 230; Song et al. (1987) *Proc. Natl. Acad. Sci. (U.S.A.)* 84: 6820; Doetschman et al. (1987) *Nature* 330: 576; Kim and Smithies (1988) *Nucleic Acids Res.* 16: 8887; Doetschman et al. (1988) op.cit.; Koller and Smithies (1989) op.cit.; Shesely et al. (1991) *Proc. Natl. Acad. Sci. (U.S.A.)* 88: 4294; Kim et al. (1991) *Gene* 103: 227).

Koller et al. (1991) *Proc. Natl. Acad. Sci. (U.S.A.)* 88: 10730 and Snouwaert et al. (1992) *Science* 257: 1083, have described targeting of the mouse cystic fibrosis transmembrane regulator (CFTR) gene for the purpose of inactivating, rather than correcting, a murine CFTR allele. Koller et al. employed a large (7.8 kb) homology region in the targeting construct, but nonetheless reported a low frequency for correct targeting (only 1 of 2500 G418-resistant cells were correctly targeted). Thus, even targeting constructs having long homology regions are inefficiently targeted.

Several proteins or purified extracts having the property of promoting homologous recombination (i.e., recombinase activity) have been identified in prokaryotes and eukaryotes (Cox and Lehman (1987) *Ann. Rev. Biochem.* 56:229; Radding, C. M. (1982) op.cit.; Madiraju et al. (1988) *Proc. Natl. Acad. Sci. (U.S.A.)* 85: 6592; ; McCarthy et al. (1988) *Proc. Natl. Acad. Sci. (U.S.A.)* 85: 5854; Lopez et al. (1987) op.cit., which are incorporated herein by reference). These general recombinases presumably promote one or more steps in the formation of homologously-paired intermediates, strand-exchange, gene conversion, and/or other steps in the process of homologous recombination. WO93/22443 discloses the use of recA to promote homologous recombination of gene correction and gene targeting vectors in vivo, including its use in gene therapy.

Thus, there exists a need in the art for compositions and methods of modulating DNA repair; compositions and methods for pharmaceutical development assays to identify agents that modulate DNA repair and cell proliferation; novel DNA repair and/or DNA replication and/or DNA recombination enzymes, compositions thereof, and encoding polynucleotides; and methods and compositions for using such enzymes to efficiently alter predetermined endogenous genetic sequences by nonhomologous and/or homologous recombination in vivo by introducing one or more exogenous targeting polynucleotide(s) that efficiently and specifically homologously pair with a predetermined endogenous DNA sequence or nonhomologously integrate. There exists a need in the art for high-efficiency gene targeting and gene therapy, so that complex in vitro selection protocols (e.g., neo gene selection with G418) which are of limited utility for in vivo gene therapy on affected individuals, are avoided. There also exists a need in the art for transgenic animals, such as knockout mice, which lack one or more DNA repair/DNA replication/DNA recombination enzymes; such mice can be sold as laboratory reagents and for pharmaceutical and toxicological testing. There also exists a need in the art for diagnostic methods employing novel DNA repair/DNA replication/DNA recombination enzymes and/or polynucleotides which encode such enzymes or substantially identical sequence variants thereof.

The references discussed herein are provided solely for their disclosure prior to the filing date of the present application. Nothing herein is to be construed as an admission that the inventors are not entitled to antedate such disclosure by virtue of prior invention.

SUMMARY

The present invention provides several novel methods and compositions relating to FLAP endonucleases, including but not limited to the human and murine FEN-1 FLAP endonuclease polypeptide and gene sequences, and novel deletion mutants of a Saccharomyces RAD2 gene and protein. These methods and compositions have a variety of applications, such as for modulating DNA repair/replication/recombination activities, for performing a variety of molecular cloning techniques, for performing a variety of diagnostic assays, and for screening for modulators of FLAP endonuclease activities. These methods utilize polynucleotide sequences encoding FLAP endonuclease proteins and polynucleotides which are substantially identical to naturally-occurring polynucleotide sequences (e.g., cDNA or genomic gene) that encode such FLAP endonuclease proteins.

In one aspect of the invention, FLAP endonuclease polypeptides and compositions thereof are provided. In one embodiment, FLAP endonuclease polypeptides comprise polypeptide sequences which are substantially identical to a sequence shown in FIG. 1 (panel A) of FIG. 5, designated human FEN-1, or FIG. 2 (panel A), designated mouse FEN-1, or a cognate gene sequence in another species, typically mammalian, most usually rodent or primate. An example of a FEN-1 polypeptide is the 380 amino acid long polypeptide of SEQ ID NO: 1 or the 378 amino acid long polypeptide of SEQ ID NO: 3. An example of a FEN-1 polynucleotide is a polynucleotide having the nucleotide sequence of SEQ ID NO: 2 or SEQ ID NO: 4. Also provided are yeast FEN-1 polypeptides having endonuclease activity, such as the Saccharomyces FEN-1 polypeptide sequence shown in FIG. 3 (panel A) as SEQ ID NO: 5 and substantially identical polypeptides. Muteins, fragments, and other structural variants, polymorphic sequence alleles, including naturally-occurring allelic variants are also encompassed in the invention. Preferably, the FLAP endonuclease polypeptides and polynucleotides are isolated and/or substantially pure, or replicated, integrated, or expressed in a host species other than human or mouse cells or Saccharomyces cells. Preferably, FEN-1 polypeptides have a detectable endonuclease activity, such as a 5' flap cleavage activity, which typically substantially lacks 3' flap cleavage activity and/or single-strand cleavage activity.

Polynucleotide sequences encoding FEN-1 polypeptides are provided. The characteristics of the cloned sequences are given, including the nucleotide and predicted amino acid sequences of mammalian FEN-1 in FIG. 1 (SEQ ID NOs: 1 and 2), FIG. 2 (SEQ ID NOS: 3 and 4), of FIG. 5 and the nucleotide and predicted amino acid sequences of the yeast cognate gene to FEN-1, in FIG. 3 (SEQ ID NOS: 5 and 6). Polynucleotides comprising these sequences can serve as templates for the recombinant expression of quantities of FEN-1 polypeptides, such as human FEN-1 and mouse FEN-1, and variants thereof, such as muteins and the like. Polynucleotides comprising these sequences can also serve as probes for nucleic acid hybridization to detect the transcription rate and mRNA abundance of FEN-1 mRNA in individual lymphocytes (or other cell types) by in situ hybridization, and in specific cell populations by Northern blot analysis and/or by in situ hybridization (Alwine et al.(1977) *Proc. Natl. Acad. Sci. U.S.A.* 74: 5350) and/or PCR amplification and/or LCR detection. Such recombinant polypeptides and nucleic acid hybridization probes have utility for in vitro diagnostic methods for identification of genome instability and neoplasia or preneoplasia, for diagnosis and treatment of pathological conditions and genetic diseases linked to the FEN-1 locus, and for forensic identification of human individuals, for gene therapy of FEN-1 deficiency conditions and neoplasia, among other uses apparent to those of skill in the art.

In addition to polynucleotides which are substantially identical to all or a portion of a naturally-occurring mammalian FEN-1 gene or mRNA, the invention provides polynucleotides encoding a mammalian FEN-1 polypeptide. Such polynucleotides are provided with reference to the novel deduced polypeptide sequence information provided in FIGS. 1 and 2. Polynucleotides encoding mammalian FEN-1 polypeptides can be constructed by those skilled in the art on the basis of the disclosed SEQ ID NO: 1 and SEQ ID NO: 3 in view of the degeneracy of the genetic code. In an embodiment, the FEN-1 polynucleotides encode a full-length FEN-1 polypeptide of SEQ ID NO: 1 or SEQ ID NO: 3. In an embodiment, the FEN-1 polynucleotides encode a mutein or analog of human or mouse FEN-1. FEN-1 polynucleotides can also encode fragments of a mammalian FEN-1 polypeptide, and/or fusion proteins comprising a full-length FEN-1 polypeptide or fragment or analog thereof in polypeptide linkage to a heterologous polypeptide (e.g., epitope tag, β-galactosidase, immunoglobulin, glutathione-S-transferase, non-FLAP nuclease, polymerase, and the like).

The invention also provides methods for producing a substantially purified FLAP endonuclease, such as a yeast or mammalian FEN-1 protein. Such methods typically comprise expressing in a host cell a heterologous polynucleotide consisting of (1) a polynucleotide sequence encoding FEN-1 operably linked to (2) a heterologous transcription regulatory region (e.g., promoter and enhancer) capable of driving transcription of the linked FEN-1 sequence in the host cell to produce a mRNA which can be translated in the host cell into a FEN-1 polypeptide, preferably having FLAP endonuclease activity. Typically, transcription control sequences in the heterologous polynucleotide include transcription termination sequences, polyadenylation sequences, and the like. The heterologous polynucleotide will also include sequences such that the transcribed RNA has a suitable ribosome binding site and untranslated sequences to ensure efficient translation in the host cell; as the host cell may be selected to be prokaryotic (e.g., E. coli) or eukaryotic (e.g., yeast, CHO cells, HeLa cells, etc.), the practitioner will select compatible transcription and translation control sequences appropriate for use in the selected host cell. In an embodiment, the FEN-1 polypeptide expressed is in polypeptide linkage to a signal sequence to effect compartmentalization and/or secretion from the host cell.

The invention provides polynucleotides comprising a FEN-1 encoding sequence operably linked to a heterologous transcriptional regulatory sequence, such as for example a prokaryotic promoter or a eukaryotic promoter, and optionally enhancer, which is not present adjacent to a naturally-occurring FEN-1 gene. For example and not limitation, suitable heterologous promoters include HSV tk promoter and SV40 large T antigen promoter/enhancer, among others.

The invention also provides a method for producing substantially pure FEN-1 polypeptide having detectable endonuclease activity; the method comprises expressing a FEN-1 polynucleotide in a host cell under transcriptional control of a heterologous promoter whereby FEN-1 polypeptide is expressed and collected in substantially purified form.

The invention also provides ΔRAD2 endonuclease polypeptides and compositions thereof, wherein said ΔRAD2 endonuclease polypeptides consist of a yeast RAD2 polynucleotide substantially lacking a spacer (S) region, wherein the carboxyl-terminal portion of the N region is in polypeptide linkage with the I region with a truncated spacer of 0 to 25 amino acids, preferably a spacer of 14 amino acids, typically consisting of —QKRESAKSTARAR— (SEQ ID NO: 13). For example, the Saccharomyces ΔRAD polypeptide of FIG. 4 (panel A), having SEQ ID NO: 7, is a suitable ΔRAD2 endonuclease polypeptide having detectable 5' flap cleavage activity.

The invention also provides antisense polynucleotides complementary to polynucleotides encoding FEN-1 polypeptide sequences, typically complementary to polynucleotide sequences which are substantially identical to a naturally-occurring mammalian FEN-1 gene sequence. Such antisense polynucleotides are employed to inhibit transcription and/or translation of the FEN-1 mRNA species and thereby effect a reduction in the amount of the respective FEN-1 polypeptide in a cell (e.g., a neoplastic cell of a patient). Such antisense polynucleotides can function as FEN-1-modulating agents by inhibiting the formation of FEN-1-required for DNA replication and/or repair of DNA damage (e.g., resulting from chemotherapy with a DNA-damaging agent such as bleomycin, cisplatin, nitrogen mustard, doxyrubicin, ionizing radiation, and the like) or maintenance of aneuploid genomes characteristic of neoplastic variant cells. The antisense polynucleotides can promote cell death in susceptible cells (e.g., cells requiring FEN-1 activity for DNA repair or replication). The FEN-1 antisense polynucleotides are substantially identical to at least 25 contiguous nucleotides of the complementary sequence of the FEN-1 cDNA sequence shown in FIG. 1 (panel B) and denoted SEQ ID NO: 2 or FIG. 2 (panel B) and denoted SEQ ID NO: 4. The FEN-1 antisense polynucleotides are typically ssDNA, ssRNA, methylphosphonate backbone nucleic acids, phosphorothiolate backbone, polyamide nucleic acids, and the like antisense structures known in the art. In one aspect of the invention, an antisense polynucleotide is administered to inhibit transcription and/or translation of FEN-1 in a cell.

In one embodiment, candidate therapeutic agents are identified by their ability to block the binding of a FEN-1 polypeptide to a DNA flap substrate and/or block the endonucleolytic activity of a FEN-1 polypeptide to cleave a DNA flap substrate. The FEN-1 polypeptide preferably is a full-length mature FEN-1 protein. Typically, the FEN-1 polypeptide comprises an amino acid sequence identical to a naturally-occurring mammalian FEN-1 protein sequence, although mutant FEN-1 polypeptides are sometimes used if the mutant FEN-1 polypeptide binds to and/or catalyzes cleavage of a DNA flap substrate under control assay conditions (e.g., physiological conditions). Agents are tested for their ability to alter binding and/or cleavage of DNA flap structures (or nicked DNA) by a FEN-1 polypeptide under suitable assay binding conditions. One means for detecting binding of a FEN-1 polypeptide to a DNA flap structure is to immobilize the DNA flap structure, such as by covalent or noncovalent chemical linkage to a solid support, often via a spacer sequence, and to contact the immobilized flap substrate with a FEN-1 polynucleotide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a DNA flap substrate to a full-length human or mouse FEN-1 polypeptide. Binding of the labeled FEN-1 polypeptide to the immobilized DNA flap substrate is measured by determining the extent to which the labeled FEN-1 polypeptide is immobilized as a result of a specific binding interaction. Such specific binding may be reversible, or may be optionally irreversible if a cross-linking agent is added in appropriate experimental conditions. Alternatively, the DNA flap substrate may be labelled (e.g., by incorporation of a radiolabeled or biotinylated nucleotide) and the FEN-1 polypeptide immobilized. In one variation, the degree of enzymatic cleavage of the flap substrate by the FEN-1 polypeptide is quantitated, such as by release of labeled flap nucleotides from an immobilized flap substrate. Agents that inhibit or augment the formation of bound complexes (or flap cleavage activity) as compared to a control binding reaction (or flap cleavage reaction) lacking agent are thereby identified as FEN-1-modulating agents and are candidate therapeutic agents.

In a variation of the invention, polynucleotides of the invention are employed for diagnosis of pathological conditions or genetic disease that involve neoplasia, aging, or other medical conditions related to FEN-1 function, and more specifically conditions and diseases that involve alterations in the structure or abundance of a FEN-1, or which are linked to a pathognomonic FEN-1 allele which can be detected by RFLP and/or allele-specific PCR.

The invention also provides antibodies which bind to FEN-1 with an affinity of about at least $1 \times 10^7$ M$^{-1}$ and which lack specific high affinity binding for other mammalian proteins (e.g., albumin, DNA polymerase α). Such antibodies can be used as diagnostic reagents to identify cells exhibiting altered FEN-1 abundance or structure (e.g., preneoplastic or neoplastic cells) in a cellular sample from a patient (e.g., a lymphocyte sample, a solid tissue biopsy) as being cells which contain an increased amount of FEN-1 polypeptide as compared to non-neoplastic cells of the same cell type(s). Frequently, anti-FEN-1 antibodies are included as diagnostic reagents for immunohistopathology staining of cellular samples in situ. Additionally, anti-FEN-1 antibodies may be used therapeutically by targeted delivery to neoplastic cells (e.g., by cationization or by liposome/immunoliposome delivery).

The invention also provides FEN-1 polynucleotide probes for diagnosis of disease states (e.g., neoplasia or preneoplasia) by detection of a FEN-1 mRNA or rearrangements or amplification of the FEN-1 gene in cells explanted from a patient, or detection of a pathognomonic FEN-1 allele (e.g., by RFLP or allele-specific PCR analysis). Typically, the detection will be by in situ hybridization using a labeled (e.g., $^{32}$P, $^{35}$S, $^{14}$C, $^3$H, fluorescent, biotinylated, digoxigeninylated) FEN-1 polynucleotide, although Northern blotting, dot blotting, or solution hybridization on bulk RNA or poly A$^+$ RNA isolated from a cell sample may be used, as may PCR amplification using FEN-1-specific primers. Cells which contain an altered amount (typically a significant increase) of FEN-1 mRNA as compared to non-neoplastic cells of the same cell type(s) will be identified as candidate diseased cells. Similarly, the detection of pathognomonic rearrangements or amplification of the FEN-1 gene locus or closely linked loci in a cell sample will identify the presence of a pathological condition or a predisposition to developing a pathological condition (e.g., cancer, genetic disease). The polynucleotide probes are also used for forensic identification of individuals, such as for paternity testing or identification of criminal suspects or unknown decedents.

The present invention also provides a method for diagnosing a disease (e.g., neoplasia) in a human patient, wherein a diagnostic assay (e.g., immunohistochemical staining of fixed cells by an antibody that specifically binds human FEN-1) is used to determine if a predetermined pathognomonic concentration of FEN-1 polypeptide or its encoding mRNA is present in a biological sample from a human patient; if the assay indicates the presence of FEN-1 polypeptide or its encoding mRNA outside of the normal range (e.g., beyond the predetermined pathognomonic concentration), the patient is diagnosed as having a disease condition or predisposition.

The invention also provides therapeutic agents which inhibit neoplasia or apoptosis by modulating FEN-1 function by inhibiting or augmenting formation of enzymatically active FEN-1, such agents can be used as pharmaceuticals. Such pharmaceuticals will be used to treat a variety of human and veterinary diseases, such as: neoplasia, hyperplasia, neurodegenerative diseases, aging, AIDS, fungal infection, and the like. In an embodiment, the agent consists of a gene therapy vector encoding an enzymatically active FEN-1 polypeptide, or alternatively an enzymatically inactive FEN-1 polypeptide which can competitively inhibit endogenous FEN-1 function.

The invention also provides methods for identifying polypeptide sequences which bind to a FEN-1 polypeptides. For example, a yeast two-hybrid screening system can be used for identifying polypeptide sequences that bind to FEN-1. Yeast two-hybrid systems wherein one GAL4 fusion protein comprises a FEN-1 polypeptide sequence, typically a full-length or near full-length FEN-1 polypeptide sequence (e.g., a polypeptide sequence of FIGS. 1 or 2), and the other GAL4 fusion protein comprises a cDNA library member can be used to identify cDNAs encoding proteins which interact with the FEN-1 polypeptide, can be screened according to the general method of Chien et al. (1991) op.cit. Alternatively, an *E. coli*/BCCP interactive screening system (Germino et al. (1993) *Proc. Natl. Acad. Sci. (U.S.A.)* 90: 933; Guarente L (1993) *Proc. Natl. Acad. Sci. (U.S.A.)* 90: 1639, incorporated herein by reference) can be used to identify interacting protein sequences. Also, an expression library, such as a λgt11 cDNA expression library, can be screened with a labelled FEN-1 polypeptide to identify cDNAs encoding polypeptides which specifically bind to the FEN-1 polypeptide. For these procedures, cDNA libraries usually comprise mammalian cDNA populations, typically human, mouse, or rat, and may represent cDNA produced from RNA of one cell type, tissue, or organ and one or more developmental stage. Specific binding for screening cDNA expression libraries is usually provided by including one or more blocking agent (e.g., albumin, nonfat dry milk solids, etc.) prior to and/or concomitant with contacting the labeled FEN-1 polypeptide (and/or labeled anti-FEN-1 polypeptide antibody).

In one aspect, the invention provides non-human animals (e.g., mice) which comprise a homozygous pair of functionally disrupted endogenous FEN-1 alleles. Such functionally disrupted endogenous FEN-a alleles typically result from homologous gene targeting, and often comprise a naturally-occurring FEN-1 allele which is (1) disrupted by deletion of an essential structural sequence (e.g., exon) or regulatory sequence (e.g., promoter, enhancer, polyadenylation site, splice junction site) or (2) disrupted by integration of an exogenous polynucleotide sequence (e.g., neo$^R$ gene) into an essential structural sequence (e.g., exon) or regulatory sequence (e.g., promoter, enhancer, polyadenylation site, splice junction site). Such FEN-1 knockout animals can be sold commercially as test animals (e.g., as a preneoplastic animal for testing genotoxic and/or carcinogenic agents, such as a p53 knockout mouse or the Harvard OncoMouse™), bred to transfer the disrupted FEN-1 allele (s) into other genetic backgrounds, and sold as disease models for screening for therapeutic agents, for developing immunodeficient mice substantially lacking the capacity to undergo immunoglobulin VDJ rearrangement and/or isotype switching, recombination-deficient mice, and the like. Such knockout animals have a wide variety of utilities in addition to being diagnostic reagents to quantify genotoxicity of a compound or serve as radiosensitive animals, including serving as pets and sources of animal protein (e.g., as a foodstuff), among many other practical presently available uses.

In one aspect of the invention, transgenic nonhuman animals, such as mice, bearing a transgene encoding a FEN-1 polypeptide are provided. Such transgenes may be homologously recombined into the host chromosome or may be non-homologously integrated. Such transgenes can often be present in a mouse lacking functional endogenous mouse FEN-1 (i.e., a FEN-1 knockout background), and typically such transgenes are human and can comprise the human FEN-1 gene, a human FEN-1 cDNA under transcriptional control of a mouse FEN-1 transcriptional regulatory region (e.g., at least 3–5 kb of 5' flanking sequence upstream of the mouse FEN-1 transcription start site.

In an embodiment, the invention provides FEN-1 polynucleotides for gene therapy and compositions of such FEN-1 gene therapy vectors for treating or preventing disease.

A further embodiment involves a polynucleotide (e.g., a DNA isolate) consisting essentially of a genomic DNA sequence encoding FEN-1 and more particularly a composition consisting of cDNA molecules which encode the human FEN-1 protein.

A further embodiment involves a polynucleotide (e.g., a DNA isolate) consisting essentially of a genomic DNA sequence encoding human FEN-1 and more particularly a composition consisting of cDNA molecules which encode the FEN-1 protein.

The invention also provides a novel diagnostic assay, comprising contacting a sample believed to potentially contain a predetermined target polynucleotide sequence (e.g., a target polynucleotide; analyte) with a probe polynucleotide capable of specific hybridization to all or a portion of said target polynucleotide under assay conditions, and forming as a result of the hybridization a 5' flap structure which can be cleaved by FEN-1 releasing nucleotides (or polynucleotides) in the flap strand; incubating with FEN-1 and detecting the release of nucleotides (or polynucleotides) of the flap strand, the release of nucleotides (or polynucleotides) thereby reporting the formation of a flap structure (or nicked DNA) and thereby reporting the presence, and optionally quantity, of the predetermined target polynucleotide sequence in the sample. Typically, the probe polynucleotide comprises two portions, a first portion which hybridizes to the target sequence and a second portion which is adjacent to said first portion and which forms the flap strand; frequently an adjacent polynucleotide is present which hybridizes to the portion of the target polynucleotide immediately 5' to the portion of the target which hybridizes to the probe polynucleotide sequence. The portion of the probe polynucleotide which forms the flap is typically labelled, and the entire probe may be labelled; in some embodiments, the target polynucleotide is 5'-end-labeled. Often, the probe polynucleotide is immobilized. The release of label in the presence of FEN-1 measures the abundance of target polynucleotide in the sample. For illustration and not limitation, with reference to FIG. 6, a probe may correspond to the flap strand, a target polynucleotide may correspond to the bridge strand ($F_{br}$), and an adjacent strand may correspond to the $F_{adj}$ strand, as shown. Alternatively, a probe polynucleotide, typically labelled, may be immobilized via its 5' end such that hybridization to the target polynucleotide will form a cleavable flap which can be cleaved by FEN-1 releasing the cleaved portion of the probe polynucleotide which is hybridized to the target; quantitating the amount of released label thereby detects the amount of target polynucleotide in the sample. The formation of the flap structure can also result from mismatch between the probe and the target, thus probes are mismatched to the target can form flaps which are cleaved by FEN-1, thereby serving to detect mismatches such as those indicating point mutants, small deletion or addition mutants, small inversion mutants, and the like, so long as the hybridization of the probe to the target generates a cleavable flap due to the sequence mismatch.

A further understanding of the nature and advantages of the invention will become apparent by reference to the remaining portions of the specification and drawings.

BRIEF DESCRIPTION OF THE DRAWINGS

FIG. 1. Sequence of human FEN-1. Panel A: predicted amino acid sequence of human FEN-1. Panel B: Nucleotide sequence of coding portion of human FEN-1 cDNA.

FIG. 2. Sequence of mouse FEN-1. Panel A: predicted amino acid sequence of mouse FEN-1. Panel B: Nucleotide sequence of coding portion of mouse FEN-1 cDNA.

FIG. 3. Sequence of Saccharomyces FEN-1. Panel A: predicted amino acid sequence of yeast FEN-1. Panel B: Nucleotide sequence of coding portion of yeast FEN-1 cDNA.

FIG. 4. Sequence of Saccharomyces ΔRAD2. Panel A: amino acid sequence of yeast ΔRAD2. Panel B: Nucleotide sequence of coding portion of yeast ΔRAD2 DNA.

FIG. 5. Sequence and deduced an amino acid sequence of complete human FEN-1 cDNA, including untranslated portion.

DESCRIPTION OF THE PREFERRED EMBODIMENTS

Figure 6:
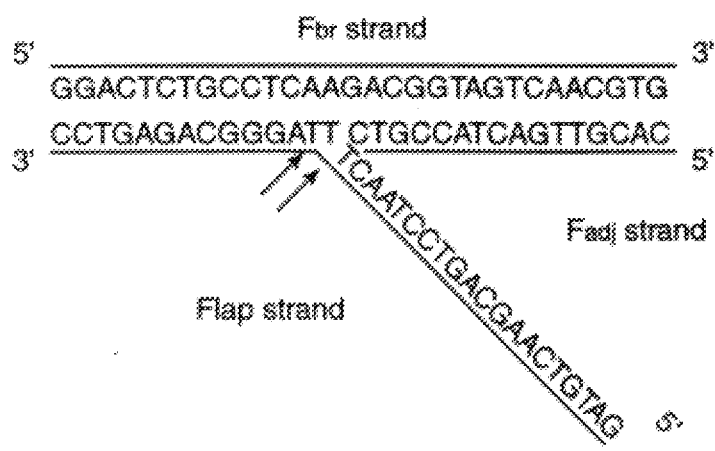
FIG. 6. DNA substrate for the flap cleavage. Nucleotide sequence for each of the three oligonucleotides which make up Flap Substrate 1 is shown. The flap strand (HJ42) was 5' end-labeled and annealed to the $F_{br}$ (HJ41) and $F_{adj}$ (HJ43) strands as described. The solid lines above and below this structure are shown to illustrate continuous strands. Following incubation of Flap Substrate 1 with protein extract, the reaction products are separated form the 34 nt input on a denaturing polyacrylamide gel. If cutting occurs at the elbow, for example, a 20 nt labeled fragment would be observed. Cutting proximal (hatched arrow) or distal (solid arrow) to the elbow would result in longer or shorter labeled products, respectively.
Figure 7:
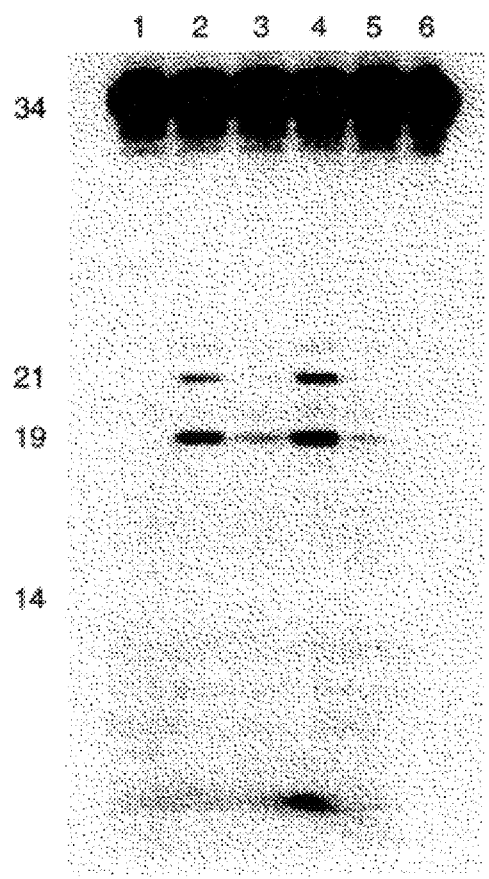
FIG. 7. Identification of flap endonucleolytic cleavage activity in mouse lymphocytes and fibroblasts. Flap Substrate (FIG. 6) was incubated with varying amounts of nuclear extract in the presence of 0.5 µg sonicated salmon sperm DNA under standard FEN-1 endonuclease assay conditions as described. Lane 1, no extract; lanes 2 and 3, 40 ng and 10 ng 1–8 pre-B nuclear extract, respectively; lanes 4–6, 160 ng, 40 ng and 10 ng NIH3T3 fibroblast nuclear extract, respectively. Reaction products were separated on a 10% denaturing polyacrylamide gel and visualized by autoradiography. The numbers on the left indicate the position and size of oligonucleotide standards.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

Definitions

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

As used herein, the term "FEN-1" generally refers to the mammalian FEN-1 gene and mammalian FEN-1 proteins, including isoforms thereof, unless otherwise identified; human and murine FEN-1 proteins and genes are preferred exemplifications of mammalian FEN-1, and in its narrowest usage FEN-1 refers to a FEN-1 polynucleotide and polypeptide sequences having substantial identity to SEQ ID NO: 2 or 4, or is at least 85 percent substantially identical to SEQ ID NO: 2 or 4, or is at least 89–95 percent substantially identical to SEQ ID NO: 2 or 4. The term FEN-1 can also refer to the yeast FEN-1 of FIG. 3, as well as to fragments and muteins.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1, FIG. 2, FIG. 3, FIG. 4, or FIG. 5 or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence over a comparison window of at least 20 nucleotide positions, frequently over a window of at least 30–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length FEN-1 polynucleotide sequence shown in FIG. 1, FIG. 2, of FIG. 5, or a segment of a FEN-1 protein.

As applied to polypeptides, the term "substantial identity" means that two peptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "FEN-1 native protein" and "full-length FEN-1 protein" as used herein refers to a full-length FEN-1 polypeptide of 380 amino acids length consisting of SEQ ID NO: 1 or the 378 amino acid long polypeptide of SEQ ID NO: 3 or as naturally occurs in a mammalian species (e.g., mouse, human, simian, rat, etc.). A preferred FEN-1 native protein is the polypeptide corresponding to the deduced amino acid sequence shown in FIG. 1 (panel A) or FIG. 2 (panel A) or corresponding to the deduced amino acid sequence of a cognate full-length FEN-1 CDNA of another species. Also for example, a native FEN-1 protein present in naturally-occurring somatic cells which express the FEN-1 gene are considered full-length FEN-1 proteins.

The term "fragment" as used herein refers to a polypeptide that has an amino-terminal and/or carboxy-terminal deletion, but where the remaining amino acid sequence is identical to the corresponding positions in the sequence deduced from a full-length encoding cDNA sequence (e.g., the cDNA sequence shown in FIGS. 1, 2, 3, or 5). Fragments typically are at least 14 amino acids long, preferably at least 20 amino acids long, usually at least 50 amino acids long or longer, up to the length of a full-length naturally-occurring FEN-1 polypeptide (e.g., about 378–380 amino acids).

The term "analog", "mutein" or "mutant" as used herein refers to polypeptides which are comprised of a segment of at least 10 amino acids that has substantial identity to a portion of the naturally occurring protein. For example, a FEN-1 analog comprises a segment of at least 10 amino acids that has substantial identity to a FEN-1 protein, such as the FEN-1 protein of FIG. 1 (panel A) or FIG. 2 (panel A); preferably a deduced amino acid sequence of a mammalian FEN-1 cDNA. In an embodiment, a FEN-1 analog or mutein has at least one of the following properties: binding to a 5' DNA flap substrate and/or cleaving a 5' DNA flap substrate under suitable binding conditions. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring protein (e.g., 378–380 amino acid residues for mouse and human FEN-1). Some analogs may lack biological activity (e.g., DNA 5' flap substrate binding or cleavage) but may still be employed for various uses, such as for raising antibodies to FEN-1 epitopes, as an immunological reagent to detect and/or purify α-FEN-1 antibodies by affinity chromatography, or as a competitive or noncompetitive agonist, antagonist, or partial agonist of native FEN-1 protein function.

The term "FEN-1 polypeptide" is used herein as a generic term to refer to native protein, fragments, or analogs of FEN-1, or such fused to a second polypeptide sequence (e.g., an epitope tag, β-gal, or other fusion). Hence, native FEN-1, fragments of FEN-1, and analogs of FEN-1, as well as FEN-1 fusion proteins are species of the FEN-1 polypeptide genus. Preferred FEN-1 polypeptides include: a murine full-length FEN-1 protein comprising the murine polypeptide sequence shown in FIG. 2 (panel A), a full-length human FEN-1 protein comprising a polypeptide sequence encoded by a human FEN-1 cDNA of FIG. 1 (panel A), polypeptides consisting essentially of the sequence of FEN-1, and the naturally-occurring mouse and human FEN-1 isoforms, including post-translationally modified isoforms. Generally, FEN-1 polypeptides are less than 5,000 amino acids long, usually less than 1000 amino acids long, often 380 amino acids long or less.

The term "FEN-1 polynucleotide" as used herein refers to a polynucleotide of at least 20 nucleotides wherein the polynucleotide comprises a segment of at least 20 nucleotides which: (1) are at least 85 percent identical to a naturally-occurring FEN-1 mRNA sequence or its complement or to a naturally-occurring FEN-1 genomic structural gene sequence, and/or (2) encode a FEN-1 polypeptide. Due to the degeneracy of the genetic code, some FEN-1 polynucleotides encoding a FEN-1 polypeptide will be less that 85 percent identical to a naturally-occurring FEN-1 polynucleotide. Similarly, some FEN-1 polynucleotides which are suitable as hybridization probes, PCR primers, LCR amplimers, and the like will not encode a FEN-1 polypeptide.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate human gene to the murine FEN-1 gene is the human gene which encodes an expressed protein which has the greatest degree of sequence identity to the murine FEN-1 protein and which exhibits an expression pattern similar to that of the murine FEN-1 (e.g., expressed in an equivalent tissue-specific expression pattern). Preferred cognate FEN-1 genes are: rat FEN-1, rabbit FEN-1, canine FEN-1, nonhuman primate FEN-1, porcine FEN-1, bovine FEN-1, and hamster FEN-1. Cognate genes to FEN-1 in non-mammalian species (e.g., *C. elegans,* avians, fish) can also be isolated.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "antineoplastic agent" is used herein to refer to agents that have the functional property of inhibiting a development or progression of a neoplasm in a human, particularly a lymphocytic leukemia, lymphoma or pre-leukemic condition.

The term "FEN-1 antagonist" is used herein to refer to agents which inhibit FEN-1 activity and can produce a cell phenotype characteristic of cells having reduced or undetectable expression of FEN-1; FEN-1 antagonists typically will enhance cell death, especially in the presence of DNA-damaging agents. In contradistinction, FEN-1 agonists will enhance FEN-1 activity.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

An "isolated" polynucleotide or polypeptide is a polynucleotide or polypeptide which is substantially separated from other contaminants that naturally accompany it, e.g., protein, lipids, and other polynucleotide sequences. The term embraces polynucleotide sequences which have been removed or purified from their naturally-occurring environment or clone library, and include recombinant or cloned DNA isolates and chemically synthesized analogues or analogues biologically synthesized by heterologous systems.

As used herein the terms "pathognomonic concentration", "pathognomonic amount", and "pathognomonic staining pattern" refer to a concentration, amount, or localization pattern, respectively, of a FEN-1 protein or mRNA in a sample, that indicates the presence of a pathological (e.g., neoplastic, senescent, immunodeficient, neurodegenerative, inflammatory, etc.) condition or a predisposition to developing a neoplastic disease, such as carcinoma, sarcoma, or leukemia. A pathognomonic amount is an amount of a FEN-1 protein or FEN-1 mRNA in a cell or cellular sample that falls outside the range of normal clinical values that is established by prospective and/or retrospective statistical clinical studies. Generally, an individual having a neoplastic disease (e.g., carcinoma, sarcoma, or leukemia) will exhibit an amount of FEN-1 protein or mRNA in a cell or tissue sample that is outside the range of concentrations that characterize normal, undiseased individuals; typically the pathognomonic concentration is at least about one standard deviation outside the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20°–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

As used herein, the terms "interacting polypeptide segment" and "interacting polypeptide sequence" refer to a portion of a hybrid protein which can form a specific binding interaction with a portion of a second hybrid protein under suitable binding conditions. Generally, a portion of the first hybrid protein preferentially binds to a portion of the second hybrid protein forming a heterodimer or higher order heteromultimer comprising the first and second hybrid proteins; the binding portions of each hybrid protein are termed interacting polypeptide segments. Generally, interacting polypeptides can form heterodimers with a dissociation constant ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$ or more, under suitable physiological conditions.

The term "recombinant" used herein refers to FEN-1 polypeptides produced by recombinant DNA techniques wherein the gene coding for protein is cloned by known recombinant DNA technology. For example, the human gene for FEN-1 may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host.

Overview

Deoxyribonucleases play a role in many repair processes since they enable the excision of damaged DNA and provide a means for heteroduplex formation and processing in recombination. Several deoxyribonucleases have been shown both genetically and biochemically to function in recombination and repair.

Nucleotide excision repair (NER) is a major pathway by which damaged nucleotides are removed from DNA. The biochemical steps leading to the repair of damaged DNA bases include recognition of damage, incision and removal of the damaged strand, DNA synthesis to replace the excised nucleotides, and ligation. Current models involve specific branched DNA structures at the site of damage. The resulting branched DNA structures may then be cleaved by the single-stranded endonucleases, such as RAD2 or RAD 1/10 in Saccharomyces.

The design of branched DNA structures similar to those hypothesized in NER have allowed the purification in a mammalian DNA structure-specific endonuclease. This enzyme, called Flap endonuclease-1 or FEN-1, cleaves DNA flap strands that terminate with 5' single-stranded ends (see structure in FIG. 6). DNA flap substrate 1 was designed to detect structure-specific endonucleases in mammalian cells, (FIG. 6). This substrate is a 5' flap structure because the flap strand terminates with a 5' single-stranded end. Conversely, 3' flap structures have a flap strand that terminates with a 3' single-stranded end. Both 5' and 3' flap structures are composed of a flap strand, an $F_{br}$ (bridge) strand, and an $F_{adj}$ (adjacent) strand.

FEN-1 cleavage is flap strand specific and independent of flap strand length. Other branched DNA structures, including Holliday junctions, are not cleaved by FEN-1. In addition to endonuclease activity, FEN-1 has a 5'-3' exonuclease activity that is specific for double-stranded DNA. The preferred cut sites of FEN-1 are located 1 nucleotide proximal (hatched arrow) and 1 nucleotide distal (solid arrow) to the elbow of the flap strand. FEN-1 specifically cleaves 5' flap structures and nicked DNA but not 3' flap structures. Cleavage of flap substrate 1 occurs primarily at 1 nucleotide proximal and 1 nucleotide distal to the elbow of the flap strand. Other 5' flap structures, however, are cleaved by FEN-1 primarily at 1 nucleotide proximal to the flap strand elbow. On the basis of these activities FEN-1 is believed to be involved in replicative and repair DNA synthesis through a nick translation mechanism.

Nick-translation, the concerted action of DNA polymerization and degradation of an upstream primer, is an important reaction in DNA replication and repair. In *E. coli,* nick-translation is carried out by DNA polymerase I (Pol I). This complex enzyme is made up of a polymerase domain, a 3'–5' exonuclease proof-reading domain, and a 5'-3' exonuclease domain. Mutation of the 5'-3' exonuclease domain results in the inability of Pol I to carry out nick-translation. In vivo, this is manifested as a loss of cell viability due to the inability to remove the RNA primers on Okazaki fragments. Recently, the 5'-3' exonuclease domain of Pol I has been shown to have a structure-specific endonuclease domain that cleaves a branched DNA structure called a DNA flap (Lyamichev et al. 1993). This endonuclease activity may be important for the removal of some types of DNA damage.

In eukaryotic cells, DNA polymerases do not have an intrinsic 5'-3' exonuclease domain. Nick-translation activity may be achieved by a 5'-3' exonuclease that interacts with a DNA polymerase through protein-protein interactions.

Nonhomologous recombination is a broad term used to describe a variety of DNA recombination reactions in which little or no sequence homology is used. Examples include chromosomal translocations, movements of retroviruses and transposable elements, developmental rearrangements of antibody and T-cell receptor genes, and gene amplification. The products from these recombination events are the result of DNA breakage followed by DNA end-joining. Random DNA breakage can occur as a result of a variety of metabolic processes or by exogenous factors such as X-irradiation. Following breakage, DNA ends are joined very efficiently by mammalian cells. Virtually any two ends, regardless of sequence or configuration, can be joined in the cell. Mammalian cells have mechanisms which modify DNA ends, allowing them to be joined.

DNA sequence analysis of end-joining products indicates that DNA ends can be modified and joined in a variety of ways. One important finding from these studies is that a major faction of end-joining events utilize short terminal homologies of 1–5 nucleotides (nt) in the resolution of DNA ends.

Homology at DNA termini has also been implicated in the joining of codings ends during V(D)J recombination. V(D)J recombination is a site-specific recombination system in mammalian cells which directs the rearrangement of the antigen receptors of the immune system. This reaction is initiated by a site-specific recombinase which introduces double-stranded breaks at the recombination signal sequences. As in general DNA end-joining, the presence of homology is not required for joining to occur.

In the template-directed ligation and post-repair ligation models of DNA end-joining, base-pairing of several terminal nucleotides can result in the formation of DNA flap structures. This structure may form as a result of limited exonuclease action at the DNA ends exposing single-stranded regions. Transient base-pairing of the exposed single-strands can then occur between the two ends. The resulting branched DNA structure, therefore, consists of both duplex DNA and unpaired displaced single-strands. In order to resolve this structure, the displaced single-strands must be removed before ligation can occur. It has not been clear, however, whether the displaced strands are removed endo- or exonucleolytically.

The present invention provides FEN-1, a FLAP endonuclease involved in DNA repair, recombination, and replication involving DNA flap intermediates or DNA:RNA flap intermediates.

General Methods

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications,* eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

Also incorporated herein by reference are: Harrington and Lieber (1994) *Genes and Development* 8: 1344; Harrington and Lieber (1994) *The EMBO J.* 13: 1235; Hiraoka et al. (1995) *Genomics* 25: 220; and Harrington and Lieber (1995) *J. Biol. Chem.* 270.

FEN-1 Polypeptides and Polynucleotides

Cloning of FEN-1 Polynucleotides

Disclosure of the full coding sequences for mammalian FEN-1 shown in FIG. 1 and FIG. 2 makes possible the construction of isolated polynucleotides that can direct the expression of FEN-1, fragments thereof, or analogs thereof. Further, the sequences in FIG. 1, FIG. 2, and FIG. 5 make possible the construction of nucleic acid hybridization probes and PCR primers that can be used to detect RNA and DNA sequences encoding FEN-1.

Polynucleotides encoding full-length FEN-1 or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a FEN-1 polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

Preferably, these amino acid sequences occur in the given order (in the amino-terminal to carboxy-terminal orientation) and may comprise other intervening and/or terminal sequences; generally such polypeptides are less than 1000 amino acids in length, more usually less than about 500 amino acids in lengths, and frequently approximately 204 amino acids in length. The degeneracy of the genetic code gives a finite set of polynucleotide sequences encoding these amino acid sequences; this set of degenerate sequences may be readily generated by hand or by computer using commercially available software (Wisconsin Genetics Software Package Relaes 7.0). Isolated FEN-1 polynucleotides typically are less than approximately 10,000 nucleotides in length.

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting FEN-1 RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to a FEN-1 sequence is retained.

Genomic or CDNA clones encoding FEN-1 may be isolated from clone libraries (e.g., available from Clontech, Palo Alto, Calif.) using hybridization probes designed on the basis of the nucleotide sequences shown in FIG. 1 and FIG. 2 and FIG. 5 and using conventional hybridization screening methods (e.g., Benton W D and Davis R W (1977) *Science* 196: 180; Goodspeed et al. (1989) *Gene* 76: 1). Where a CDNA clone is desired, clone libraries containing cDNA derived from somatic cell mRNA or other FEN-1-expressing cell mRNA are preferred. Alternatively, synthetic polynucleotide sequences corresponding to all or part of the sequences shown in FIG. 1, FIG. 2 and FIG. 5 may be constructed by chemical synthesis of oligonucleotides. Additionally, polymerase chain reaction (PCR) using primers based on the sequence data disclosed in FIG. 1 and FIG. 2 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 or 2 and a second primer that is not based on that sequence data may be used. For example, a second primer that is homologous to or complementary to a polyadenylation segment may be used.

Provided in the invention are polynucleotides comprising a segment encoding a FEN-1 epitope or a multiplicity of FEN-1 epitopes. Preferred human FEN-1 epitopes are:
—IQGLAKLIADVAPSAIRENDIK— (SEQ ID NO: 16);
—SMSIYQFLIAVRQGGD— (SEQ ID NO: 17);
—TSHLMGMFYRTIRMMENGIKPV— (SEQ ID NO: 18); —GKPPQLKSGELAKRSERRAEAEKQ— (SEQ ID NO: 19);
—EQEVEKFTKRLVKVTKQHND— (SEQ ID NO: 20); —LLSLMGIPYLDAPSEAEASCAALVK— (SEQ ID NO: 21);
—LTFGSPVLMRHLTASEAKKLPIQ— (SEQ ID NO: 22); —ILQELGLNQEQFVDLCILLGS— (SEQ ID NO: 23);
—RGIGPKRAVDLIQKHKSIEEIVRR— (SEQ ID NO: 24); —PENWLHKEAHQLFLEPEVLD— (SEQ ID NO: 25);
—WSEPNEEELIKFMCGEKQFSEE— (SEQ ID NO: 26); —SKSRQGSTQGRLDDFFKVTGSL— (SEQ ID NO: 27);
and —KEPEPKGSTKKKAKTG— (SEQ ID NO: 28).
Polynucleotides encoding epitopes having substantial identity to these preferred epitopes are often employed. Such polynucleotides have a variety of uses, including as FEN-1 probes, as templates for producing polypeptides comprising a FEN-1 epitope whereby such proteins are FEN-1 immunogens or commercial diagnostic reagents for standardizing a FEN-1 immunoassay, as polynucleotide vaccines (immunogens) when fused to a secretory sequence for administering to an animal and making α-FEN-1 antisera and hybridomas; such polynucleotides can also be used as foodstuffs, combustible energy sources, and viscosity-enhancing solutes.

Isolation of the Cognate FEN-1 Genes

Mammalian homologs of the human and murine FEN-1 gene or cDNA is identified and isolated by screening a human genomic or cDNA clone library, such as a human, rat, rabbit, or other genomic or cDNA library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIG. 1 (B) or FIG. 2 (B). Typically, hybridization and washing conditions are performed at high stringency according to conventional hybridization procedures. Positive clones are isolated and sequenced. For illustration and not for limitation, a full-length polynucleotide corresponding to the sequence of FIG. 1 (B) or FIG. 2 (B) may be labeled and used as a hybridization probe to isolate genomic clones from a human or murine genomic clone library in λEMBL4 or λGEM11 (Promega Corporation, Madison, Wis.); typical hybridization conditions for screening plaque lifts (Benton and Davis (1978) *Science* 196: 180) can be: 50% formamide, 5×SSC or SSPE, 1–5×Denhardt's solution, 0.1–1% SDS, 100–200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C.–37° C. for about 6–36 hours. Prehybridization conditions are essentially identical except that probe is not included and incubation time is typically reduced. Washing conditions are typically 1–3×SSC, 0.1–1% SDS, 50°–70° C. with change of wash solution at about 5–30 minutes. For isolating human FEN-1 polynucleotides with a mouse or human FEN-1 polynucleotide probe, it is often preferred to hybridize at approximately 39° C. and to wash sequentially at the following step temperatures: room temperature, 37° C., 39° C., 42° C., 45° C., 50° C., 55° C., 60° C., 65° C., and 70° C., stopping after each step and monitoring the background probe signal (and optionally detecting signal by autoradiogram and/or phosphor imaging, if radiolabeled probe is used) and terminating the washing steps when suitable signal/noise ratio is achieved, as determined empirically.

Human and other mammalian FEN-1 cDNAs and genomic clones (i.e., cognate nonhuman genes) can be analogously isolated from various nonhuman cDNA and genomic clone libraries available in the art (e.g., Clontech, Palo Alto, Calif.) by using probes based on the sequences shown in FIG. 1 (B) or FIG. 2 (B), with hybridization and washing conditions typically being less stringent than for isolation of FEN-1 human or mouse clones.

Polynucleotides comprising sequences of approximately at least 30–50 nucleotides, preferably at least 100 nucleotides, corresponding to or complementary to the nucleotide sequences shown in FIG. 1 (B) or FIG. 2(B) can serve as PCR primers and/or hybridization probes for identifying and isolating germline genes corresponding to FEN-1. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 1 (B) or FIG. 2 (B). Human genomic libraries are publicly available or may be constructed de novo from human DNA.

It is apparent to one of skill in the art that nucleotide substitutions, deletions, and additions may be incorporated into the polynucleotides of the invention. Nucleotide sequence variation may result from sequence polymorphisms of various FEN-1 alleles, minor sequencing errors, and the like. However, such nucleotide substitutions, deletions, and additions should not substantially disrupt the ability of the polynucleotide to hybridize to one of the polynucleotide sequences shown in FIG. 1 (B) or FIG. 2(B) under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 1 (B) or FIG. 2(B), wherein the probe preferentially hybridizes to the specific target such that, for example, a single band corresponding to one or more of the RNA species of FEN-1 (or alternatively spliced MRNA species) can be identified on a Northern blot of RNA prepared from a suitable cell source (e.g., a somatic cell expressing FEN-1). Polynucleotides of the invention and recombinantly produced FEN-1, and fragments or analogs thereof, may be prepared on the basis of the sequence data provided in FIG. 1 (B) and FIG. 2 (B) and FIG. 5) according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

FEN-1 polynucleotides may be short oligonucleotides (e.g., 20–100 bases long), such as for use as hybridization probes and PCR (or LCR) primers. FEN-1 polynucleotide sequences may also comprise part of a larger polynucleotide (e.g., a cloning vector comprising a FEN-1 clone) and may be fused, by polynucleotide linkage, in frame with another polynucleotide sequence encoding a different protein (e.g., glutathione S-transferase or β-galactosidase) for encoding expression of a fusion protein. Typically, FEN-1d polynucleotides comprise at least 25 consecutive nucleotides which are substantially identical to a naturally-occurring FEN-1 sequence (e.g., FIGS. 1 or 2), more usually FEN-1 polynucleotides comprise at least 50 to 100 consecutive nucleotides which are substantially identical to a naturally-occurring FEN-1 sequence. However, it will be recognized by those of skill that the minimum length of a FEN-1 polynucleotide required for specific hybridization to a FEN-1 target sequence will depend on several factors: G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothiolate, etc.), among others.

If desired, PCR amplimers for amplifying substantially full-length cDNA copies may be selected at the discretion of the practitioner. Similarly, amplimers to amplify single FEN-1 exons or portions of the FEN-1 gene (murine or human) may be selected.

Each of these sequences may be used as hybridization probes or PCR amplimers to detect the presence of FEN-1 mRNA, for example to diagnose a neoplastic disease characterized by the presence of an elevated or reduced FEN-1 mRNA level in cells, or to perform tissue typing (i.e., identify tissues characterized by the expression of FEN-1 mRNA), and the like. The sequences may also be used for detecting genomic FEN-1 gene sequences in a DNA sample, such as for forensic DNA analysis (e.g., by RFLP analysis, PCR product length(s) distribution, etc.) or for diagnosis of diseases characterized by amplification and/or rearrangements of the FEN-1 gene. Alternatively, FEN-1 polynucleotides can be used as a foodstuff, combustible energy source, viscosity-enhancing solute, and the like. In a variation of the invention, polynucleotides of the invention are employed for diagnosis of pathological conditions or genetic disease that involve neoplasia of other medical conditions related to FEN-1 function, and more specifically conditions and diseases that involve alterations in the structure or abundance of a FEN-1 polypeptide.

For example and not limitation, the following pair of oligonucleotide primers can be used to amplify FEN-1 polynucleotide sequences (e.g., CDNA) or as hybridization probes (e.g., as biotinylated or end-labeled oligonucleotide probes):

5'-ATGGGAATTCAAGGCCTGGCCAAACT-3' (SEQ ID NO: 14) and
5'-TTTATTTTCCCCTTTTAAACTTCCCTGC-3' (SEQ ID NO: 15). Other suitable PCR primers, LCR primers, hybridization probes, exon-specific hybridization probes and primers, degenerate oligonucleotides encoding FEN-1 polypeptide sequences, and the like are apparent to those of skill in the art in view of FIG. 1, FIG. 2 and FIG. 5, and other FEN-1 sequences which can be obtained therewith.

For example and not limitation, a FEN-1 polynucleotide can comprise the sequence:
5'-ATGGGAATTCAAGGCCTGGCCAAACTAATTGCTGATGTGGCCCCAGTGCCATCCGGGAGA ATGACATCAAGAGCTACTTTGGCCGTAAGGTGGCCATTGATGCCTCTATGAGCATTTATCAGTTCCTGATTGCTGTTCGCCAGGGTGGGGATGTGCTGCAGAATGAGGAGGGTGAGACCACC AGCCACCTGATGGGCATGTTCTACCGCACCATTCGCATGATGGAGAACGGCATCAAGCCCG TGTATGTCTTTGATGGCAAGCCGCCA-CAGCTCAAGTCAGGCGAGCTGGC-CAAACGCAGTGA GCGGCGGGCTGAGGCAG-AGAAGCAGCTGCAGCAGGCTCAGGCT-GCTGGGGCCGAGCAGGAG GTGGAAAAATTCAC-TAAGCGGCTGGTGAAGGTCACTAAGCAG-CACAATGATGAGTGCAAAC ATCTGCTGAGCCTCATGGGCATCCCT-TATCTTGATGCACCCAGTGAGGCAGAG-GCCAGCTG TGCTGCCCTGGTGAAGGCTGGCA-AAGTCTATGCTGCGGCTACCGAGGA-CATGGACTGCCTC ACCTTCGGCAGCCCTGT-GCTAATGCGACACCTGACTGCCAGT-GAAGCCAAAAAGCTGCCAA TCCAGGAATTCCACCTGAGCCGGATTCT-GCAGGAGCTGGGCCTGAACCAGGAACAGTTTGT GGATCTGTGCATCCTGCTAGGCAGTGAC-TACTGTGAGAGTATCCGGGGTATTGGGCCCAAG CGGGCTGTGGACCTCATCCAGAAGCA-CAAGAGCATCGAGGAGATCGTGCGGC-GACTTGACC CCAACAAGTACCCTGTGCC-AGAAAATTGGCTCCACAAGGAGGCTCAC-CAGCTCTTCTTGGA ACCTGAGGTGCTGGACCCA-GAGTCTGTGGAGCTGAAGTGGAGCGAGC-CAAATGAAGAAGAG CTGATCAAGTTCATGTGTGGTGAAAAG-CAGTTCTCTGAGGAGCGAATCCG-CAGTGGGGTCA AGAGGCTGAGTAAGAGC-CGCCAAGGCAGCACCCAGGGCCGCCTG-GATGATTTCTTCAAGGT GACCGGCTCACTCTCT-TCAGCTAAGCGCAAGGAGCCAGAAC-CCAAGGGATCCACTAAGAAG AAGGCAAAGACTGGG-GCAGCAGGGAAGTTTAAAAGGGGAAAATAAA-3' (SEQ ID NO: 29)

Also for example and not limitation, a FEN-1 polynucleotide can comprise one or more sequences selected from the group consisting of:
5'-TGGGAATTCAAGGCCTGGCCAAACTAATTGCTGATGTGGCCCCCA-3' (SEQ ID NO: 30);
5'-TGACATCAAGAGCTACTTTGGCCGTAAGGTGGCCA-3' (SEQ ID NO: 31);
5'-TGCCTCTATGAGCATTTATCAGTTCCTGATTGCTGTT-3' (SEQ ID NO: 32);
5'-GGATGTGCTGCAGAATGAGGAGGGTGAGACCAC-3' (SEQ ID NO: 33);
5'-TGGGCATGTTCTACCGCACCATTCGCATGATGGAGAACG-3' (SEQ ID NO: 34);
5'-CTTTGATGGCAAGCCGCCACAGCTCAAGTCAGGCGAGCTGG-3' (SEQ ID NO: 35);
5'-AGCAGCTGCAGCAGGCTCAGGCTGCTGGGGCC-3' (SEQ ID NO: 36);
5'-AATTCACTAAGCGGCTGGTGAAGGTCACTAAGCAG-3' (SEQ ID NO: 37);
5'-ATGATGAGTGCAAACATCTGCTGAGCCTCATG-3' (SEQ ID NO: 38);
5'-ATCCCTTATCTTGATGCACCCAGTGAGGCAGAGGCCA-3' (SEQ ID NO: 39);
5'-GCCCTGGTGAAGGCTGGCAAAGTCTATGCTGCGGCTACCGAGGA-3' (SEQ ID NO: 40);
5'-CTTCGGCAGCCCTGTGCTAATGCGACACCTGAC-3' (SEQ ID NO: 41);
5'-CAGGAATTCCACCTGAGCCGGATTCTGCAGGAGCTG-3' (SEQ ID NO: 42);
5'-CCTGAACCAGGAACAGTTTGTGGATCTGTGCATCCT-3' (SEQ ID NO: 43);
5'-AGGCAGTGACTACTGTGAGAGTATCCGGGGTATTGGGCCCA-3' (SEQ ID NO: 44);
5'-GGCTGTGGACCTCATCCAGAAGCACAAGAGCATCGAGGA-3' (SEQ ID NO: 45);
5'-CAAGTACCCTGTGCCAGAAAATTGGCTCCACAAGGAGGCT-3' (SEQ ID NO: 46);
5'-CTGAGGTGCTGGACCCAGAGTCTGTGGAGCTGAAGTGG-3' (SEQ ID NO: 47);
5'-GATCAAGTTCATGTGTGGTGAAAAGCAGTTCTCTGAGGAGC-3' (SEQ ID NO: 48);
5'-ATCCGCAGTGGGGTCAAGAGGCTGAGTAAGAGCCGCCA-3' (SEQ ID NO: 49);
5'-GCAGCACCCAGGGCCGCCTGGATGATTTCTTC-3' (SEQ ID NO: 50);
5'-CGGCTCACTCTCTTCAGCTAAGCGCAAGGAGCCA-3' (SEQ ID NO: 51);
5'-CCCAAGGGATCCACTAAGAAGAAGGCAAAGACTGGGGCAGC-3' (SEQ ID NO: 52).

A preferred FEN-1 polynucleotide comprises all of these sequences in the given order, with or without spacer polynucleotides between the given sequences. Non-coding sequences of a FEN-1 polynucleotide, such as provided in FIG. 1 or FIG. 2, or equivalent non-mouse, non-human FEN-1 polynucleotide, can also be used.

For example and not limitation, a FEN-1 polynucleotide can comprise the nucleotide sequence shown in FIG. 1 (SEQ ID NO: 2) or FIG. 2 (SEQ ID NO: 4).

For example, a FEN-1 cDNA and/or genomic clone can be identified and isolated from a cDNA or genomic library, respectively, by hybridization of a labeled probe comprising the polynucleotide sequence of FIG. 1 (B) and/or FIG. 2 (B) or a pool of degenerate oligonucleotides encoding a segment of the polynucleotide sequence shown in FIG. 1 (A) or FIG. 2 (A). Suitable hybridization conditions for specific hybridization of these labeled probes to the mammalian FEN-1 cDNA or gene can be established empirically by performing a series of hybridizations and/or washing steps at several temperatures and/or ionic strength conditions; for example and not limitation, hybridization conditions comprising 50% formamide, 5×SSC or SSPE, 1–5×Denhardt's solution, 0.1–1% SDS, 100–200 $\mu$g sheared heterologous DNA or tRNA, 0–10% dextran sulfate, $1\times10^5$ to $1\times10^7$ cpm/ml of denatured probe with a specific activity of about $1\times10^8$ cpm/$\mu$g, and incubation at 42° C.-37° C. for about 6–36 hours is often a suitable initial point.

Antisense Polynucleotides

Additional embodiments directed to modulation of neoplasia or cell death include methods that employ specific antisense polynucleotides complementary to all or part of the sequences shown in FIG. 1 (B) or FIG. 2 (B) or a cognate mammalian FEN-1 sequence. Such complementary antisense polynucleotides may include nucleotide substitutions, additions, deletions, or transpositions, so long as specific hybridization to the relevant target sequence corresponding to FIG. 1 (B) or FIG. 2(B) is retained as a functional property of the polynucleotide. Complementary antisense polynucleotides include soluble antisense RNA or DNA oligonucleotides which can hybridize specifically to FEN-1 mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of FEN-1 polypeptides. Antisense polynucleotides that prevent transcription and/or translation of mRNA corresponding to FEN-1 polypeptides may inhibit neoplasia, senescence, AIDS, and the like, and/or reverse the transformed phenotype of cells. Antisense polynucleotides of various lengths may be produced, although such antisense polynucleotides typically comprise a sequence of about at least 25 consecutive nucleotides which are substantially identical to a naturally-occurring FEN-1 polynucleotide sequence, and typically which are identical to a sequence shown in FIG. 1 (B), FIG. 2 (B), of FIG. 5 or a FEN-1 sequence disclosed herein.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific MRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

Transgenic Animal Embodiments

Genomic clones of FEN-1, particularly of the murine FEN-1 gene, may be used to construct homologous targeting constructs for generating cells and transgenic nonhuman animals having at least one functionally disrupted FEN-1 allele. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated FEN-1 allele. Such mice may be sold commercially as research animals for investigation of immune system development, neoplasia, spermatogenesis, may be used as pets, may be used for animal protein (foodstuff), and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a FEN-1 cDNA or genomic gene copy may be used to construct transgenes for expressing FEN-1 polypeptides at high levels and/or under the transcriptional control of transcription control sequences which do not naturally occur adjacent to the FEN-1 gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a FEN-1-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential carcinogens, as overexpression of FEN-1 or inappropriate expression of FEN-1 may result in a preneoplastic or neoplastic state.

Production of FEN-1 Polypeptides

The nucleotide and amino acid sequences shown in FIG. 1, FIG. 2, and FIG. 5 enable those of skill in the art to produce polypeptides corresponding to all or part of the full-length mammalian FEN-1 polypeptide sequences. Such polypeptides may be produced in prokaryotic or eukaryotic host cells by expression of polynucleotides encoding FEN-1, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of FEN-1 may be prepared by those of skill in the art. Preferred amino- and carboxy-termini of fragments or analogs of FEN-1 occur near boundaries of functional domains. For example, but not for limitation, such functional domains include domains conferring the property of binding to 5' DNA flap substrate and/or cleaving said flap substrate, and (2) conserved domains (e.g. an N-region, I-region, or C-region).

One method by which structural and functional domains may be identified is by comparison of the nucleotide and/or amino acid sequence data shown in FIGS. 1 and 2 to public or proprietary sequence databases. Preferably, computerized comparison methods are used to identify sequence motifs or predicted protein conformation domains that occur in other proteins of known structure and/or function. For example, the NAD-binding domains of dehydrogenases, particularly lactate dehydrogenase and malate dehydrogenase, are similar in conformation and have amino acid sequences that are detectably homologous (*Proteins, Structures and Molecular Principles,* (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the FEN-1 sequences of the invention.

Additionally, computerized comparison of sequences shown in FIG. 1 or FIG. 2 to existing sequence databases can identify sequence motifs and structural conformations found in other proteins or coding sequences that indicate similar domains of the FEN-1 protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a FEN-1 sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in FEN-1 polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the FEN-1 fragment. Alternatively, FEN-1 polypeptides wherein one or more functional domain have been deleted will exhibit a loss of the property normally conferred by the missing fragment.

By way of example and not limitation, the domain(s) conferring the property of binding to 5' DNA flap structures may be fused to β-galactosidase to produce a fusion protein that can bind an immobilized 5' DNA flap substrate in a binding reaction and which can enzymatically cleave the 5'-flap.

Although one class of preferred embodiments are fragments having amino- and/or carboxy-termini corresponding to amino acid positions near functional domains borders, alternative FEN-1 fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of FEN-1 can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native FEN-1 protein. However, FEN-1 analogs must comprise a segment of 25 amino acids that has substantial similarity to a portion of the amino acid sequences shown in FIG. 1 (B) or FIG. 2(B) or other mammalian FEN-1 proteins, respectively, and which has at least one of the requisite functional properties (i.e., binds and/or cleaves 5' flap DNA substrates). Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs. FEN-1 analogs include various muteins of a FEN-1 sequence other than the naturally-occurring peptide sequence. For example, single or multiple amino acid substitutions (preferably conservative amino acid substitutions) may be made in the naturally-occurring FEN-1 sequence.

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles,* (1984) Creighton (ed.), W. H. Freeman and Company, New York; *Introduction to Protein Structure,* (1991), C. Branden and J. Tooze, Garland Publishing, New York, N.Y.; and Thornton et al. (1991) *Nature* 354: 105; which are incorporated herein by reference).

Similarly, full-length FEN-1 polypeptides and fragments, analogs, and/or fusions thereof can be made by those of skill in the art from the available FEN-1 gene, cDNA, and protein sequences. U.S. Pat. No. 5,279,952 discloses a method for using PCR to generate mutations (e.g., deletions) and chimeric genes from known sequences.

Methods used to produce human or mouse FEN-1 polynucleotides and polypeptides can also be modified by those of skill in the art to produce non-human FEN-1 polypeptides. For example, a sequence of a yeast FEN-1 protein is shown in FIG. 3 (A). Similarly, full-length nonhuman FEN-1 polypeptides and fragments, analogs, and/or fusions thereof can be made by those of skill in the art from the nonhuman gene, cDNA, and protein sequences.

Fusion proteins of FEN-1 can be made, such as fusions with a GAL4 activation domain or DNA-binding domain, and the like.

Native FEN-1 proteins, fragments thereof, or analogs thereof can be used as reagents in binding assays to detect binding to 5' DNA flap substrates or endonucleolytic cleavage thereof, for identifying agents that interfere with FEN-1 function, said agents are thereby identified as candidate drugs which may be used, for example, to block DNA repair following radiation or chemotherapy, to inhibit DNA replication and cell replication, and/or to induce apoptosis (e.g., to treat lymphocytic leukemias, carcinomas, sarcomas, AIDS, neurodegenerative disease, senescence), and the like. FEN-1 is used in DNA flap binding reactions wherein one or more agents are added are performed in parallel with a control binding reaction that does not include an agent. Agents which inhibit the specific binding of FEN-1 to a DNA flap or cleavage thereof, as compared to a control reaction, are identified as candidate FEN-1-modulating drugs.

Peptidomimetics

In addition to FEN-1 polypeptides consisting only of naturally-occurring amino acids, FEN-1 peptidomimetics are also provided. For example, peptidomimetics can be suitable as drugs for competitive inhibition of endogenous FEN-1 function, such as to inhibit DNA repair or replication in neoplastic cells.

Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human FEN-1, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—$CH_2NH$—, $CH_2CH_2$—); Spatola, A. F. et al., *Life Sci* (1986) 38:1243–1249 (—$CH_2$—S); Hann, M. M.,*J Chem Soc Perkin Trans I* (1982) 307–314 (—CH=CH—, cis and trans); Almquist, R. G. et al., *J Med Chem* (1980) 23:1392–1398 (—$COCH_2$—); Jennings-White, C. et al., *Tetrahedron Lett* (1982) 23:2533 (—$COCH_2$—); Szelke, M. et al., European Appln. EP 45665 (1982) CA: 97:39405 (1982) (—$CH(OH)CH_2$—); Holladay, M. W. et al., *Tetrahedron Lett* (1983) 24:4401–4404 (—$C(OH)CH_2$—); and Hruby, V. J., *Life Sci* (1982) 31:189–199 (—$CH_2$—S—); each of which is incorporated herein by reference. A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide. Cyclic peptides comprising a sequence of human FEN-1 frequently are preferred.

Another embodiment involves the formation of FEN-1 mutants wherein the native protein or fragment has at least one amino acid deleted or replaced by another amino acid and the mutants exhibits altered biological activity from the native protein or fragment.

The amino acid sequences of FEN-1 polypeptides identified herein will enable those of skill in the art to produce polypeptides corresponding to FEN-1 peptide sequences and sequence variants thereof. Such polypeptides may be produced in prokaryotic or eukaryotic host cells by expression of polynucleotides encoding a FEN-1 peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins,* Wiley Publishing, which are incorporated herein by reference).

Peptides comprising a FEN-1 polypeptide sequence and peptidomimetics thereof can be produced, typically by direct chemical synthesis or recombinant expression, and used as agents to competitively inhibit endogenous FEN-1 activity. The peptides are frequently produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Such peptides or peptidomimetics may be used therapeutically to treat disease by altering the process of DNA repair, replication, or recombination in a cell population of a patient.

Production and Applications of α-FEN-1 Antibodies

Native FEN-1 proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual,* (1988) E. Harlow and D. Lane, Cold Spring Harbor Laboratory, Cold Spring Harbor, N.Y., which is incorporated herein by reference.

For example but not for limitation, a recombinantly produced fragment of FEN-1 can be injected into a mouse along with an adjuvant following immunization protocols known to those of skill in the art so as to generate an immune response. Typically, approximately at least 1–50 μg of a FEN-1 fragment or analog is used for the initial immunization, depending upon the length of the polypeptide. Alternatively or in combination with a recombinantly produced FEN-1 polypeptide, a chemically synthesized peptide having a FEN-1 sequence may be used as an immunogen to raise antibodies which bind a FEN-1 protein, such as the native FEN-1 polypeptide having the sequence shown essentially in FIG. 1 (A) or FIG. 2 (A), a native human FEN-1 polypeptide, a polypeptide comprising a FEN-1 epitope, or a FEN-1 fusion protein. Immunoglobulins which bind the recombinant fragment with a binding affinity of at least $1 \times 10^7$ $M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly-produced FEN-1 polypeptide (or chemically synthesized FEN-1 polypeptide) with an affinity of at least $1 \times 10^6$ $M^{-1}$. Animals other than mice and rats may be used to raise antibodies; for example, goats, rabbits, sheep, and chickens may also be employed to raise antibodies reactive with a FEN-1 protein. Transgenic mice having the capacity to produce substantially human antibodies also may be immunized and used for a source of α-FEN-1 antiserum and/or for making monoclonal-secreting hybridomas.

Bacteriophage antibody display libraries may also be screened for binding to a FEN-1 polypeptide, such as a full-length FEN-1 protein, a FEN-1 fragment, or a fusion protein comprising a FEN-1 polypeptide sequence comprising a FEN-1 epitope (generally at least 3–5 contiguous amino acids). Generally such FEN-1 peptides and the fusion protein portions consisting of FEN-1 sequences for screening antibody libraries comprise about at least 3 to 5 contiguous amino acids of FEN-1, frequently at least 7 contiguous amino acids of FEN-1, usually comprise at least 10 contiguous amino acids of FEN-1, and most usually comprise a FEN-1 sequence of at least 14 contiguous amino acids as shown in FIG. 1 (A) or FIG. 2 (A).

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a FEN-1 polypeptide that is immobilized (e.g., by covalent linkage to a chromatography resin to enrich for reactive phage by affinity chromatography) and/or labeled (e.g., to screen plaque or colony lifts).

FEN-1 polypeptides which are useful as immunogens, for diagnostic detection of α-FEN-1 antibodies in a sample, for diagnostic detection and quantitation of FEN-1 protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of FEN-1 as an antigen rather than using the entire native protein. More specifically, where the object is to identify immunocrossreactive polypeptides that comprise a particular structural moiety, such as a DNA flap-binding domain, it is preferable to use as an antigen a fragment corresponding to part or all of a commensurate structural domain in the FEN-1 protein. Production of recombinant or synthetic fragments having such defined amino- and carboxy-termini is provided by the FEN-1 sequences shown in FIG. 1 (A) and FIG. 2 (A).

If an antiserum is raised to a FEN-1 fusion polypeptide, such as a fusion protein comprising a FEN-1 immunogenic epitope fused to β-galactosidase or glutathione S-transferase, the antiserum is preferably preadsorbed with the non-FEN-1 fusion partner (e.g, β-galactosidase or glutathione S-transferase) to deplete the antiserum of antibodies that react (i.e., specifically bind to) the non-FEN-1 portion of the fusion protein that serves as the immunogen. Monoclonal or polyclonal antibodies which bind to the human and/or murine FEN-1 protein can be used to detect the presence of human or murine FEN-1 polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured FEN-1 epitopes and may be identified visually or by other optical means with a labeled second antibody or labeled *Staphylococcus aureus* protein A by methods known in the art.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel FEN-1 binding factors or FEN-1-related proteins. Such screening of cDNA expression libraries is well known in the art, and is further described in Young et al., *Proc. Natl. Acad. Sci. U.S.A.* 80:1194–1198 (1983), which is incorporated herein by reference) as well as other published sources. Another use of such antibodies is to identify and/or purify immunocrossreactive proteins that are structurally or evolutionarily related to the native FEN-1 protein or to the corresponding FEN-1 fragment (e.g., functional domain) used to generate the antibody. The anti-FEN-1 antibodies of the invention can be used to measure levels of FEN-1 protein in a cell or cell population, for example in a cell explant (e.g., lymphocyte sample) obtained from a patient. The anti-FEN-1 antibodies can be used to measure the corresponding protein level by various methods, including but not limited to: (1) standardized ELISA on cell extracts, (2) immunoprecipitation of cell extracts followed by polyacrylamide gel electrophoresis of the immunoprecipitated products and quantitative detection of the band(s) corresponding to FEN-1, and (3) in situ detection by immunohistochemical straining with the anti-FEN-1 antibodies and detection with a labeled second antibody. The measurement of the FEN-1 protein level in a cell or cell population is informative regarding the replicative status and/or DNA damage status of the cell or cell population.

Various other uses of such antibodies are to diagnose and/or stage leukemias or other neoplasms, and for therapeutic application (e.g., as cationized antibodies or by targeted liposomal delivery) to treat neoplasia, autoimmune disease, AIDS, and the like.

An antiserum which can be utilized for this purpose can be obtained by conventional procedures. One exemplary procedure involves the immunization of a mammal, such as rabbits, which induces the formation of polyclonal antibodies against FEN-1. Monoclonal antibodies are also being generated from already immunized hamsters. This antibody can be used to detect the presence and level of the FEN-1 protein.

It is also possible to use the proteins for the immunological detection of FEN-1 and associations thereof with standard assays as well as assays using markers, which are radioimmunoassays or enzyme immunoassays.

The detection and determination of FEN-1 has significant diagnostic importance. For example, the detection of proteins conferring DNA repair capacity or replication capability would be advantageous in cancer therapy and controlling hypertrophies, as well as staging the degree of genomic instability in dysplastic variants of aggressive neoplasms. The detection or determination of FEN-1 proteins will be beneficial in staging senescence and immunodeficiency disease, including HIV-I, II and III, and in neurodegenerative and ischemic cell death. Thus these FEN-1 proteins and their antibodies can be employed as a marker to monitor, check or detect the course of disease.

Identification and Isolation of Proteins That Bind FEN-1

Proteins that bind to FEN-1 are potentially important regulatory proteins. Such proteins may be targets for novel antineoplastic agents or anti-inflammatory agents, immunomodulatory agents, and the like. These proteins are referred to herein as accessory proteins. Accessory proteins may be isolated by various methods known in the art. For example and not limitation, such accessory proteins may be DNA polymerases, ADP-ribosyltransferases, purine/pyrimidine deglycosylases, and the like.

One preferred method of isolating accessory proteins is by contacting a FEN-1 polypeptide to an antibody that binds the FEN-1 polypeptide, and isolating resultant immune complexes. These immune complexes may contain accessory proteins bound to the FEN-1 polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to FEN-1 specifically. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a FEN-1 polypeptide may be constructed by oligonucleotide synthesis, placed in an expression vector, and expressed in a host cell.

Putative accessory proteins that bind FEN-1 complexes in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a FEN-1 polypeptide. For a general discussion of cross-linking, see Kunkel et al. (1981) *Mol. Cell. Biochem.* 34: 3, which is incorporated herein by reference. Preferably, the bifunctional crosslinking reagent will produce crosslinks which may be reversed under specific conditions after isolation of the crosslinked complex so as to facilitate isolation of the accessory protein from the FEN-1 polypeptide. Isolation of crosslinked complexes that include a FEN-1 polypeptide is preferably accomplished by binding an antibody that binds a FEN-1 polypeptide with an affinity of at least $1 \times 10^7$ $M^{-1}$ to a population of crosslinked complexes and recovering only those complexes that bind to the antibody with an affinity of at least $1 \times 10^7$ $M^{-1}$. Polypeptides that are crosslinked to a FEN-1 polypeptide are identified as accessory proteins.

Also, an expression library, such as a λgt11 cDNA expression library (Dunn et al. (1989) *J. Biol. Chem.* 264: 13057), can be screened with a labelled FEN-1 polypeptide to identify cDNAs encoding polypeptides which specifically bind to the FEN-1 polypeptide. For these procedures, cDNA libraries usually comprise mammalian cDNA populations, typically human, mouse, or rat, and may represent cDNA produced from RNA of one cell type, tissue, or organ and one or more developmental stage. Specific binding for screening cDNA expression libraries is usually provided by including one or more blocking agent (e.g., albumin, nonfat dry milk solids, etc.) prior to and/or concomitant with contacting the labeled FEN-1 polypeptide (and/or labeled anti-FEN-1 antibody).

Screening assays can be developed for identifying candidate antineoplastic agents as being agents which inhibit binding of FEN-1 to an accessory protein under suitable binding conditions.

Yeast Two-Hybrid Screening Assays

An approach to identifying polypeptide sequences which bind to a predetermined polypeptide sequence has been to use a so-called "two-hybrid" system wherein the predetermined polypeptide sequence is present in a fusion protein (Chien et al. (1991) *Proc. Natl. Acad. Sci. (USA)* 88: 9578). This approach identifies protein-protein interactions in vivo through reconstitution of a transcriptional activator (Fields S and Song O (1989) *Nature* 340: 245), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver S C and Hunt S W (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci. (USA)* 90: 5524; Jackson et al. (1993) *Mol. Cell. Biol.* 13; 2899; and Madura et al. (1993) *J. Biol. Chem.* 268: 12046). Two-hybrid systems have also been used to identify interacting structural domains of two known proteins (Bardwell et al. (1993) *med. Microbiol.* 8: 1177; Chakraborty et al. (1992) *J. Biol. Chem.* 267: 17498; Staudinger et al. (1993) *J. Biol. Chem.* 268: 4608; and Milne G T and Weaver D T (1993) *Genes Devel.* 7; 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci. (USA)* 89: 4159). Alternatively, an *E. coli*/BCCP interactive screening system (Germino et al. (1993) *Proc. Natl. Acad. Sci. (U.S.A.)* 90: 933; Guarente L (1993) *Proc. Natl. Acad. Sci. (U.S.A.)* 90: 1639) can be used to identify interacting protein sequences (i.e., protein sequences which heterodimerize or form higher order heteromultimers).

Each of these two-hybrid methods rely upon a positive association between two Gal4 fusion proteins thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a colorimetric enzyme assay or (2) as enhanced cell growth on a defined medium (e.g., HIS3). A positive readout condition is generally identified as one or more of the following detectable conditions: (1) an increased transcription rate of a predetermined reporter gene, (2) an increased concentration or abundance of a polypeptide product encoded by a predetermined reporter gene, typically such as an enzyme which can be readily assayed in vivo, and/or (3) a selectable or otherwise identifiable phenotypic change in an organism (e.g., yeast) harboring the reverse two-hybrid system. Generally, a selectable or otherwise identifiable phenotypic change that characterizes a positive readout condition confers upon the organism either: a selective growth advantage on a defined medium, a mating phenotype, a characteristic morphology or developmental stage, drug resistance, or a detectable enzymatic activity (e.g., β-galactosidase, luciferase, alkaline phosphatase, and the like).

Transcriptional activators are proteins that positively regulate the expression of specific genes. They can be functionally dissected into two structural domains: one region that binds to specific DNA sequences and thereby confers specificity, and another region termed the activation domain that binds to protein components of the basal gene expression machinery (Ma and Ptashne (1988) *Cell* 55: 443). These two domains need to be physically connected in order to function as a transcriptional activator. Two-hybrid systems exploit this finding by hooking up an isolated DNA binding domain to one protein (protein X), while hooking up the isolated activation domain to another protein (protein Y). When X and Y interact to a significant extent, the DNA binding and activation domains will now be connected and the transcriptional activator function reconstituted (Fields and Song (1989) *Nature* 340: 245). The yeast host strain is engineered so that the reconstituted transcriptional activator drives the expression of a specific reporter gene such as HIS3 or lacZ, which provides the read-out for the protein-protein interaction (Field and Song (1989) op.cit.; Chein et al. (1991) op.cit.). One advantage of two-hybrid systems for monitoring protein-protein interactions is their sensitivity in detection of physically weak, but physiologically important, protein-protein interactions. As such it offers a significant advantage over other methods for detecting protein-protein interactions (e.g., ELISA assay).

The invention also provides host organisms (typically unicellular organisms) which harbor a FEN-1 protein two-hybrid system, typically in the form of polynucleotides encoding a first hybrid protein, a second hybrid protein, and a reporter gene, wherein said polynucleotide(s) are either stably replicated or introduced for transient expression. In an embodiment, the host organism is a yeast cell (e.g., *Saccharomyces cervisiae*) and in which the reporter gene transcriptional regulatory sequence comprises a Gal4-responsive promoter.

Yeast comprising (1) an expression cassette encoding a GAL4 DNA binding domain (or GAL4 activator domain) fused to a binding fragment of FEN-1 (2) an expression cassette encoding a GAL4 DNA activator domain (or GAL4 binding domain, respectively) fused to a member of a cDNA library, and (3) a reporter gene (e.g., β-galactosidase) comprising a cis-linked GAL4 transcriptional response element can be used for screening for cDNA sequences encoding polypeptides which bind to FEN-1 with high affinity.

Yeast two-hybrid systems may be used to screen a mammalian (typically human) cDNA expression library, wherein cDNA is fused to a GAL4 DNA binding domain or activator domain, and a FEN-1 polypeptide sequence is fused to a GAL4 activator domain or DNA binding domain, respectively. Such a yeast two-hybrid system can screen for cDNAs that encode proteins which bind to FEN-1 sequences. For example, a cDNA library can be produced from mRNA from a human mature B cell (Namalwa) line (Ambrus et al. (1993) *Proc. Natl. Acad. Sci. (U.S.A.)*) or other suitable cell type. Such a cDNA library cloned in a yeast two-hybrid expression system (Chien et al. (1991) *Proc. Natl. Acad. Sci. (U.S.A.)* 88: 9578) can be used to identify cDNAs which encode proteins that interact with FEN-1 and thereby produce expression of the GAL4-dependent reporter gene. Polypeptides which interact with FEN-1 can also be identified by immunoprecipitation of FEN-1 with antibody and identification of co-precipitating species. Further, polypeptides that bind FEN-1 can be identified by screening a peptide library (e.g., a bacteriophage peptide display library, a spatially defined VLSIPS peptide array, and the like) with a FEN-1 polypeptide.

Once such cDNAs encoding FEN-1-interacting polypeptides are identified, they may be used for screening a bank of compounds (e.g., small molecule libraries) to identify agents which inhibit the binding interaction. Yeast comprising (1) an expression cassette encoding a GAL4 DNA binding domain (or GAL4 activator domain) fused to a binding fragment of FEN-1 (2) an expression cassette encoding a GAL4 DNA activator domain (or GAL4 binding domain, respectively) fused to the selected cDNA encoding the FEN-1-interacting protein, and (3) a reporter gene (e.g., β-galactosidase) comprising a cis-linked GAL4 transcriptional response element can be used for screening for agents which inhibit the cDNA-encoded polypeptide from binding to FEN-1 with high affinity. Such yeast are incubated with a test agent and expression of the reporter gene (e.g., β-galactosidase) is determined; the capacity of the agent to inhibit expression of the reporter gene as compared to a control culture identifies the agent as a candidate FEN-1 modulatory agent.

FEN-1-modulating agents which reduce the cell's capacity to repair DNA damage or inhibit DNA replication (e.g., by competitively inhibiting endogenous naturally-occurring FEN-1) are candidate antineoplastic agents or sensitizing agents which sensitize cells (e.g., neoplastic cells) to DNA damaging agents (e.g., alkylating agents and ionizing radiation). Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

Assays for detecting the ability of agents to inhibit or augment the DNA flap binding and/or cleavage activity of FEN-1 provide for facile high-throughput screening of agent banks (e.g., compound libraries, peptide libraries, and the like) to identify FEN-1 antagonists or agonists. Such antagonists and agonists may modulate FEN-1 activity and thereby modulate DNA repair competence and replicative potential.

Administration of an efficacious dose of an agent capable of specifically inhibiting FEN-1 activity to a patient can be used as a therapeutic or prophylactic method for treating pathological conditions (e.g., cancer, inflammation, lymphoproliferative diseases, autoimmune disease, neurodegenerative diseases, and the like) which are effectively treated by modulating FEN-1 activity and DNA repair and replication. Such agents which inhibit VDJ immunoglobulin recombination, isotype switching, T cell receptor gene shuffling, and the like may serve as immunosuppressant agents.

DNA flap substrates, cleavage and binding reactions and the like are practiced with reference to the Experimental Examples and Harrington and Lieber (1994) *Genes and Development* 8: 1344; Harrington and Lieber (1994) *The EMBO J.* 13: 1235; Hiraoka et al. (1995) *Genomics* 25: 220; and Harrington and Lieber (1995) *J. Biol. Chem.* 270: 4503. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific flap cleavage occurs in the control reaction(s). Conditions that do not permit specific binding and cleavage in control reactions (no agent included) are not suitable for use in binding assays.

Preferably, for determining binding of FEN-1 polypeptides to immobilized DNA flap structures, the FEN-1 polypeptide species is labeled with a detectable marker. Suitable labeling includes, but is not limited to, radiolabeling by incorporation of a radiolabeled amino acid (e.g., $^{14}$C-labeled leucine, $^{3}$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$p (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Labeled FEN-1 polypeptide(s) are contacted with immobilized flap substrates, or labeled flap substrates are incubated with immobilized FEN-1 polypeptides in the presence of unlabeled non-specific competitor under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of bound complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles,* (1984) Creighton (ed.), W. H. Freeman and Company, New York).

Specific binding of labeled DNA flap substrate or FEN-1 polypeptide to immobilized FEN-1 polypeptide or DNA flap substrate, respectively, is determined by including unlabeled competitor protein (e.g., albumin) and/or unlabeled DNA. After a binding reaction is completed, the amount of labeled species that is/are specifically bound to the immobilized species is detected. For example and not for limitation, after a suitable incubation period for binding, the aqueous phase containing non-immobilized labelled FEN-1 protein is removed and the substrate containing the immobilized DNA flap substrate species and any labeled FEN-1 protein bound to it is washed with a suitable buffer, optionally containing unlabeled blocking agent(s), and the wash buffer(s) removed. After washing, the amount of detectable label remaining specifically bound to the immobilized DNA flap substrate is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays.

In embodiments where a polypeptide or DNA flap substrate is immobilized, covalent or noncovalent linkage to a substrate may be used. Covalent linkage chemistries include, but are not limited to, well-characterized methods known in the art (Kadonaga and Tijan (1986) Proc. Natl. Acad. Sci. (U.S.A.) 83: 5889). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one embodiment, candidate therapeutic agents are identified by their ability to block the binding of a FEN-1 polypeptide to a DNA flap substrate.

Typically, a FEN-1 polypeptide used in these methods comprises an amino acid sequence identical to a naturally-occurring FEN-1 protein sequence, although mutant FEN-1 polypeptides are sometimes used if the mutant FEN-1 polypeptide binds to the DNA flap substrate under control assay conditions (e.g., physiological conditions).

Methods for Forensic Identification

The FEN-1 polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, blood-stained gloves, blood spots on the door of a white Ford Bronco, and the like) and subjected to RFLP analysis, allele-specific PCR, or PCR cloning and sequencing of the amplification product to determine the structure of the FEN-1 gene region. On the basis of the FEN-1 gene structure, the individual from which the sample originated will be identified with respect to his/her FEN-1 genotype. The FEN-1 genotype may be used alone or in conjunction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs 1995 catalog). Corresponding digestion products from each individual are loaded separately on an electrophoretic gel (typically agarose), electrophoresed, blotted to a membrane by Southern blotting, and hybridized with a labeled FEN-1 probe (e.g., a full-length FEN-1 cDNA sequence of FIG. 1 (B), FIG. 2 (B), or FIG. 5. Restriction fragments (bands) which are polymorphic among members of the population are used as a basis to discriminate FEN-1 genotypes and thereby classify individuals on the basis of their FEN-1 genotype.

Similar categorization of FEN-1 genotypes may be performed by sequencing PCR amplification products from a population of individuals and using sequence polymorphisms to identify alleles (genotypes), and thereby identify or classify individuals.

The invention also provides FEN-1 polynucleotide probes for diagnosis of disease states (e.g., neoplasia or preneoplasia) by detection of a FEN-1 mRNA or rearrangements or amplification of the FEN-1 gene in cells explanted from a patient, or detection of a pathognomonic FEN-1 allele (e.g., by RFLP or allele-specific PCR analysis). Typically, the detection will be by in situ hybridization using a labeled (e.g., $^{32}P$, $^{35}S$, $^{14}C$, $^{3}H$, fluorescent, biotinylated, digoxigeninylated) FEN-1 polynucleotide, although Northern blotting, dot blotting, or solution hybridization on bulk RNA or poly $A^+$ RNA isolated from a cell sample may be used, as may PCR amplification using FEN-1-specific primers. Cells which contain an altered amount of FEN-1 mRNA as compared to non-neoplastic cells of the same cell type(s) will be identified as candidate diseased cells. Similarly, the detection of pathognomonic rearrangements or amplification of the FEN-1 gene locus or closely linked loci in a cell sample will identify the presence of a pathological condition or a predisposition to developing a pathological condition (e.g., cancer, genetic disease). The polynucleotide probes are also used for forensic identification of individuals, such as for paternity testing or identification of criminal suspects (e.g., O. J. Simpson) or unknown decedents.

Methods of Rational Drug Design

FEN-1 polypeptides can be used for rational drug design of candidate FEN-1-modulating agents (e.g., antineoplastics and immunomodulators). The substantially purified FEN-1 and the identification of FEN-1 as a docking partner for 5' DNA flap substrates as provided herein permits production of substantially pure DNA flap/FEN-1 complexes (and DNA nick/FEN-1 complexes) and substantially pure FEN-1 polypeptides. The disclosed sequences and protein sources provide data for computational models which can be used for protein X-ray crystallography or other structure analysis methods, such as the DOCK program (Kuntz et al (1982) J. Mol. Biol. 161: 269; Kuntz ID (1992) Science 257: 1078) and variants thereof. Potential therapeutic drugs may be designed rationally on the basis of structural information thus provided. In one embodiment, such drugs are designed to prevent formation of a FEN-1 polypeptide:DNA flap complex. Thus, the present invention may be used to design drugs, including drugs with a capacity to inhibit binding of FEN-1 to DNA flaps or nicks and to catalyze nuclease activity on the flap strand. In one variation, such drugs are structural mimics of a FEN-1 polypeptide sequence.

Use of FEN-1 in Diagnostic Assays

The invention also provides a novel diagnostic assay, comprising contacting a sample believed to potentially contain a predetermined target polynucleotide sequence (e.g., a target polynucleotide; analyte) with a probe polynucleotide capable of specific hybridization to all or a portion of said target polynucleotide under assay conditions, and forming as a result of the hybridization a 5' flap structure which can be cleaved by FEN-1 releasing nucleotides (or polynucleotides) in the flap strand; incubating with FEN-1 and detecting the release of nucleotides (or polynucleotides) of the flap strand, the release of nucleotides (or polynucleotides) thereby reporting the formation of a flap structure and thereby reporting the presence, and optionally quantity, of the predetermined target polynucleotide sequence in the sample as proportional to the amount of cleaved, released nucleotides or polynucleotides. Typically, the probe polynucleotide comprises two portions, a first portion which hybridizes to the target sequence and a second portion which is adjacent to said first portion and which forms the flap strand; frequently an adjacent polynucleotide is present which hybridizes to the portion of the target polynucleotide immediately 5' to the portion of the target which hybridizes to the probe polynucleotide sequence. The portion of the probe polynucleotide which forms the flap is typically labelled, and the entire probe may be labelled; in some embodiments, the target polynucleotide is 5'-end-labeled. Often, the probe polynucleotide is immobilized. The release of label in the presence of FEN-1 measures the abundance of target polynucleotide in the sample. For illustration and not limitation, with reference to FIG. 6, a probe may correspond to the flap strand, a target polynucleotide may correspond to the bridge strand ($F_{br}$), and an adjacent strand may correspond to the $F_{adj}$ strand, as shown. Alternatively, a probe polynucleotide, typically labelled, may be immobilized via its 5' end such that hybridization to the target polynucleotide will form a cleavable flap which can be cleaved by FEN-1 releasing the cleaved portion of the probe polynucleotide which is hybridized to the target; quantitating the amount of released label thereby detects the amount of target polynucleotide in the sample.

Kits and FEN-1 Reagents

The invention also provides kits comprising a vial containing substantially purified FEN-1 having 5' flap cleavage activity; such kits can be sold for practicing polynucleotide diagnostic assays according to the methods described. Vials of purified FEN-1 can be sold to the clinical lab or scientist as commercial reagents, just like conventional diagnostic products or laboratory biologicals (e.g., restriction enzymes, Taq polymerase, monoclonal antibodies), categories which have sufficient utility to have merited the granting of numerous U.S. patents. Such reagents which can be used in research and diagnostics have been patented; for example, the restriction endonucleases AscI, FseI, PmeI, XcyI, SplI, SrfI, and ApoI, among others, have been patented in the U.S. (see, U.S. Pat. Nos. 5,061,628, 5,196,330, 4,588,689, 4,886,756, 5,300,432, 5,200,336, and 5,200,337), among others.

The following examples are given to illustrate the invention, but are not to be limiting thereof. All percentages given throughout the specification are based upon weight unless otherwise indicated. All protein molecular weights are based on mean average molecular weights unless otherwise indicated.

EXPERIMENTAL EXAMPLES

Example 1: Identification of an Activity Which Cuts DNA Flaps

Flap structures have been proposed as intermediates in a variety of systems including DNA end-joining, homologous recombination and DNA replication. In order to identify mammalian flap cutting activities in vitro, we designed the synthetic flap structure show in FIG. 6. This structure, called Flap Substrate 1, was created by annealing three oligonucleotides together. We refer to these individual oligonucleotide as the flap strand, the $F_{br}$ (bridge) strand and the $F_{adj}$ (adjacent) strand. The $F_{br}$ strand is complementary to both the flap strand and the $F_{adj}$ strand, and therefore bridges the two strands allowing the structure to form. Flap Substrate 1 is a 5' flap structure because the flap strand terminates with a 5' single-stranded end. Likewise, 3' flap structures have a flap strand which terminates in a 3' end.

Treatment of Flap Substrate 1 with crude nuclear extract from 1–8 pre-B cells or from NIH3T3 fibroblasts resulted in the formation of two major products. The 19 nt product was the result of a cut 1 nt distal to the elbow, in the single-stranded region of the flap strand. The 21 nt product was the result of a cut 1 nt proximal to the elbow, in the double-stranded region of the flap strand. These products could be detected with as little as 10 ng of protein from the 1–8 crude nuclear extract in the presence of a 1,000-fold molar excess of salmon sperm DNA. Based on this specificity, we have named this enzyme flap endonuclease-1 (FEN-1).

Analysis of nuclear extracts from other species indicated that flap cleavage activity is evolutionarily conserved. We detected flap cutting activity in extracts from calf thymus, rabbit reticulocytes, Chinese hamster fibroblasts and Drosophila embryos.

Purification of FEN-1

FEN-1 was purified from the nuclear fraction of a mouse pre-B cell line. The chromatographic behavior of FEN-1 was monitored using Flap Substrate 1 in the standard FEN-1 endonuclease assay.

FEN-1 activity eluted from the final column as a single 50 kDa band as assessed by silver-stained SDS-PAGE. The amount of activity in each of the active fractions correlated with the amount of 50 kDa protein present.

Biochemical properties of purified FEN-1

Analysis of the effects of salt concentration, pH and divalent metal ion concentration on this reaction are shown in Table I and Table II.

TABLE I

| Endonuclease activity characterization | |
|---|---|
| FEN-1 activity versus pH Ph | % Activity |
| 5 | <1 |
| 6 | 20 |
| 7 | 66 |
| 8 | 100 |
| 9 | 62 |
| 10 | 7 |
| FEN-1 activity versus [monovalent mental ion] [Monovalent metal ion] (mM) | Activity |
| 0 salt | 100 |
| 50 NaCl | 14 |
| 100 NaCl | 1 |
| 150 NaCl | <0.5 |
| 50 KCl | 14 |
| 100 KCl | 2 |
| 150 KCl | <1 |

TABLE I-continued

Endonuclease activity characterization

| FEN-1 activity versus [divalent metal ion] [Divalent metal ion] (mM) | % Activity |
|---|---|
| 1 MgCl$_2$ | 72 |
| 10 MgCl$_2$ | 100 |
| 1 MnCl$_2$ | 1121 |
| 10 MnCl$_2$ | 2725 |
| 1 CeCl$_2$ | 17 |
| 1 ZnCl$_2$ | 2 |
| 5 EDTA | <1 |
| 1 MgCl$_2$ and 1 CaCl$_2$ | 56 |
| 1 MgCl$_2$ and 1 ZnCl$_2$ | <1 |

FEN-1 was optimally active at pH 8 in the presence of 0 mM monovalent ions. NaCl and KCl were equally inhibitory with ~85% inhibition occurring at 50 mM monovalent salt. FEN-1 activity was relatively insensitive to pH. Activity was detected from pH 6 to 10. We also found that divalent metal ions were absolutely required for FEN-1 activity. Replacement of MgCl$_2$ with 5 mM EDTA completely inhibited the reaction. Interestingly, substitution of MgCl$_2$ with 1 mM MnCl$_2$ resulted in the formation of ~10-fold more product. The concentration of MgCl$_2$ affected the cleavage site preference of FEN-1. At 0.1 mM Mg$^{2+}$, the enzyme cleaved Flap Substrate 1 predominantly 1 nt proximal to the elbow to give the 21 nt product. As the Mg$^{2+}$ concentration was increased, more cutting occurred 1 nt distal to the elbow to give the 19 nt product. Maximum product was formed at 10 mM MgCl$_2$ which yielded an equimolar ratio of the two products. Interestingly, sequences near the flap protrusion also seemed to affect the preferred site of cleavage by FEN-1, as discussed below.

TABLE II

Exonuclease activity characterization

| FEN-1 activity versus pH pH | % Activity |
|---|---|
| 5 | 6 |
| 6 | 60 |
| 7 | 50 |
| 8 | 100 |
| 9 | 60 |
| 10 | 43 |

| FEN-1 activity versus [monovalent ion] {Monovalent ion] (mM) | % Activity |
|---|---|
| 0 salt | 100 |
| 50 NaCl | 2 |
| 100 NaCl | <0.5 |
| 150 NaCl | <0.5 |
| 50 KCl | 3 |
| 100 KCl | <0.5 |
| 150 KCl | <0.5 |

| FEN-1 activity versus [divalent metal ion] [Divalent ion] (mM) | % Activity |
|---|---|
| 0.1 MgCl$_2$ | 100 |
| 1 MgCl$_2$ | 55 |
| 10 MgCl$_2$ | 5 |
| 0.1 MnCl$_2$ | 132 |
| 1 MnCl$_2$ | 124 |
| 10 MnCl$_2$ | 166 |

TABLE II-continued

Exonuclease activity characterization

| | % Activity |
|---|---|
| 5 EDTA | <0.5 |
| 1 MgCl$_2$ and 1 ZnCl$_2$ | <1 |

Sequence independent cleavage and structure specificity

A second flap structure, called Flap Substrate 2, as used to determine if FEN-1 has any sequence specificity. This substrate is different from Flap Substrate 1, but has the same 5' flap structure. FEN-1 efficiently cleaved Flap Substrate 2. This indicates that FEN-1 recognizes the flap structure and not a specific sequence in the substrate. Flap Substrate 2 had only one major cut site which was located 1 nt proximal to the elbow, whereas Flap Substrate 1 had two major cut sites.

The specificity of FEN-1 for flap structures was further tested by incubating purified FEN-1 with the labeled flap strand alone. This strand was not cleaved when not annealed to the other strands. This result demonstrates that purified FEN-1 has no detectable single-strand endo- or exonuclease activities. Furthermore, incubation of FEN-1 with supercoiled pBluescript plasmid did not result in any detectable nicking or double-strand cleavage, demonstrating that FEN-1 does not have any double-strand endonuclease activity.

To test whether FEN-1 cleaves any single-strand/double-strand junction, FEN-1 was assayed for its ability to cleave 5' or 3' overhangs. Cleavage of this structure near the single-strand/double-strand junction would result in the generation of a product of ~15 nt on a denaturing acrylamide gel. These overhang structures were not cleaved, showing that FEN-1 is not simply recognizing the single-strand/double-strand junctions, but instead is specific for the flap structure.

Strand specificity of FEN-1

To determine whether FEN-1 cleaves flap structures in a strand-specific manner, the $F_{br}$ strand of Flap Substrate 1 was 5' end-labeled. Cutting of the $F_{br}$ strand near the flap protrusion would generate an ~14 nt labeled product on a denaturing acrylamide gel. Cutting of this strand did not occur, indicating that FEN-1 cleaves the flap structure in a strand-specific fashion.

Effect of Flap Length on FEN-1 Cleavage

Models for DNA end-joining and homologous recombination have been proposed which predict flap intermediates. The flap strands in these models can vary from 1 nt to several hundred in length. If FEN-1 is involved in DNA end-joining, one would predict that it should cleave short single-stranded flaps of 1 to 5 nt in length. To test this, we varied the length of the flap strand of Flap Substrate 2 while holding the lengths of the $F_{br}$ and $F_{adj}$ strands constant. We found that FEN-1 was capable of cleaving both 1 and 5 nt flaps efficiently. This result demonstrates that FEN-1 is capable of resolving structures such as those proposed in DNA end-joining.

Ability of FEN-1 to Cleave Other Structures

In addition to 5' flap structures, 3' flap structures have also been proposed to serve as intermediates in homology-dependent DNA end-joining. It was of interest, therefore, to test whether FEN-1 also cleaves flaps with a 3' single-stranded end. Using Flap Substrate 1 as a positive control, no detectable cleavage of the 3' flap structure was observed, even in the presence of 15 U of FEN-1.

To analyze further the substrate specificity of FEN-1, several derivatives of the flap structure were tested. The presence of the $F_{adj}$ strand was found to be required for efficient cleavage. In the case of Flap Substrate 2, cutting efficiency was reduced 100-fold when the $F_{adj}$ strand was absent. Analysis of other flap sequences, such as Flap Substrate 1, confirms the importance of the $F_{adj}$ strand, although the reduction in cutting efficiency was only 20-fold for this substrate. In addition, the absence of the $F_{adj}$ strand did not simply change the cleavage site to the $F_{br}$ stand. These results indicate that FEN-1 cleavage is dependent on the presence of the complete flap structure. It is conceivable, however, that efficient cleavage may occur in the presence of $F_{adj}$ strand which is recessed from the flap strand elbow by one or more bases. We tested this and found that cleavage efficiency dropped to 92%, 48% and 15% of that with Flap Substrate 1 when the $F_{adj}$ strand was recessed by 1, 3 and 5 nt, respectively. Thus, FEN-1 can cleave flap structures at a reduced efficiency in the presence of a recessed $F_{adj}$ strand.

T4 endo VII has also been shown to cleave Y-junctions. A Y-junction can be made simply by annealing a fourth oligonucleotide to the single-stranded tail of the flap strand to make it double-stranded. We found that FEN-1 cleaved the single-stranded flap 200-fold more efficiently than the Y-junction. The residual cleavage may be the result of a small amount of flap substrate which is not annealed with the oligonucleotide SC6. Thus, the inability of FEN-1 to cleave Y-junctions efficiently further confirms its specificity for 5' single-stranded flaps.

If the RNA strand of the Okazaki fragment is displaced by the incoming DNA polymerase, an RNA flap structure would be formed. We created this structure by replacing the labeled DNA flap strand (HJ42) of Flap Substrate 1 with a labeled RNA oligonucleotide of the same sequence (HJ49). The resulting RNA flap sequence was not cleaved by FEN-1.

FEN-1 has 5'-3' Exonuclease Activity

FEN-1 was incubated with a variety of end-labeled substrates. We found that our FEN-1 preparation had exonuclease activity with a specificity for 5' recessed ends. The product of this reaction was low molecular weight nucleotides ranging from one to several nucleotides in length as determined by high percentage sequencing polyacrylamide gels. This exonuclease did not act on blunt ends, 3' recessed ends or single-stranded DNA. In addition, this exonuclease did not cleave RNA oligonucleotides alone or when annealed to DNA. These results indicate that the exonuclease present in the FEN-1 preparation is a 5'-3' exonuclease which is specific for double-stranded DNA.

Based on the chromatographic elution profiles and the similar effects of salt, pH and divalent metal ions, it appears that FEN-1 is responsible for the exonuclease activity.

Materials and Methods

DEAE Sephrose, heparin Sepharose, Phenyl Superose HR 5/5, Blue Sepharose, Mono S HR 5/5 and Sephadex G-25 were purchased from Pharmacia LKB, Inc. Hdroxylapatite, Biorex 70 and low molecular weight SDS-PAGE standards were purchased from Bio-Rad [τ-$^{32}$P]ATP and [α-$^{32}$P]dTTP (3000 Ci/mmol) were purchased from Amersham. SDS, bovine serum albumin Fraction V (BSA) and rRNA were purchased from Sigma. Acrylamide was purchased from Boehringer Mannheim. Penicillin-streptomycin was purchased from Irvine Scientific. T4 polynucleotide kinase (PNK) was obtained from New England Biolabs. Exominus Klenow fragment of *E. coli* DNA Pol I was purchased from United States Biochemical. Fetal bovine serum (FBS) and RPMI 1640 were purchased from Gibco-BRL. X-OMAT AR film was purchased from International Biotechnologies, Inc.

FEN-1 Purification

All purification steps were carried out at 0°–4° C. Six liters of the murine pre-B cell line, 1–8 (Alt et al., 1984), were grown to $2\times10^6$ cells/ml in RPMI 1640, 10% FBS, 50 μM β-mercaptoethanol (βME), 100 μg/ml penicillin-streptomycin in spinner flasks. Eighteen liters of RPMI 1640 and 100 μg/ml penicillin-streptomycin were then added, and the cells were allowed to grow for an additional 24 h. The cells were harvested at a cell density of $1-1.5\times10^6$ cells/ml and spun at 1000 g in a Beckman JA-10 rotor for 5 min. The cell pellet was then washed with 500 ml of ice-cold PBS (5 mM $NaP_i$ pH 7.4, 137 mM NaCl, 3 mM KCl) supplemented with 1 g/l $MgCl_2$ and pelleted as above. Nuclei were isolated by allowing the cell pellet to swell in 100 ml Buffer A (10 mM HEPES-KOH pH 7.8, 1.5 mM $MgCl_2$, 10 mM KCl, 0.5 mM DTT) for 10 min on ice. The swollen cells were spun for 5 min at 2500 g in a Beckman J6B centrifuge, resuspended in 40 ml Buffer A and homogenized with 20 strokes of the B-pestle in a Dounce homogenizer. The nuclei were collected by centrifugation at 2500 g in a Beckman J6B for 5 min and lysed by adding 40 ml of Buffer B (20 mM EPES-KOH pH 7.8, 0.42M NaCl, 25% glycerol, 1.5 mM $MgCl_2$, 0.2 mM EDTA, 0.5 mM DTT, 0.5 mM PMSF). Nuclear lysis was completed with 20 strokes of the B-pestle in a Dounce homogenizer. The mixture was incubated on ice for 30 min and then spun at 30 000 g in a Beckman JA-20 rotor to remove nuclear debris. This clarified nuclear extract typically had a protein concentration of 2–4 mg/ml. To remove nucleic acids, the nuclear fraction was applied directly to a DEAE Sepharose column (1.6 cm×7 cm, 10 ml) equilibrated in Buffer C (50 mM Tris pH 7.4) containing 500 mM NaCl. The flow-through was diluted with 10 volumes of Buffer D (50 mM Tris pH 8.5) and loaded onto a DEAE Sepharose column (2.6 cm×7.5 cm, 31 ml) which was equilibrated with Buffer D containing 50 mM NaCl. The flow-through from this second DEAE column was loaded directly onto a heparin Sepharose (1.6 cm×6 cm, 8 ml) column equilibrated in Buffer D containing 50 mM NaCl. Following loading, the heparin Sepharose column was washed with 40 ml Buffer D containing 50 mM NaCl and then with 40 ml of Buffer C containing 200 mM NaCl. FEN-1 was eluted with 40 ml of Buffer C containing 400 mM NaCl. Solid $(NH_4)_2SO_4$ (10.4 g) was added to the heparin Sepharose pool (40 ml) while stirring on ice. This solution was spun at 28 000 g for 15 min in a Beckman JA-20 rotor, and the supernatant was applied to an FPLC Phenyl Superose HR 5/5 column which was equilibrated with Buffer F [25 mM Tris pH 7.4, 2M $(NH_4)_2SO_4$]. Following loading, the column was washed with 10 ml of Buffer F. FEN-1 activity was eluted with a 20 ml linear gradient from Buffer F to Buffer G (50 mM Tris pH 8, 10% glycerol). The active fractions (6 ml) were diluted immediately with 60 ml of Buffer H (5 mM $KP_i$, pH 7) and loaded onto a hydroxylapatite column (1 cm×4 cm, 3 ml) equilibrated in Buffer H. The column was washed with 10 ml Buffer H, and FEN-1 was eluted with a 30 ml linear gradient from Buffer H to 500 mM $KP_i$ pH 7. Active fractions were pooled (9 ml), diluted with 40 ml of Buffer G, and loaded onto a Blue Sepharose column (5 mm×10 mm, 1 ml) which was equilibrated in Buffer G containing 50 mM NaCl. The column was washed successively with 20 ml of Buffer G containing 50 mM NaCl and then with 20 ml Buffer G containing 380 mM NaCl. FEN-1 was eluted with 1M NaCl in Buffer G. Active fractions (6 ml) were diluted with 44 ml of buffer G and loaded onto a Mono S HR 5/5 column which was equilibrated with Buffer G containing 50 mM NaCl. The column was washed with 10 ml Buffer G containing 50 mM NaCl and then with 10 ml Buffer I (50 mM Tris pH 9.5, 10% glycerol) containing 50 mM NaCl. The activity was eluted with a linear gradient from 50 mM NaCl to 600 mM NaCl in Buffer I. Active fractions were diluted 5-fold with Buffer J (25 mM KP$_i$, pH 7) and loaded onto a Biorex 70 column (1 cm×1 cm, 1 ml). The column was washed with 1 ml Buffer J, and then eluted with a linear gradient from 0 to 700 mM NaCl in Buffer J. One milliliter fractions were collected into siliconized polypropylene tubes. Active fractions were frozen at −70° C. in the presence of 100 µg/ml BSA.

Preparation of nuclear extracts

Approximately 1×10$^9$ cells were harvested from culture or from the indicated tissue. After washing the cells in 50 ml of PBS supplemented with 1 g/l MgCl$_2$, the cells and nuclei were lysed as described in the FEN-1 purification procedure except the volumes of Buffers A and B were 20-fold lower. These extracts were either used immediately or frozen in liquid nitrogen and stored at −80° C. until use.

Oligonucleotides

All DNA oligonucleotides were purchased from Operon Technologies, Inc. (Alameda, Calif.). The SC series of oligonucleotides was a kind gift from Pat Brown (Department of Biochemistry, Stanford). The sequence of each is shown after its name and is written from 5' to 3'. HJ39, CACGTTGACTGAATC (SEQ ID NO: 53); HJ40, ACCGTCTTGAGGCAGAGT (SEQ ID NO: 54); HJ41, GGACTCTGCCTCAAGACGGTAGTCAACGTG (SEQ ID NO: 55); HJ42, CATGTCAAGCAGTC-CTAACTTTGAGGCAGAGTCC (SEQ ID NO: 56); HJ43, CACGTTGACTACCGTC (SEQ ID NO: 57); HJ47, GTAG-GAGATGTCCCTTGATGAATTC (SEQ ID NO: 58); SC1, CAGCAACGCAAGCTTG (SEQ ID NO: 59); SC2, TAG-CAGGCTGCAGGTCGAC (SEQ ID NO: 60); SC3, GTC-GACCTGCAGCCCAAGCTTGCGTTGCTG (SEQ ID NO: 61); SC4, AGGCTGCAGGTCGAC (SEQ ID NO: 62); SC5, ATGTGGAAAATCTCTAGCAGGCTGCAGGTCGAC (SEQ ID NO: 63); SC6. TGCTAGAGATTTTCCACAT (SEQ ID NO: 64). In addition, two RNA oligonucleotides were purchased from National Biosciences (Plymouth, Minn.). The sequence of each is shown after its name and is written from 5' to 3'. HJ49, GATGTCAAGCAGTC-CTAACTTTGAGGCAGAGTCC; HJ50, CCCA-GATACGG. Prior to use, each oligonucleotide was gel purified on a 15% denaturing polyacrylamide gel and recovered by 'crush and soak' (Sambrook et al., 1989).

Preparation of flap substrates and derivatives

Substrates were prepared by first 5' end-labeling 5 pmol of the strand on which cutting was to be measured using [τ-$^{32}$P]ATP and T4 polynucleotide kinase (PNK) according to Sambrook et al. (1989). PNK and unincorporated nucleotides were removed by phenol extraction followed by spin column gel filtration through a 1 ml Sephadex G-25 column. The specific activity of all labeled oligonucleotide was then annealed to 10 pmol of the other oligonucleotides in 50 µl of 20 mM Tris pH 7.4, 150 mM NaCl by boiling the tube for 2 min in 300 ml H$_2$O. The oligonucleotides were allowed to cool slowly to 4° C. in the same 300 ml H$_2$O.

Flap endonuclease assay

Flap cutting activity was measured in a 15 µl reaction containing 50 mM Tris pH 8, 10 mM MgCl$_2$, 0.5 mM βME, 100 µg/ml BSA, and 10 fmol of 5' end-labeled substrate. When crude fractions were assayed, 0.5 µg sonicated salmon sperm DNA (1 kb average size) was added to compete away non-specific nucleases. After 30 min at 30° C., the reaction was terminated by adding 15 µl of 95% formamide, 10 mM EDTA, 1 mg/ml bromophenol blue, 1 mg/ml xylene cyanole. The tubes were heated to 95° C. for 5 min, loaded onto a 10% or 15% polyacrylamide gel (35 cm×42.5 cm) containing 7M urea and 1×TBE (89 mM Tris, 89 mM boric acid, 2 mM EDTA, pH 8), and run for 90 min at 75 W. Reaction products were visualized by autoradiography or quantified using a PhosphorImager (Molecular Dynamics). A unit of activity is defined as the amount of enzyme required to cleave 1 fmol of Flap Substrate 1 under standard FEN-1 endonuclease assay conditions.

Oligonucleotide exonuclease assay

These structures were labeled and annealed using the same procedure described for the flap substrates. One exception to this is the 3' labeled recessed end substrate. This substrate was made by first annealing oligonucleotides HJ41 and HJ43. The annealed substrate was then 3' end-labeled with 1 U of Exo-minus Klenow in the presence of only [α-$^{32}$P]dTTP. This allows no more than two nucleotide bases to be incorporated. Following labeling and annealing, the substrates were purified by running a 20% native polyacrylamide gel to ensure that all unincorporated nucleotide was removed. The substrates were eluted from the gel by crush and soak at 30° C. (Sambrook et al.), 1989). Following precipitation, the DNA was resuspended in 20 mM Tris pH 7.4, 150 mM NaCl.

The standard oligonucleotide FEN-1 exonuclease assay was carried out in a 15 µl reaction containing 10 fmol of labeled substrate in 10 mM Tris pH 8.0.1 mM MgCl$_2$, 0.5 mM βME for 30 min at 30° C. Reactions were stopped by the addition of 15 µl 95% formamide, 5 mM EDTA, 1 mg/ml xylene cyanole and 1 mg/ml bromophenol blue. The tubes were then heated to 95° C. for 5 min and loaded onto a 15% polyacrylamide gel (17 cm×15 cm) containing 7M urea and 1×TBE. The reaction products were visualized by autoradiography or quantified using a PhosphorImager (Molecular Dynamics).

Poly[d(AT)] exonuclease assay

Poly[d(AT)] was labeled according to Goulian et al. (1990) except that [α-$^{32}$P]dTTP was used in place of [$^3$H] dTTP. The specific activity of the final DNase I nicked substrate was 3×10$^6$ c.p.m./nmol. This substrate (30 ng) was incubated with 10 U of FEN-1 in 10 mM Tris pH 8, 0.1 mM MgCl$_2$, 0.5 mM βME and 100 µg/ml BSA in a 100 µl reaction. Following a 30 min incubation at 30° C., the reaction was stopped by adding 25 µl salmon sperm DNA (3 mg/ml) and 125 µl of 20% TCA. The tube was incubated on ice for 5 min and then spun in a microfuge for 15 min at 15 000 r.p.m. The supernatant was removed, and the acid-soluble counts were determined in a scintillation counter (Beckman).

Example 2 Cloning the cDNA encoding Mouse FEN-1

DNA flap substrate 1 was designed to detect structure-specific endonucleases in mammalian cells, (FIG. 6). This substrate is a 5' flap structure because the flap strand terminates with a 5' single-stranded end. Conversely, 3' flap structures have a flap strand that terminates with a 3' single-stranded end. Both 5' and 3' flap structures are composed of a flap strand, an F$_{br}$ (bridge) strand, and an F$_{adj}$ (adjacent) strand.

FEN-1, which specifically cleaves 5' flap structures but not 3' flap structures. Cleavage of flap substrate 1 occurs primarily at 1 nucleotide proximal and 1 nucleotide distal to the elbow of the flap strand. Other 5' flap structures, however, are cleaved by FEN-1 primarily at 1 nucleotide proximal to the flap strand elbow.

We microsequenced tryptic fragments of purified murine FEN-1 and used this amino acid sequence to design degenerate oligonucleotide probes. An initial screen of 300,000 plaques from a mouse thymocyte cDNA library yielded eight positive clones that were related by restriction digest. The largest clone was 2.1 kb and produced a protein of the 25 expected molecular weight when transcribed and translated in vitro.

Materials and methods

Cloning of FEN-1 and YKL510. Tryptic fragments from 35 pmoles of FEN-1 (as determined by amino acid analysis) were HPLC purified and sequenced (Aebersold et al. 1987). Degenerate oligonucleotides HJ53 and HJ54 were designed, 5'-end-labeled with [$\tau^{32}$P]ATP, and hybridized to λZAP phage plaques containing a mouse thymocyte cDNA library (Sambrook et al. 1989). Positives were plaque purified and converted to plasmids according to the manufacturer's instructions (Stratagene). PstI and PvuII restriction fragments of the largest clone designated pBS-FEN, were ligated into pBlue-script to form overlapping subclones. Each subclone was then sequenced on both strands (Sanger et al., 1977). Alignment of FEN-1 with related genes was carried out by use of the Blast server (Altschul et al. 1990).

Construction of E. coli expression vectors. FEN-1 was liberated from the pBS-FEN by digestion with NcoI and BamHI and cloned directionally into the NcoI and BamHI sites of PET 11d (Studier et al. 1990) to create PET-FEN. YKL510 was cloned from S. cerevisiae genomic DNA by PCR with primers HJ60 and HJ61. Primter HJ60 created an NcoI site at the ATG translation start of YKL510, which allowed the PCR product to be cloned into the NcoI site of PET 11d to create PET-YKL. RAD2 was subcloned from pNF2000 (Naumovski and Friedberg 1984) into the SalI site of pBluescript to create pBS-RAD2. RAD2 was amplified by PCR from pBS-RAD2 using primers HJ62 and VBSK1. These primers created an NcoI site at the ATG translation start of RAD2 allowing the PCR product to be cloned directionally into the NcoI and BamHI sites of PET 11d to create PET-RAD2. PET-ΔRAD2 was created by deleting the region between the NcoI site and the SfuI site in PET-RAD2 and replacing it with the N region of RAD2, which was PCR amplified from pBS-RAD2 with primers HJ62 and HJ63.

Overproduction of enzymes and extract preparation. PET-FEN, PET-YKL, PET-RAD2, PET-ΔRAD2, AND PET 11d were transformed separately into the E. coli strain BL21 (DE3) (Studier et al. 1990) by electroporation and plated onto LB plates containing 100 μg/ml of ampicillin. Colonies from each transformation were inoculated into 2 liters of LB containing 100 μg/ml of ampicillin. The culture was shaken at 37° C. until the $OD_{600}$=0.8 and then induced with 0.5 mM IPTG for 2 hr. Following induction, cells were harvested by centrifugation, resuspended in 40 ml of buffer A (50 mM Tris at pH 8.5, 50 mM NaCl), and lysed by sonication. Lysates were cleared by centrifugation at 25,000 g and assayed for flap cleavage.

Enzyme purifications. FEN-1 was purified from 2 liters of E. coli, BL21(DE3), containing the FEN-1 expression vector PET-FEN. The crude extract from these cells was prepared as described above and loaded onto a DEAE-Sepharose column (2.6×8 cm, 30 ml). The flowthrough was collected and loaded directly onto a heparin-Sepharose column (1.6×4 cm, 6 ml). The column was washed with buffer B (50 mM Tris at pH 7.4) containing 200 mM NaCl, and FEN-1 was eluted with buffer B containing 400 mM NaCl. The heparin-Sepharose pool (25 ml) was diluted with 50 ml of buffer C (20 mM $KP_i$ at pH 7, 5 mM EDTA) and loaded onto a denatured DNA agarose column (1.6×3 cm, 5 ml). Following loading, the column was washed with buffer C and developed with a linear gradient from 0 to 600 mM KCl in buffer C. Active fractions were pooled and diluted with 30 ml of buffer D (50 mM Tris at pH 9.5) and loaded onto a Mono S HR 5/5 column. FEN-1 was eluted with a gradient from 0–600 mM NaCl in buffer D. Active fractions were pooled and loaded directly onto a hydroxylapatite column (1.6×3 cm, 5 ml), which was subsequently developed with a gradient from 5 to 350 mM $KP_i$ at pH 7. The hydroxylapatite fractions containing FEN-1 activity were pooled and labeled purified recombinant FEN-1 (fraction V).

YKL510 and ΔRAD2 were purified from E. coli by use of the same procedure as FEN1 and were found to behave similarly to FEN-1 at each chromatographic step. Purified YKL510 and ΔRAD2 from the hydroxylapatite column are designated fraction V. As a control, extracts from E. coli cells containing PET 11d were prepared and purified exactly as done for YKL510 and ΔRAD2. At each column, fractions corresponding to active fractions in the YKL510 or ΔRAD2 purifications were pooled. The final purified material was found to be devoid of detectable nuclease activity and is designated purified PET (fraction V).

Nuclease Assays. The standard flap cleavage assay was performed as described previously (Harrington and Lieber 1994). Briefly, oligonucleotide HJ42 was phosphorylated with [$\lambda^{32}$P]ATP and annealed to oligonucleotides HJ41 and HJ43 to produce flap substrate 1. Reactions contained 10 fmoles of flap substrate 1 in 15 μl of 50 mM Tris (pH 8), 10 mM $MgCl_2$, 100 μg/ml of BSA, and the indicated amount of extract or enzyme. Following incubation at 30° C. for 30 min, the reaction was terminated by the additional of 15 μl of 95% formamide, 1 mg/ml of bromophenol blue, and 1 mg/ml of xylene cyanole and then heated to 95° C. for 5 min. Products were separated on a 15% denaturing polyacrylamide gel (7M urea) and visualized on a PhosphorImager. One unit of nuclease activity is defined as the amount of enzyme required to cleave 1 fmole of substrate under standard assay conditions. For FEN-1, YKL510, or ΔRAD2, 1 unit of flap cleavage activity≅0.1 ng of purified protein.

The exonuclease assay was performed as described previously (Harrington and Lieber 1994). Briefly, oligonucleotide SC6 was phosphorylated with [$\lambda^{32}$P]ATP and annealed to oligonucleotide SC5. The annealed oligonucleotide substrate was purified on a 15% native acrylamide gel to remove all unincorporated label. Reactions were performed as in the standard flap assay; however, flap substrate 1 was replaced with SC5/6, and the concentration of $MgCl_2$ was 0.1 mM.

The FEN-1 CDNA insert was subcloned into the E. coli expression vector, PET 11d (Studier et al. 1990) to create PET-FEN. On induction, cells containing PET-FEN, but not PET 11d, produced a soluble 50-kD protein (data not shown). In addition, extracts from cells containing PET-FEN specifically cleaved a 5' flap structure, whereas extracts from cells containing PET 11d did not. Cleavage of the flap substrate occurred near the elbow of the displaced flap strand and resulted in labeled products that were 17–23 nucleotides in length. Using a modification of the purification procedure described supra, recombinant FEN-1 was purified to a single band on a Coomassie-stained SDS polyacrylamide gel.

To confirm that the above cDNA clone encodes FEN-1, the purified recombinant FEN-1 (fraction V) was compared with FEN-1 that was purified previously from mouse lymphocytes. The enzymatic activities and specificities of these two enzyme preparations were identical. Recombinant FEN-1 cleaved three different 5' flap structures and had 5'-3' double-strand-specific exonuclease activity but did not cleave 5' pseudo-Y structures or single-stranded DNA. A 5' pseudo-Y structures or single-stranded DNA. A 5' pseudo-Y structure is a 5' flap structure that is missing the $F_{adj}$ strand. In addition, both enzyme preparations failed to cleave 3' flap structures.

By Western blot, antibodies generated against recombinant FEN-1 (fraction V) recognize FEN-1 purified from lymphocytes. These antibodies also inhibit murine lymphocyte FEN-1 nuclease activity when present in the reaction, whereas control antibodies do not. Taken together, these results clearly indicate that the cDNA clone described below encodes FEN-1.

The nucleotide sequence of FEN-1 revealed an open reading frame of 1134 bp (FIG. 2). The amino acid sequence of this putative polypeptide was found to be highly homologous to the RAD2 protein family. The strongest homology was found between FEN-1 and YKL510, an open reading frame in *Saccharomyces cerevisiae* with previously unknown function and unknown expression status. In addition to being the same size, FEN-1 and YKL510 were 60% identical (78% similar) at the amino acid level. FEN-1 was also found to be equally homologous in sequence and structure to the *Schizosaccharomyces pombe* Rad2 gene (Lehmann et al. 1991; Carr et al. 1993).

Significant homology also found between FEN-1 and regions within *S. cerevisiae* RAD2, termed N, I, and C.

One difference within the RAD2 family is that the N and I regions are separated to varying extents. In FEN-1 and YKL510, these regions are separated by ~15 amino acids, whereas in RAD2, this separation is over 600 amino acids. We have designated this intervening sequence the S-region (spacer).

On the basis of the high degree of conservation between FEN 1 and YKL510, it is likely that YKL510 is the yeast analog of FEN-1. We cloned the YKL510 gene into PET 11d and expressed it in *E. coli*. We found that extracts from cells containing PET-YKL specifically cleaved a 5' flap structure, whereas extracts from cells containing PET 11d were inactive on this substrate. Using the standard flap cleavage assay to monitor chromatographic behavior, recombinant YKL510 was purified from *E. coli* and found to migrate as a 49-kD band on SDS-PAGE. As a control, extract from cells containing PET 11d was purified in exactly the same way as YKL510 and is designated PET (fraction V). No protein could be detected in this fraction on a Coomassie-stained SDA-polyacrylamide gel (data not shown). In addition, PET (fraction V) was found to be devoid of nuclease activity.

Analysis of substrate specificity revealed that purified YKL510 cleaved 5' flap structures but not a 3' flap structure or single-stranded DNA. Like FEN-1, YKL510 efficiently cleaved 5' flapped structures independent of flap strand length and failed to cleave 5' pseudo-Y structures. In addition, YKL510 was found to have 5'-3' double-strand-specific exonuclease activity similar to that of FEN-1. The product of YKL510 exonuclease activity was mono- and dinucleotides as determined by high percentage sequencing gels. The similar sequence, structure, and enzymatic activities of these two enzymes indicates that YKL510 is the yeast analog of FEN-1.

Rad2 is homologous to FEN-1 and YKL510 in three major regions. The separation of the N and I regions by the S region in RAD2, however, represents one difference between these two RAD2 family subtypes.

To determine whether the S region of RAD2 can be deleted to give a truncated RAD2 protein that is still a functional nuclease, the RAD2 gene was modified to produce ΔRAD2. Expression of ΔRAD2 from PET 11d produced a 5' flap cleavage activity that was absent to extracts from cells containing PET 11d. ΔRAD2 was purified by use of the standard flap assay to monitor its chromatographic behavior. As a control, a side-by-side purification of extracts from cells containing PET 11d was carried out. On a silver-stained SDA-polyacrylamide gel, 30 ng of ΔRAD2 (fraction V) contained one 53-kD band, the expected size of ΔRAD2 (data not shown).

To further ascertain purity, purified PET (fraction V) was assayed for nuclease activity.

We analyzed the substrate specificities of purified ΔRAD2 and found that it was a structure-specific endonuclease that cleaves 5' flap structures but not 3' flap structures. Like FEN-1 and YKL510, ΔRAD2 also did not cleave 3' pseudo-Y structures (data not shown). A 3' pseudo-Y structure is a 3' flap structure that is missing the $F_{adj}$ strand. Interestingly, ΔRAD2 did cleave 5' pseudo-Y structures.

ΔRAD2 differed from FEN-1 and YKL510 in its ability to act as a 5'-3' double-strand specific exonuclease. FEN-1 and YKL510 exonuclease activities were approximately half as efficient as their respective DNA flap cleavage activities. ΔRAD2, on the other hand, had only a weak 5'-3' exonuclease activity that was 100 times less efficient relative to its flap cleavage activity. Thus, the primary activity of ΔRAD2 appears to be endonucleolytic in nature.

Finally, ΔRAD2 did not cleave single-stranded DNA oligonucleotides. Although ΔRAD2 is most active on flap structures, cleavage of pseudo-Y structures is easily detected in our assay.

The FEN-1 gene is the first characterized DNA structure-specific endonuclease to be cloned from any eukaryote.

All three enzymes cleave 5' flap structures and fail to cleave other DNA structures, including 3' flaps and single-stranded DNA. Unlike FEN-1 and YKL510, ΔRAD2 efficiently cleaves 5' pseudo-Y structures and has only a weak exonuclease activity when compared with its flap endonuclease activity.

FEN-1 is likely involved in the removal of Okazaki fragment primers during replication and in the removal of damaged bases from DNA. *E coli* DNA polymerase I has been shown to be involved in DNA replication and DNA repair (Baker and Kornberg 1992). The intrinsic 5'-3' exonuclease domain of DNA polymerase I (Pol I) has been shown to be absolutely required for both of these functions. In addition, the 5'-3' exonuclease domain has been shown to be a structure-specific endonuclease that cleaves 5' flap structure (Lyamichev et al. 1993). Eukaryotic polymerases, however, do not have an intrinsic 5'-3' exonuclease domain. It has been proposed that this activity is localized to the replication fork by protein-protein interactions with DNA polymerase ε. DNA polymerase ε (Pol ε) has also been shown to be involved in the repair of UV-damaged DNA. Recently, it has been shown that the calf thymus 5'-3' exonuclease also is a flap endonuclease that interacts functionally with DNA Pol ε (Murante et al. 1994). On the basis of the size and enzymatic properties of this enzyme, it is likely to be the bovine analog of murine FEN-1. Thus, the DNA pol ε/FEN-1 complex can be a eukaryotic counterpart to *E. coli* DNA Pol I.

We have shown that deletion of the spacer region of RAD2 does not destroy its nuclease activity. This indicates that the nuclease active site is either in the N,I, or C regions.

On the basis of the enzymatic activities of ΔRAD2 described here, we propose that RAD2 does not recognize single-stranded DNA per se but, instead, recognizes precise branched DNA structures. Furthermore, the orientation-specific cleavage of these structures by ΔRAD2 has enabled us to predict the placement of DNA scissions by RAD2 relative to the damaged base(s).

The inability of ΔRAD2 to cleave 3' pseudo-Y structures or single-stranded DNA and its ability to cleave 5' pseudo-Y structures, therefore, indicates that RAD2 cleaves the damaged strand on the 3' side of the damage.

EXAMPLE 3 Isolation of Human FEN-1 cDNA and Genomic Clones

Materials and Methods

Isolation of human FENI cDNA and genomic clones. The mouse Fen-1 cDNA has been isolated and sequenced previously, supra. This cDNA was used to screen a human genomic phage library (Stratagene 946205) and a human leukemic T-cell cDNA phage library (Clontech HL101078a). The nitrocellulose filters (Schleicher and Schuell) were hybridized in 3× SSC, 1 mM EDTA, 10 mM Tris, pH 8.0, 1× Denhardt's, and 100 μg/ml salmon sperm DNA at 60° C. overnight with $^{32}$P-random primed probe. These filters were washed in 2× SSC and 0.5% SDS at room temperature for 10 min, followed by two 10-min washes at 60° C. in 0.5× SSC and 0.5% SDS.

Somatic cell hybrids and radiation-reduced hybrid cell lines (RRHs). For assignment of Fen-1 gene to mouse chromosome, we used an established panel of 12 Chinese hamster×mouse and 1 rat×mouse somatic cell hybrid lines (Yang-Feng et al., 1986). The hybridization conditions were identical to those that we have used previously (Yang-Feng et al., 1986).

The three somatic cell hybrid cell lines (J1-44, J1-45, J1-46) the 8 radiation-reduced hybrid cell lines (RRHs, R184-1A2, R184-3A1, R184-7C1, R184-5D1, R184-4C2, R185-1B1, and R131-33B1), and the Southern hybridization protocols have been described previously (Gerhard et al., 1992). The cell line DNA was digested with EcoRI, separated by size, immobilized on nylon membranes, and hybridized with a 600-bp fragment of the 5' end of the human cDNA of FEN-1.

Chromosome in situ hybridization. Fluorescence in situ hybridization of peripheral lymphocyte metaphase chromosomes from normal individuals was carried out using biotin-11-dUTP (Sigma) labeled human FEN-1 genomic clones (HG1-1 and HG5-3). HG1-1 (19 kb), HG2-2 (12 kb), and HG5-3 (17 kb) are three independent clones, each of which contains sequences that hybridize with the murine FEN-1 cDNA by Southern blot. Hybridization conditions and washes were as described (Spritz et al., 1991). After the final wash, the slides were counterstained with 30 μl of anti-fade medium (2.3% DABCO, 90% glycerol) containing 200 ng/ml of propidium iodide (PI) and 200 ng/ml DAPI. Slides were analyzed using a Zeiss Axiophot microscope. Results were directly photographed using Kodak Ektachrome ASA 400 color film.

Sequence of cDNA for Human FEN-1

Full-length cDNA for human FEN-1 was isolated from a human leukemic T-cell cDNA phage library. The sequence of human FEN1 is shown in FIG. 1. The identity between the human FEN1 cDNA and the mouse cDNA is 95.3% at the amino acid level and 89% at the nucleotide level. The amino acid similarity is 97.6%. We have confirmed that this human cDNA clone can be overexpressed in *Escherichia coli* to yield a 50-kDa protein with the same endonucleolytic activity that we have recently reported for the murine cDNA (Harrington and Lieber, 1994a; and data not shown).

Isolation of Genomic Clones

Several genomic clones were isolated from the phage library screened using the cDNA of mouse FEN-1 as a probe. Three clones, HG1-1, HG2-2, and HG5-3, were further characterized. The estimated insert sizes of HG1-1, HG2-2, and HG5-3 are 19, 12, and 17 kb, respectively. These three clones contain sequences that hybridize with the cDNA of mouse FEN-1 by Southern blot. With BamHI digestion, using the cDNA of mouse FEN-1 as a probe, the HG1-1, HG2-2, and HG5-3 clones each have one positive fragment of 2.2, 3.0, and 8 kb, respectively. The 2.2- and 8-kb fragments correspond to the two FEN1 fragments observed in the BamHI-digested total human genomic DNA. With EcoRI or HindIII single digest using mouse FEN1 cDNA as a probe, the HG1-1 and HG2-2 clones both have a common 3-kb fragment, and each has a smaller fragment of dissimilar size by EcoRI digest. Other than this, these three clones do not contain the same size fragments upon EcoRI or HindIII digestion. However, the fragment sizes are consistent with the fragments in total human DNA digested with EcoRI or HindIII when probed with the cDNA of mouse FEN-1. Hence, these three clones (HG1-1, -2-2, and -5-3) do contain FEN1 DNA sequences. We were interested in finding out (1) whether these three clones represent different regions of the FEN1 genomic sequence or (2) whether one clone represents the authentic FEN1 gene and the other clones represent a pseudogene or a gene homologous to FEN1. We chose to localize these three clones using FISH.

Chromosomal Assignment of FEN1 in Human

When the biotinylated genomic clone HG1-1 is hybridized to human metaphase chromosome spreads, fluorescent signals are observed on sister chromatids of both homologs of chromosome 1 in 40 cells examined, and DAPI banding indicates that the specific signals are localized to band p22.2. The clone HG2-2 is also localized to chromosome 1p22.2 (data not shown) in 25 cells examined using FISH. FISH analysis and DAPI counterstaining of metaphase spreads hybridized with the biotinylated HG5-3 clone reveal symmetrical fluorescent signals on both homologs of chromosome 11q12-q13.1 in 45 cells examined.

The HG5-3 is the only clone localized to chromosome 11; therefore, we further confirmed the FEN1 localization on human chromosome 11 using hybrids containing all or portions of the human chromosome 11 as the only human material. Using the 5' end of FEN-1 human cDNA as a probe, a 3.9-kb human-specific fragment is observed in EcoRI-digested DNA. This band is absent from the cell line J1-44 (deleted for human chromosome 11q12-q14), but is present in J1-45 and J1-46 (deleted for a portion of human 11q13), indicating that FEN1 is in human chromosomal region 11q12 or 11q13.5-q14. The FEN1-specific band is present in 6 of 8 radiation-reduced hybrids (RRHs). The two cell lines where it is lacking are R185-2C2 and R185-1B1. This segregation pattern is identical to that of pepsinogen Al, which has been localized to human chromosome 11q12 (Gerhard et al., 1992) (data not shown).

Chromosomal Assignment of FEN-1 in Mouse

A Southern blot of BglII-digested DNA from controls and 13 somatic cell hybrid lines containing subsets of mouse chromosomes was hybridized with $^{32}$P-labeled mouse cDNA. A single fragment of 3.8 kb is present in the mouse control DNA, two fragments of 2.5 and 21.5 kb are observed in the Chinese hamster control DNA, and a 8.0-kb band is present in the rat control DNA. The 3.8-kb mouse band is observed in all hybrids containing mouse chromosome 19. All other mouse chromosomes are excluded by at least two discordant hybrids.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
        ( A ) LENGTH: 380 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Gly Ile Gln Gly Leu Ala Lys Leu Ile Ala Asp Val Ala Pro Ser
  1               5                  10                  15

Ala Ile Arg Glu Asn Asp Ile Lys Ser Tyr Phe Gly Arg Lys Val Ala
                 20                  25                  30

Ile Asp Ala Ser Met Ser Ile Tyr Gln Phe Leu Ile Ala Val Arg Gln
             35                  40                  45

Gly Gly Asp Val Leu Gln Asn Glu Glu Gly Glu Thr Thr Ser His Leu
     50                  55                  60

Met Gly Met Phe Tyr Arg Thr Ile Arg Met Met Glu Asn Gly Ile Lys
 65                  70                  75                  80

Pro Val Tyr Val Phe Asp Gly Lys Pro Pro Gln Leu Lys Ser Gly Glu
                 85                  90                  95

Leu Ala Lys Arg Ser Glu Arg Arg Ala Glu Ala Glu Lys Gln Leu Gln
            100                 105                 110

Gln Ala Gln Ala Ala Gly Ala Glu Gly Glu Val Glu Lys Phe Thr Lys
            115                 120                 125

Arg Leu Val Lys Val Thr Lys Gln His Asn Asp Glu Cys Lys His Leu
130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
            165                 170                 175

Thr Glu Asp Met Asp Cys Leu Thr Phe Gly Ser Pro Val Leu Met Arg
            180                 185                 190

His Leu Thr Ala Ser Glu Ala Lys Lys Leu Pro Ile Gln Glu Phe His
        195                 200                 205

Leu Ser Arg Ile Leu Gln Glu Leu Gly Leu Asn Gln Glu Gln Phe Val
    210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
            260                 265                 270

Asn Trp Leu His Lys Glu Ala His Gln Leu Phe Leu Glu Pro Glu Val
            275                 280                 285

Leu Asp Pro Glu Ser Val Glu Leu Lys Trp Ser Glu Pro Asn Glu Glu
```

|     |     |     |     |     |     | 290 |     |     |     |     | 295 |     |     |     |     | 300 |     |     |     |
| --- | --- | --- | --- | --- | --- | --- | --- | --- | --- | --- | --- | --- | --- | --- | --- | --- | --- | --- | --- |
| Glu | Leu | Ile | Lys | Phe | Met | Cys | Gly | Glu | Lys | Gln | Phe | Ser | Glu | Glu | Arg |
| 305 |     |     |     |     | 310 |     |     |     | 315 |     |     |     |     |     | 320 |
| Ile | Arg | Ser | Gly | Val | Lys | Arg | Leu | Ser | Lys | Ser | Arg | Gln | Gly | Ser | Thr |
|     |     |     |     | 325 |     |     |     |     | 330 |     |     |     |     | 335 |     |
| Gln | Gly | Arg | Leu | Asp | Asp | Phe | Phe | Lys | Val | Thr | Gly | Ser | Leu | Ser | Ser |
|     |     |     | 340 |     |     |     |     | 345 |     |     |     |     | 350 |     |     |
| Ala | Lys | Arg | Lys | Glu | Pro | Glu | Pro | Lys | Gly | Ser | Thr | Lys | Lys | Lys | Ala |
|     |     | 355 |     |     |     |     | 360 |     |     |     |     | 365 |     |     |     |
| Lys | Thr | Gly | Ala | Ala | Gly | Lys | Phe | Lys | Arg | Gly | Lys |
|     |     | 370 |     |     |     | 375 |     |     |     | 380 |     |

( 2 ) INFORMATION FOR SEQ ID NO:2:

( i ) SEQUENCE CHARACTERISTICS:
        ( A ) LENGTH: 1144 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| ATGGAATTC | AAGGCCTGGC | CAAACTAATT | GCTGATGTGG | CCCCCAGTGC | CATCCGGGAG | 60 |
| AATGACATCA | AGAGCTACTT | TGGCCGTAAG | GTGGCCATTG | ATGCCTCTAT | GAGCATTTAT | 120 |
| CAGTTCCTGA | TTGCTGTTCG | CCAGGGTGGG | GATGTGCTGC | AGAATGAGGA | GGGTGAGACC | 180 |
| ACCAGCCACC | TGATGGGCAT | GTTCTACCGC | ACCATTCGCA | TGATGGAGAA | CGGCATCAAG | 240 |
| CCCGTGTATG | TCTTTGATGG | CAAGCCGCCA | CAGCTCAAGT | CAGGCGAGCT | GGCCAAACGC | 300 |
| AGTGAGCGGC | GGGCTGAGGC | AGAGAAGCAG | CTGCAGCAGG | CTCAGGCTGC | TGGGGCCGAG | 360 |
| CAGGAGGTGG | AAAAATTCAC | TAAGCGGCTG | GTGAAGGTCA | CTAAGCAGCA | CAATGATGAG | 420 |
| TGCAAACATC | TGCTGAGCCT | CATGGGCATC | CCTTATCTTG | ATGCACCCAG | TGAGGCAGAG | 480 |
| GCCAGCTGTG | CTGCCCTGGT | GAAGGCTGGC | AAAGTCTATG | CTGCGGCTAC | CGAGGACATG | 540 |
| GACTGCCTCA | CCTTCGGCAG | CCCTGTGCTA | ATGCGACACC | TGACTGCCAG | TGAAGCCAAA | 600 |
| AAGCTGCCAA | TCCAGGAATT | CCACCTGAGC | CGGATTCTGC | AGGAGCTGGG | CCTGAACCAG | 660 |
| GAACAGTTTG | TGGATCTGTG | CATCCTGCTA | GGCAGTGACT | ACTGTGAGAG | TATCCGGGGT | 720 |
| ATTGGGCCCA | AGCGGGCTGT | GGACCTCATC | CAGAAGCACA | AGAGCATCGA | GGAGATCGTG | 780 |
| CGGCGACTTG | ACCCCAACAA | GTACCCTGTG | CCAGAAAATT | GGCTCCACAA | GGAGGCTCAC | 840 |
| CAGCTCTTCT | TGGAACCTGA | GGTGCTGGAC | CCAGAGTCTG | TGGAGCTGAA | GTGGAGCGAG | 900 |
| CCAAATGAAG | AAGAGCTGAT | CAAGTTCATG | TGTGGTGAAA | AGCAGTTCTC | TGAGGAGCGA | 960 |
| ATCCGCAGTG | GGGTCAAGAG | GCTGAGTAAG | AGCCGCCAAG | GCAGCACCCA | GGGCCGCCTG | 1020 |
| GATGATTTCT | TCAAGGTGAC | CGGCTCACTC | TCTTCAGCTA | AGCGCAAGGA | GCCAGAACCC | 1080 |
| AAGGGATCCA | CTAAGAAGAA | GGCAAAGACT | GGGGCAGCAG | GAAGTTTAA | AAGGGGAAAA | 1140 |
| TAAA | | | | | | 1144 |

( 2 ) INFORMATION FOR SEQ ID NO:3:

( i ) SEQUENCE CHARACTERISTICS:
        ( A ) LENGTH: 377 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

| Met | Gly | Ile | His | Gly | Leu | Ala | Lys | Leu | Ile | Ala | Asp | Val | Ala | Pro | Ser |
| 1 | | | | 5 | | | | | 10 | | | | | 15 | |

| Ala | Ile | Arg | Glu | Asn | Asp | Ile | Lys | Ser | Tyr | Phe | Gly | Arg | Lys | Val | Ala |
| | | | | 20 | | | | 25 | | | | | 30 | | |

| Ile | Asp | Ala | Ser | Met | Ser | Ile | Tyr | Gln | Phe | Leu | Ile | Ala | Val | Arg | Gln |
| | | | 35 | | | | 40 | | | | | 45 | | | |

| Gly | Gly | Asp | Val | Leu | Gln | Asn | Glu | Glu | Gly | Glu | Thr | Thr | Ser | Leu | Met |
| | 50 | | | | | 55 | | | | | 60 | | | | |

| Gly | Met | Phe | Tyr | Arg | Thr | Ile | Arg | Met | Glu | Asn | Gly | Ile | Lys | Pro | Val |
| 65 | | | | | 70 | | | | | 75 | | | | | 80 |

| Tyr | Val | Phe | Asp | Gly | Lys | Pro | Pro | Gln | Leu | Lys | Ser | Gly | Glu | Leu | Ala |
| | | | | 85 | | | | | 90 | | | | | 95 | |

| Lys | Arg | Ser | Glu | Arg | Arg | Ala | Glu | Ala | Glu | Lys | Gln | Leu | Gln | Gln | Ala |
| | | | | 100 | | | | 105 | | | | | 110 | | |

| Gln | Glu | Ala | Gly | Met | Glu | Glu | Val | Glu | Lys | Phe | Thr | Lys | Arg | Leu | Val |
| | | | 115 | | | | 120 | | | | | 125 | | | |

| Lys | Val | Thr | Lys | Gln | His | Asn | Asp | Glu | Cys | Lys | His | Leu | Leu | Ser | Leu |
| | | 130 | | | | | 135 | | | | | 140 | | | |

| Met | Gly | Ile | Pro | Tyr | Leu | Asp | Ala | Pro | Ser | Glu | Ala | Glu | Ala | Ser | Cys |
| 145 | | | | | 150 | | | | | 155 | | | | | 160 |

| Ala | Ala | Leu | Ala | Lys | Ala | Gly | Lys | Val | Tyr | Ala | Ala | Ala | Thr | Glu | Asp |
| | | | | 165 | | | | | 170 | | | | | 175 | |

| Met | Asp | Cys | Leu | Thr | Phe | Gly | Ser | Pro | Val | Leu | Met | Arg | His | Leu | Thr |
| | | | | 180 | | | | 185 | | | | | 190 | | |

| Ala | Ser | Glu | Ala | Lys | Lys | Leu | Pro | Ile | Gln | Glu | Phe | His | Leu | Ser | Arg |
| | | | 195 | | | | | 200 | | | | | 205 | | |

| Val | Leu | Gln | Glu | Leu | Gly | Leu | Asn | Gln | Glu | Gln | Phe | Val | Asp | Leu | Cys |
| | | | 210 | | | | | 215 | | | | | 220 | | |

| Ile | Leu | Leu | Gly | Ser | Asp | Tyr | Cys | Glu | Ser | Ile | Arg | Gly | Ile | Gly | Ala |
| 225 | | | | | 230 | | | | | 235 | | | | | 240 |

| Lys | Arg | Ala | Val | Asp | Leu | Ile | Gln | Lys | His | Lys | Ser | Ile | Glu | Glu | Ile |
| | | | | 245 | | | | | 250 | | | | | 255 | |

| Val | Arg | Arg | Leu | Asp | Pro | Ser | Lys | Tyr | Pro | Val | Pro | Glu | Asn | Trp | Leu |
| | | | | 260 | | | | 265 | | | | | 270 | | |

| His | Lys | Glu | Ala | Gln | Gln | Leu | Phe | Leu | Glu | Pro | Glu | Val | Val | Asp | Pro |
| | | | 275 | | | | | 280 | | | | | 285 | | |

| Glu | Ser | Val | Glu | Leu | Lys | Trp | Ser | Glu | Pro | Asn | Glu | Glu | Glu | Leu | Val |
| | | 290 | | | | | 295 | | | | | 300 | | | |

| Lys | Phe | Met | Cys | Gly | Glu | Lys | Gln | Phe | Ser | Glu | Glu | Arg | Ile | Arg | Ser |
| 305 | | | | | 310 | | | | | 315 | | | | | 320 |

| Gly | Val | Lys | Arg | Leu | Ser | Lys | Ser | Arg | Gln | Gly | Ser | Thr | Gln | Gly | Arg |
| | | | | 325 | | | | | 330 | | | | | 335 | |

| Leu | Asp | Asp | Phe | Phe | Lys | Val | Thr | Gly | Ser | Leu | Ser | Ser | Ala | Lys | Arg |
| | | | 340 | | | | 345 | | | | | 350 | | | |

| Lys | Glu | Pro | Glu | Pro | Lys | Gly | Ser | Ala | Lys | Lys | Lys | Ala | Lys | Thr | Gly |
| | | | 355 | | | | 360 | | | | | 365 | | | |

| Gly | Ala | Gly | Lys | Phe | Arg | Arg | Gly | Lys |
| | | 370 | | | | 375 | | |

( 2 ) INFORMATION FOR SEQ ID NO:4:

( i ) SEQUENCE CHARACTERISTICS:
       ( A ) LENGTH: 1930 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

| | | | | | | |
|---|---|---|---|---|---|---|
| ATGGAATTC | ACGGCCTTGC | CAAACTAATT | GCTGATGTGG | CCCCCAGTGC | CATCCGTGAG | 60 |
| AATGACATCA | AGAGCTACTT | TGGTCGTAAA | GTGGCCATCG | ATGCCTCCAT | GAGCATCTAC | 120 |
| CAGTTCCTGA | TTGCTGTTCG | TCAGGGTGGG | GATGTGCTGC | AGAACGAGGA | GGGTGAGACC | 180 |
| ACCAGCCTGA | TGGGCATGTT | ATGGCAAACC | ATCCGCATGG | AGAATGGCAT | CAAGCCTGTG | 240 |
| TACGTCTTTG | ATGGCAAACC | ACCACAGCTG | AAGTCAGGCG | AGCTGGCCAA | GCGCAGTGAG | 300 |
| AGGCGCGCCG | AGGCTGAGAA | GCAACTGCAG | CAGGCTCAGG | AGGCTGGGAT | GGAGGAGGAG | 360 |
| GTGGAGAAGT | TCACCAAGAG | GCTCGTGAAG | GTCACCAAGC | AACACAATGA | TGAGTGCAAA | 420 |
| CACCTCGTGA | GCCTCATGGG | CATCCCTTAC | CTTGATGCAC | CCAGCGAGGC | AGAGGCCAGC | 480 |
| TGTGCTGCCC | TGGCAAAGGC | TGGCAAAGTC | TATGCTGCGG | CCACGGAGGA | CATGGACTGC | 540 |
| CTCACTTTTG | GCAGCCCCGT | GCTAATGCGA | CACTTAACTG | CCAGTGAGGC | CAAGAAGCTG | 600 |
| CCCATCCAAG | AGTTCCATCT | GAGCCGCGTC | CTGCAGGAGC | TGGGTCTGAA | CCAGGAGCAG | 660 |
| TTTGTGGATC | TGTGCATCCT | GCTGGGTAGC | GACTACTGCG | AGAGCATCCG | TGGCATTGGC | 720 |
| GCCAAGCGGG | CTGTGGATCT | CATCCAGAAA | CATAAGAGCA | TCGAGGAGAT | CGTGAGGCGG | 780 |
| CTGGACCCCA | GCAAGTACCC | CGTTCCAGAG | AACTGGCTCC | ACAAGGAAGC | CCAGCAGCTC | 840 |
| TTCCTGGAGC | CAGAAGTAGT | GGACCCAGAG | TCTGTGGAGC | TGAAGTGGAG | CGAGCCAAAT | 900 |
| GAAGAAGAGT | TGGTCAAATT | TATGTGTGGT | GAAAAGCAGT | TTTCTGAAGA | GCGAATTCGC | 960 |
| AGTGGGGTCA | AGCGGCTGAG | TAAGAGCCGC | CAGGGCAGCA | CCCAGGGACG | CCTCGATGAT | 1020 |
| TTCTTCAAGG | TGACAGGCTC | ACTCTCCTCA | GCTAAGCGCA | AGGAGCCAGA | ACCCAAGGGG | 1080 |
| CCTGCTAAGA | AGAAAGCAAA | GACTGGGGGA | GCGGGGAAGT | TCCGAAGGGG | AAAATAAACC | 1140 |
| TGTCCTTCCC | CTCCACTGTC | CTTGACCCCA | GGCTGTCTAT | CTGTTTTGTA | CCCTGCGCTG | 1200 |
| CAGCACATCC | CTCTTGTCCC | TCGTCTTGAG | GAGAGTTCAT | TGCTTCCAGC | GCTCGCCTTC | 1260 |
| AGAGCTTTCC | CTCTCTTGAC | CCTGTGGCAG | GAAGGCCGTA | GCTCTGCTTT | TTCTCATTTT | 1320 |
| TAGCTCAGGA | AAGATGTCAG | GCTCAAACCA | CTTCTCAGGT | TAATGGACAC | TGTAGTCATT | 1380 |
| GTTCTGTGCA | ACTGCGAGCA | ATGTCTTAAG | GAAGAAGAAG | ATAAAGCCGG | GAGCGAGGCT | 1440 |
| GGAGATAGTT | TCCCAGCTGG | CCAGCTGGTG | GAGGAGAGGT | GACTAGAACC | TGACTGACTA | 1500 |
| CTGCTCCTTC | TAATTTCACT | GTCCCTGAAA | GATGCCCATC | AGCCTGGGAT | TCGCTGATGG | 1560 |
| AAGAACTGCA | AAGAGACGCA | GCAGAGAGAA | GTCTGGCTGA | CAACAGATTT | AGTACTGACC | 1620 |
| AGCTGATTTT | TGTGGGCAGA | AATTTGAACT | TGCTGCCTGC | TGAGTCCAGT | AGTTGTGCAG | 1680 |
| GGAGTGAGAT | GGCAGTGTTT | AAGTTTTGAT | TTGTAGTTTT | TTGTTTTTGT | CTCTCCCCTC | 1740 |
| TCCAGTGTTG | GGGATTGACC | CCAGGGCAAA | GGCATTAAGT | GTGCCACTGA | CCTGTGCCTC | 1800 |
| CAAGTGATGT | TCTGACAGCC | TTTCTGAGGC | AATCAATTGA | ATTGAGGTTT | TGGGAGAAGA | 1860 |
| AACTGTTGTT | CATAGGCTAT | TTCTATTTTA | AAAGATGTGA | AGAGAAAAAA | AAAACAATAA | 1920 |
| AATTATAAAA | | | | | | 1930 |

(2) INFORMATION FOR SEQ ID NO:5:

(i) SEQUENCE CHARACTERISTICS:
(A) LENGTH: 382 amino acids
(B) TYPE: amino acid (C) STRANDEDNESS: single
(D) TOPOLOGY: linear (ii) MOLECULE TYPE: protein (xi) SEQUENCE DESCRIPTION: SEQ ID NO:5:

```
Met Gly Ile Lys Gly Leu Asn Ala Ile Ile Ser Glu His Val Pro Ser
  1               5                  10                  15
Ala Ile Arg Lys Ser Asp Ile Lys Ser Phe Phe Gly Arg Lys Val Ala
                 20                  25                  30
Ile Asp Ala Ser Met Ser Leu Tyr Gln Phe Leu Ile Ala Val Arg Gln
             35                  40                  45
Gln Asp Gly Gly Gln Leu Thr Asn Glu Ala Gly Glu Thr Thr Ser His
         50                  55                  60
Leu Met Gly Met Phe Tyr Arg Thr Leu Arg Met Ile Asp Asn Gly Ile
 65                  70                  75                  80
Lys Pro Cys Tyr Val Phe Asp Gly Lys Pro Pro Asp Leu Lys Ser His
                 85                  90                  95
Glu Leu Thr Lys Arg Ser Ser Arg Arg Val Glu Thr Glu Lys Lys Leu
                100                 105                 110
Ala Glu Ala Thr Thr Glu Leu Glu Lys Met Lys Gln Glu Arg Arg Leu
            115                 120                 125
Val Lys Val Ser Lys Glu His Asn Glu Glu Ala Lys Lys Leu Leu Gly
        130                 135                 140
Leu Met Gly Ile Pro Tyr Ile Ile Ala Pro Thr Glu Ala Glu Ala Gln
145                 150                 155                 160
Cys Ala Glu Leu Ala Lys Lys Gly Lys Val Tyr Ala Ala Ala Ser Glu
                165                 170                 175
Asp Met Asp Thr Leu Cys Tyr Arg Thr Pro Phe Leu Leu Arg His Leu
            180                 185                 190
Thr Phe Ser Glu Ala Lys Lys Glu Pro Ile His Glu Ile Asp Thr Glu
        195                 200                 205
Leu Val Leu Arg Gly Leu Asp Leu Thr Ile Glu Gln Phe Val Asp Leu
        210                 215                 220
Cys Ile Met Leu Gly Cys Asp Tyr Cys Glu Ser Ile Arg Gly Val Gly
225                 230                 235                 240
Pro Val Thr Ala Leu Lys Leu Ile Lys Thr His Gly Ser Ile Glu Lys
                245                 250                 255
Ile Val Glu Phe Ile Glu Ser Gly Glu Ser Asn Asn Thr Lys Trp Lys
            260                 265                 270
Ile Pro Glu Asp Trp Pro Tyr Lys Gln Ala Arg Met Leu Phe Leu Asp
        275                 280                 285
Pro Glu Val Ile Asp Gly Asn Glu Ile Asn Leu Lys Trp Ser Pro Pro
    290                 295                 300
Lys Glu Lys Glu Leu Ile Glu Tyr Leu Cys Asp Asp Lys Lys Phe Ser
305                 310                 315                 320
Glu Glu Arg Val Lys Ser Gly Ile Ser Arg Leu Lys Lys Gly Leu Lys
                325                 330                 335
Ser Gly Ile Gln Gly Arg Leu Asp Gly Phe Phe Gln Val Val Pro Lys
            340                 345                 350
Thr Lys Glu Gln Leu Ala Ala Ala Ala Lys Arg Ala Gln Glu Asn Lys
        355                 360                 365
Lys Leu Asn Lys Asn Lys Asn Lys Val Thr Lys Gly Arg Arg
        370                 375                 380
```

( 2 ) INFORMATION FOR SEQ ID NO:6:

( i ) SEQUENCE CHARACTERISTICS:
        ( A ) LENGTH: 1149 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
ATGGGTATTA AAGGTTTGAA TGCAATTATA TCGGAACATG TTCCCTCTGC TATCAGGAAA      60
AGCGATATCA AGAGCTTTTT TGGCAGAAAG GTTGCCATCG ATGCCTCTAT GTCTCTATAT     120
CAGTTTTTAA TTGCTGTAAG ACAGCAAGAC GGTGGGCAGT TGACCAATGA AGCCGGTGAA     180
ACAACGTCAC ACTTGATGGG TATGTTTTAT AGGACACTGA GAATGATTGA TAACGGTATC     240
AAGCCTTGTT ATGTCTTCGA CGGCAAACCT CCAGCTTTGA AATCTCATGA GTTGACAAAG     300
CGGTCTTCAA GAAGGGTGGA AACAGAAAAA AAACTGGCAG AGGCAACAAC AGAATTGGAA     360
AAGATGAAGC AAGAAAGAAG ATTGTTGAAG GTCTCAAAAG AGCATAATGA AGAAGCCCAA     420
AAATTACTAG GACTAATGGG AATCCCATAT ATAATAGCGC CAACGGAAGC TGAGGCTCAA     480
TGTGCTGAGT TGGCAAAGAA GGGAAAGGTG TATGCCGCAG CAAGTGAAGA TATGGACACA     540
CTCTGTTATA GAACACCCTT CTTGTTGAGA CATTTGACTT TTTCAGAGGC CAAGAAGGAA     600
CCGATTCACG AAATAGATAC TGAATTAGTT TTGAGAGGAC TCGACTTGAC AATAGAGCAG     660
TTTGTTGATC TTTGCATAAT GCTTGGTTGT GACTACTGTG AAAGCATCAG AGGTGTTGGT     720
CCAGTGACAG CCTTAAAATT GATAAAAACG CATGGATCCA TCGAAAAAAT CGTGGAGTTT     780
ATTGAATCTG GGGAGTCAAA CAACACTAAA TGGAAAATCC CAGAAGACTG GCCTTACAAA     840
CAAGCAAGAA TGCTGTTTCT TGACCCTGAA GTTATAGATG GTAACGAAAT AAACTTGAAA     900
TGGTCGCCAC CAAAGGAGAA GGAACTTATC GAGTATTTAT GTGATGATAA GAAATTCAGT     960
GAAGAAAGAG TTAAATCTGG TATATCAAGA TTGAAAAAAG GCTTGAAATC TGGCATTCAG    1020
GGTAGGTTAG ATGGGTTCTT CCAAGTGGTG CCTAAGACAA AGGAACAGCT GGCTGCTGCG    1080
GCGAAAAGAG CACAAGAAAA TAAAAAATTG AACAAAAATA AGAATAAAGT CACAAAGGGA    1140
AGAAGATGA                                                          1149
```

( 2 ) INFORMATION FOR SEQ ID NO:7:

( i ) SEQUENCE CHARACTERISTICS:
        ( A ) LENGTH: 386 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Met Gly His Val Ser Phe Trp Asp Ile Ala Gly Pro Thr Ala Arg Pro
 1               5                  10                  15

Val Arg Leu Glu Ser Leu Glu Asp Lys Arg Met Ala Val Asp Ala Ser
            20                  25                  30

Ile Trp Ile Tyr Gln Phe Leu Lys Ala Val Arg Asp Gln Glu Gly Asn
        35                  40                  45

Ala Val Lys Asn Ser His Ile Thr Gly Phe Phe Arg Arg Ile Cys Lys
    50                  55                  60

Leu Leu Tyr Phe Gly Ile Arg Pro Val Phe Phe Asp Gly Gly Val
65                  70                  75                  80
```

| | | | | | | | | | | | | | | |
|---|---|---|---|---|---|---|---|---|---|---|---|---|---|---|
| Pro | Val | Leu | Lys | Arg<br>85 | Glu | Thr | Ile | Arg | Gln<br>90 | Arg | Lys | Glu | Arg<br>95 | Gln |
| Gly | Lys | Arg | Glu<br>100 | Ser | Ala | Lys | Ser | Thr<br>105 | Ala | Arg | Lys | Leu | Gln<br>110 | Gln | Gln |
| Met | Lys | Asp<br>115 | Lys | Arg | Asp | Ser | Asp<br>120 | Glu | Val | Thr | Met | Asp<br>125 | Met | Ile | Lys |
| Glu | Val<br>130 | Gln | Glu | Leu | Leu | Ser<br>135 | Arg | Phe | Gly | Ile | Pro<br>140 | Tyr | Ile | Thr | Ala |
| Pro<br>145 | Met | Glu | Ala | Glu | Gln<br>150 | Cys | Ala | Glu | Leu | Leu<br>155 | Gln | Leu | Asn | Leu | Val<br>160 |
| Asp | Gly | Ile | Ile | Thr<br>165 | Asp | Asp | Ser | Asp | Val<br>170 | Phe | Leu | Phe | Gly | Gly<br>175 | Thr |
| Lys | Ile | Tyr | Lys<br>180 | Asn | Met | Phe | His | Glu<br>185 | Lys | Asn | Tyr | Val | Glu<br>190 | Phe | Tyr |
| Asp | Ala | Glu<br>195 | Ser | Ser | Ile | Leu | Lys<br>200 | Leu | Leu | Gly | Leu | Asp<br>205 | Arg | Lys | Asn |
| Met | Ile<br>210 | Glu | Leu | Ala | Gln | Leu<br>215 | Leu | Gly | Ser | Asp | Tyr<br>220 | Thr | Asn | Gly | Leu |
| Lys<br>225 | Gly | Met | Gly | Pro | Val<br>230 | Ser | Ser | Ile | Glu | Val<br>235 | Ile | Ala | Glu | Phe | Gly<br>240 |
| Asn | Leu | Lys | Asn | Phe<br>245 | Lys | Asp | Trp | Tyr | Asn<br>250 | Asn | Gly | Gln | Phe | Asp<br>255 | Lys |
| Arg | Lys | Gln | Glu<br>260 | Thr | Glu | Asn | Lys | Phe<br>265 | Glu | Lys | Asp | Leu | Arg<br>270 | Lys | Lys |
| Leu | Val<br>275 | Asn | Asn | Glu | Ile | Leu<br>280 | Leu | Asp | Asp | Phe | Pro<br>285 | Ser | Val | Met |
| Val | Tyr<br>290 | Asp | Ala | Tyr | Met | Arg<br>295 | Pro | Glu | Val | Asp | His<br>300 | Asp | Thr | Thr | Pro |
| Phe<br>305 | Val | Trp | Gly | Val | Pro<br>310 | Asp | Leu | Asp | Met | Leu<br>315 | Arg | Ser | Phe | Met | Lys<br>320 |
| Thr | Gln | Leu | Gly | Trp<br>325 | Pro | His | Glu | Lys | Ser<br>330 | Asp | Glu | Ile | Leu | Ile<br>335 | Pro |
| Leu | Ile | Arg | Asp<br>340 | Val | Asn | Lys | Arg | Lys<br>345 | Lys | Lys | Gly | Lys | Gln<br>350 | Lys | Arg |
| Ile | Asn | Glu<br>355 | Phe | Phe | Pro | Arg | Glu<br>360 | Tyr | Ile | Ser | Gly | Asp<br>365 | Lys | Lys | Leu |
| Asn | Thr<br>370 | Ser | Lys | Arg | Ile | Ser<br>375 | Thr | Ala | Thr | Gly | Lys<br>380 | Leu | Lys | Lys | Arg |
| Lys<br>385 | Met | | | | | | | | | | | | | | |

( 2 ) INFORMATION FOR SEQ ID NO:8:

( i ) SEQUENCE CHARACTERISTICS:
        ( A ) LENGTH: 1161 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
ATGGGTGTGC ATTCATTTTG GGATATTGCA GGTCCTACGG CAAGACCGGT CAGGCTGGAA         60

TCCTTGGAAG ATAAGAGAAT GGCAGTAGAT GCCTCCATTT GGATATATCA GTTTTTGAAA        120

GCTGTCCGTG ATCAGGAGGG GAATGCAGTG AAGAATTCTC ATATTACTGG GTTCTTTAGA        180

AGAATTTGTA AGCTATTATA CTTTGGCATT AGGCCGGTAT TCGTCTTTGA TGGTGGTGTG        240
```

| | | | | | |
|---|---|---|---|---|---|
| CCCGTATTGA | AAAGGGAAAC | AATACGGCAG | AGGAAAGAAA | GAAGACAGGG | AAAACGAGAG | 300 |
| AGTGCGAAAT | CCACCGCTAG | GAAGCTGCAA | CAACAGATGA | AGGATAAAAG | AGATTCGGAT | 360 |
| GAGGTAACTA | TGGATATGAT | CAAAGAAGTG | CAAGAATTAC | TATCGAGGTT | TGGAATCCCC | 420 |
| TATATCACTG | CGCCTATGGA | AGCTGAAGCA | CAGTGTGCGG | AATTGTTACA | ACTAAACCTT | 480 |
| GTCGATGGTA | TAATTACCGA | TGACAGTGAT | GTTTCCTAT | TTGGAGGTAC | AAAGATCTAC | 540 |
| AAAAATATGT | TCCACGAAAA | GAACTATGTT | GAATTTATG | ATGCGGAATC | TATTTAAAA | 600 |
| TTATTGGGCT | TGGATAGAAA | GAATATGATT | GAGTTGGCAC | AGCTTTAGG | GAGCGATTAC | 660 |
| ACGAATGGAT | TGAAGGGTAT | GGGTCCCGTT | TCAAGCATTG | AAGTGATTGC | AGAATTTGGA | 720 |
| AACCTAAAAA | ATTTTAAAGA | CTGGTATAAT | AATGGGCAGT | TTGATAAACG | TAAGCAAGAA | 780 |
| ACGGAAAATA | AATTTGAAAA | AGACCTGAGA | AAAAACTGG | TAAATAACGA | AATTATCTTA | 840 |
| GATGATGATT | TTCCTAGCGT | CATGGTTTAT | GATGCGTATA | TGAGACCAGA | AGTCGATCAC | 900 |
| GATACCACGC | CGTTTGTTTG | GGGGGTACCA | GATCTCGATA | TGCTTCGTTC | ATTCATGAAG | 960 |
| ACTCAACTAG | GTTGGCCACA | CGAAAAGTCT | GATGAAATTC | TCATTCCCTT | AATTAGAGAT | 1020 |
| GTTAATAAAC | GCAAAAAGAA | GGGGAAGCAA | AAAAGGATTA | ATGAATTTTT | TCCAAGGGAG | 1080 |
| TACATATCTG | GTGATAAGAA | GCTCAATACA | AGTAAGAGAA | TTTCAACCGC | AACAGGTAAA | 1140 |
| CTAAAGAAAA | GAAAGATGTA | A | | | | 1161 |

( 2 ) INFORMATION FOR SEQ ID NO:9:

( i ) SEQUENCE CHARACTERISTICS:
        ( A ) LENGTH: 2033 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 104..1237

( x i ) SEQUENCE DESCRIPTION: SEQ ID NO:9:

TCGCGGAAGC TGTGAAAGCG GCAGACGGAA CAGCACCGGG CTAGCCCGGC TTTGGCCATT  60

CTGCTCCGAA CATTCCTATT GTTGCCATTG CTCCTGTGCT ACC ATG GAA ATT CAC  115
                                                                                                    Met Glu Ile His
                                                                                                                   1

GGC CTT GCC AAA CTA ATT GCT GAT GTG GCC CCC AGT GCC ATC CGT GAG  163
Gly Leu Ala Lys Leu Ile Ala Asp Val Ala Pro Ser Ala Ile Arg Glu
 5                       10                    15                    20

AAT GAC ATC AAG AGC TAC TTT GGT CGC AAA GTG GCC ATC GAT GCC TCC  211
Asn Asp Ile Lys Ser Tyr Phe Gly Arg Lys Val Ala Ile Asp Ala Ser
                  25                    30                    35

ATG AGC ATC TAC CAG TTC CTG ATT GCT GTT CGT CAG GGT GGG GAT GTG  259
Met Ser Ile Tyr Gln Phe Leu Ile Ala Val Arg Gln Gly Gly Asp Val
            40                    45                    50

CTG CAG AAC GAG GAG GGT GAG ACC ACC AGC CTG ATG GGC ATG TTC TAC  307
Leu Gln Asn Glu Glu Gly Glu Thr Thr Ser Leu Met Gly Met Phe Tyr
     55                    60                    65

CGT ACC ATG CGC ATG GAG AAT GGC ATC AAG CCT GTG TAC GTC TTT GAT  355
Arg Thr Met Arg Met Glu Asn Gly Ile Lys Pro Val Tyr Val Phe Asp
            70                    75                    80

GGC AAA CCA CCA CAG CTG AAG TCA GGC GAG CTG GCC AAG CGC AGT GAG  403
Gly Lys Pro Pro Gln Leu Lys Ser Gly Glu Leu Ala Lys Arg Ser Glu
 85                       90                    95                   100

-continued

| | | | | | | | | | | | | | | | | |
|---|---|---|---|---|---|---|---|---|---|---|---|---|---|---|---|---|
| AGG | CGC | GCC | GAG | GCT | GAG | AAG | CAA | CTG | CAG | CAG | GCT | CAG | CAG | GCT | GGG | 451 |
| Arg | Arg | Ala | Glu | Ala | Glu | Lys | Gln | Leu | Gln | Gln | Ala | Gln | Gln | Ala | Gly | |
| | | | | 105 | | | | 110 | | | | | | 115 | | |
| ATG | GAG | GAG | GAG | GTG | GAG | AAG | TTC | ACC | AAG | AGG | CTC | GTG | AAG | GTC | ACC | 499 |
| Met | Glu | Glu | Glu | Val | Glu | Lys | Phe | Thr | Lys | Arg | Leu | Val | Lys | Val | Thr | |
| | | | 120 | | | | | 125 | | | | | 130 | | | |
| AAG | CAA | CAC | AAT | GAT | GAG | TGC | AAA | CAC | CTG | CTG | AGC | CTC | ATG | GGC | ATC | 547 |
| Lys | Gln | His | Asn | Asp | Glu | Cys | Lys | His | Leu | Leu | Ser | Leu | Met | Gly | Ile | |
| | | 135 | | | | | 140 | | | | | 145 | | | | |
| CCT | TAC | CTT | GAT | GCA | CCC | AGC | GAG | GCA | GAG | GCC | AGC | TGT | GCT | GCC | CTG | 595 |
| Pro | Tyr | Leu | Asp | Ala | Pro | Ser | Glu | Ala | Glu | Ala | Ser | Cys | Ala | Ala | Leu | |
| | 150 | | | | | 155 | | | | | 160 | | | | | |
| GCA | AAG | GCT | GGC | AAA | GTC | TAT | GCT | GCG | GCC | ACG | GAG | GAC | ATG | GAC | TGC | 643 |
| Ala | Lys | Ala | Gly | Lys | Val | Tyr | Ala | Ala | Ala | Thr | Glu | Asp | Met | Asp | Cys | |
| 165 | | | | | 170 | | | | | 175 | | | | | 180 | |
| CTC | ACT | TTT | GGC | AGC | CCC | GTG | CTA | ATG | CGA | CAC | TTA | ACT | GCC | AGT | GAG | 691 |
| Leu | Thr | Phe | Gly | Ser | Pro | Val | Leu | Met | Arg | His | Leu | Thr | Ala | Ser | Glu | |
| | | | | 185 | | | | | 190 | | | | | 195 | | |
| GCC | AAG | AAG | CTG | CCC | ATC | CAA | GAG | TTC | CAT | CTG | AGC | CGC | GTC | CTG | CAG | 739 |
| Ala | Lys | Lys | Leu | Pro | Ile | Gln | Glu | Phe | His | Leu | Ser | Arg | Val | Leu | Gln | |
| | | | 200 | | | | | 205 | | | | | 210 | | | |
| GAG | CTG | GGT | CTG | AAC | CAG | GAG | CAG | TTT | GTG | GAT | CTG | TGC | ATC | CTG | CTG | 787 |
| Glu | Leu | Gly | Leu | Asn | Gln | Glu | Gln | Phe | Val | Asp | Leu | Cys | Ile | Leu | Leu | |
| | | 215 | | | | | 220 | | | | | 225 | | | | |
| GGT | AGC | GAC | TAC | TGC | GAG | AGC | ATC | CGT | GGC | ATT | GGC | GCC | AAG | CGG | GCT | 835 |
| Gly | Ser | Asp | Tyr | Cys | Glu | Ser | Ile | Arg | Gly | Ile | Gly | Ala | Lys | Arg | Ala | |
| | 230 | | | | | 235 | | | | | 240 | | | | | |
| GTG | GAT | CTC | ATC | CAG | AAA | CAT | AAG | AGC | ATC | GAG | GAG | ATC | GTG | AGG | CGG | 883 |
| Val | Asp | Leu | Ile | Gln | Lys | His | Lys | Ser | Ile | Glu | Glu | Ile | Val | Arg | Arg | |
| 245 | | | | | 250 | | | | | 255 | | | | | 260 | |
| CTG | GAC | CCC | AGC | AAG | TAC | CCC | GTT | CCA | GAG | AAC | TGG | CTC | CAC | AAG | GAA | 931 |
| Leu | Asp | Pro | Ser | Lys | Tyr | Pro | Val | Pro | Glu | Asn | Trp | Leu | His | Lys | Glu | |
| | | | | 265 | | | | | 270 | | | | | 275 | | |
| GCC | CAG | CAG | CTC | TTC | CTG | GAG | CCA | GAA | GTA | GTG | GAC | CCA | GAG | TCT | GTG | 979 |
| Ala | Gln | Gln | Leu | Phe | Leu | Glu | Pro | Glu | Val | Val | Asp | Pro | Glu | Ser | Val | |
| | | | 280 | | | | | 285 | | | | | 290 | | | |
| GAG | CTG | AAG | TGG | AGC | GAG | CCA | AAT | GAA | GAA | GAG | TTG | GTC | AAA | TTT | ATG | 1027 |
| Glu | Leu | Lys | Trp | Ser | Glu | Pro | Asn | Glu | Glu | Glu | Leu | Val | Lys | Phe | Met | |
| | | 295 | | | | | 300 | | | | | 305 | | | | |
| TGT | GGT | GAA | AAG | CAG | TTT | TTT | GAA | GAG | CGA | ATT | CGC | AGT | GGG | GTC | AAG | 1075 |
| Cys | Gly | Glu | Lys | Gln | Phe | Phe | Glu | Glu | Arg | Ile | Arg | Ser | Gly | Val | Lys | |
| | 310 | | | | | 315 | | | | | 320 | | | | | |
| CGG | CTG | AGT | AAG | AGC | CGC | CAG | GGC | AGC | ACC | CAG | GGA | CGC | CTC | GAT | GAT | 1123 |
| Arg | Leu | Ser | Lys | Ser | Arg | Gln | Gly | Ser | Thr | Gln | Gly | Arg | Leu | Asp | Asp | |
| 325 | | | | | 330 | | | | | 335 | | | | | 340 | |
| TTC | TTC | AAG | GTG | ACA | GGC | TCA | CTC | TCC | TCA | GCT | AAG | CGC | AAG | GAG | CCA | 1171 |
| Phe | Phe | Lys | Val | Thr | Gly | Ser | Leu | Ser | Ser | Ala | Lys | Arg | Lys | Glu | Pro | |
| | | | | 345 | | | | | 350 | | | | | 355 | | |
| GAA | CCC | AAG | GGG | CCT | GCT | AAG | AAG | AAA | GCA | AAG | ACT | GGG | GGA | GCG | GGG | 1219 |
| Glu | Pro | Lys | Gly | Pro | Ala | Lys | Lys | Lys | Ala | Lys | Thr | Gly | Gly | Ala | Gly | |
| | | | 360 | | | | | 365 | | | | | 370 | | | |
| AAG | TTC | CGA | AGG | GGA | AAA | TAAACCTGTC | CTTCCCCTCC | ACTGTCCTTG | | | | | | | | 1267 |
| Lys | Phe | Arg | Arg | Gly | Lys | | | | | | | | | | | |
| | | 375 | | | | | | | | | | | | | | |

| | | | | | |
|---|---|---|---|---|---|
| ACCCCAGGCT | GTCTATCTGT | TTTGTACCCT | CGGCTGCAGC | ACATCCCTCT | TGTCCCTCGT | 1327 |
| CTTGAGGAGA | GTTCATTGCT | TCCAGCGCTG | CCCTTCAGAG | CTTTCCCTCT | CTTGACCCTG | 1387 |
| TGGCAGGAAG | GCCGTAGCTC | TGCTTTTTCT | CATTTTTAGC | TCAGGAAAGA | TGTCAGGCTC | 1447 |
| AAACCACTTC | TCAGGTTAAT | GGACACTGTA | GTCATTGTTC | TGTGCAACTG | CGAGCAATGT | 1507 |

```
CTTAAGGAAG  AAGAAGATAA  AGCCGGGAGC  GAGGCTGGAG  ATAGTTTCCC  AGCTGGCCAG      1567

CTGGTGGAGG  AGAGGTGACT  AGAACCTGAC  TGACTACTGC  TCCTTCTAAT  TTCACTGTCC      1627

CTGAAAGATG  CCCATCAGCC  TGGGATTCGC  TGATGGAAGA  ACTGCAAAGA  GACGCAGCAG      1687

AGAGAAGTCT  GGCTGACAAC  AGATTTAGTA  CTGACCAGCT  GATTTTGTG   GGCAGAAATT      1747

TGAACTTGCT  GCCTGCTGAG  TCCAGTAGTT  GTGCAGGGAG  TGAGATGGCA  GTGTTTAAGT      1807

TTTGATTTGT  AGTTTTTTGT  TTTTGTCTCT  CCCCTCTCCA  GTGTTGGGGA  TTGACCCCAG      1867

GGCAAAGGCA  TTAAGTGTGC  CACTGACCTG  TGCCTCCAAG  TGATGTTCTG  ACAGCTTTC      1927

TGAGGCAATC  AATTGAATTG  AGGTTTTGGG  AGAAGAAACT  GTTGTTCATA  GGCTATTTCT      1987

ATTTTAAAAG  ATGTGAAGAG  AAAAAAAAAA  CAATAAAATT  ATAAAA                    2033
```

( 2 ) INFORMATION FOR SEQ ID NO:10:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Glu Ile His Gly Leu Ala Lys Leu Ile Ala Asp Val Ala Pro Ser
 1               5                  10                  15

Ala Ile Arg Glu Asn Asp Ile Lys Ser Tyr Phe Gly Arg Lys Val Ala
            20                  25                  30

Ile Asp Ala Ser Met Ser Ile Tyr Gln Phe Leu Ile Ala Val Arg Gln
        35                  40                  45

Gly Gly Asp Val Leu Gln Asn Glu Glu Gly Glu Thr Thr Ser Leu Met
50                  55                  60

Gly Met Phe Tyr Arg Thr Met Arg Met Glu Asn Gly Ile Lys Pro Val
65                  70                  75                  80

Tyr Val Phe Asp Gly Lys Pro Pro Gln Leu Lys Ser Gly Glu Leu Ala
                85                  90                  95

Lys Arg Ser Glu Arg Arg Ala Glu Ala Glu Lys Gln Leu Gln Gln Ala
            100                 105                 110

Gln Gln Ala Gly Met Glu Glu Glu Val Glu Lys Phe Thr Lys Arg Leu
        115                 120                 125

Val Lys Val Thr Lys Gln His Asn Asp Glu Cys Lys His Leu Leu Ser
130                 135                 140

Leu Met Gly Ile Pro Tyr Leu Asp Ala Pro Ser Glu Ala Glu Ala Ser
145                 150                 155                 160

Cys Ala Ala Leu Ala Lys Ala Gly Lys Val Tyr Ala Ala Ala Thr Glu
                165                 170                 175

Asp Met Asp Cys Leu Thr Phe Gly Ser Pro Val Leu Met Arg His Leu
            180                 185                 190

Thr Ala Ser Glu Ala Lys Lys Leu Pro Ile Gln Glu Phe His Leu Ser
        195                 200                 205

Arg Val Leu Gln Glu Leu Gly Leu Asn Gln Glu Gln Phe Val Asp Leu
210                 215                 220

Cys Ile Leu Leu Gly Ser Asp Tyr Cys Glu Ser Ile Arg Gly Ile Gly
225                 230                 235                 240

Ala Lys Arg Ala Val Asp Leu Ile Gln Lys His Lys Ser Ile Glu Glu
                245                 250                 255

Ile Val Arg Arg Leu Asp Pro Ser Lys Tyr Pro Val Pro Glu Asn Trp
            260                 265                 270
```

| Leu | His | Lys | Glu | Ala | Gln | Gln | Leu | Phe | Leu | Glu | Pro | Glu | Val | Val | Asp |
|---|---|---|---|---|---|---|---|---|---|---|---|---|---|---|---|
| | | 275 | | | | | 280 | | | | | 285 | | | |

| Pro | Glu | Ser | Val | Glu | Leu | Lys | Trp | Ser | Glu | Pro | Asn | Glu | Glu | Leu |
|---|---|---|---|---|---|---|---|---|---|---|---|---|---|---|
| | | 290 | | | | 295 | | | | | 300 | | | |

| Val | Lys | Phe | Met | Cys | Gly | Glu | Lys | Gln | Phe | Phe | Glu | Glu | Arg | Ile | Arg |
|---|---|---|---|---|---|---|---|---|---|---|---|---|---|---|---|
| 305 | | | | | 310 | | | | | 315 | | | | | 320 |

| Ser | Gly | Val | Lys | Arg | Leu | Ser | Lys | Ser | Arg | Gln | Gly | Ser | Thr | Gln | Gly |
|---|---|---|---|---|---|---|---|---|---|---|---|---|---|---|---|
| | | | | 325 | | | | | 330 | | | | | 335 | |

| Arg | Leu | Asp | Asp | Phe | Phe | Lys | Val | Thr | Gly | Ser | Leu | Ser | Ser | Ala | Lys |
|---|---|---|---|---|---|---|---|---|---|---|---|---|---|---|---|
| | | | 340 | | | | | 345 | | | | | 350 | | |

| Arg | Lys | Glu | Pro | Glu | Pro | Lys | Gly | Pro | Ala | Lys | Lys | Lys | Ala | Lys | Thr |
|---|---|---|---|---|---|---|---|---|---|---|---|---|---|---|---|
| | | | 355 | | | | | 360 | | | | | 365 | | |

| Gly | Gly | Ala | Gly | Lys | Phe | Arg | Arg | Gly | Lys |
|---|---|---|---|---|---|---|---|---|---|
| 370 | | | | | | 375 | | | |

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:11:

GGACTCTGCC TCAAGACGGT AGTCAACGTG      30

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

| Gln | Lys | Arg | Glu | Ser | Ala | Lys | Ser | Thr | Ala | Arg | Ala | Arg |
|---|---|---|---|---|---|---|---|---|---|---|---|---|
| 1 | | | | 5 | | | | | 10 | | | |

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:13:

ATGGGAATTC AAGGCCTGGC CAAACT      26

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:14:

TTTATTTTCC CCTTTTAAAC TTCCCTGC                                                   28

(2) INFORMATION FOR SEQ ID NO:15:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ile Gln Gly Leu Ala Lys Leu Ile Ala Asp Val Ala Pro Ser Ala Ile
1               5                   10                  15

Arg Glu Asn Asp Ile Lys
            20

(2) INFORMATION FOR SEQ ID NO:16:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ser Met Ser Ile Tyr Gln Phe Leu Ile Ala Val Arg Gln Gly Gly Asp
1               5                   10                  15

(2) INFORMATION FOR SEQ ID NO:17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Thr Ser His Leu Met Gly Met Phe Tyr Arg Thr Ile Arg Met Met Glu
1               5                   10                  15

Asn Gly Ile Lys Pro Val
            20

(2) INFORMATION FOR SEQ ID NO:18:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Gly Lys Pro Pro Gln Leu Lys Ser Gly Glu Leu Ala Lys Arg Ser Glu
1               5                   10                  15

Arg Arg Ala Glu Ala Glu Lys Gln
            20

(2) INFORMATION FOR SEQ ID NO:19:

(i) SEQUENCE CHARACTERISTICS:

( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Glu  Gln  Glu  Val  Glu  Lys  Phe  Thr  Lys  Arg  Leu  Val  Lys  Val  Thr  Lys
   1                   5                        10                       15

Gln  His  Asn  Asp
                  20

( 2 ) INFORMATION FOR SEQ ID NO:20:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Leu  Leu  Ser  Leu  Met  Gly  Ile  Pro  Tyr  Leu  Asp  Ala  Pro  Ser  Glu  Ala
   1                   5                        10                       15

Glu  Ala  Ser  Cys  Ala  Ala  Leu  Val  Lys
                  20                       25

( 2 ) INFORMATION FOR SEQ ID NO:21:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Leu  Thr  Phe  Gly  Ser  Pro  Val  Leu  Met  Arg  His  Leu  Thr  Ala  Ser  Glu
   1                   5                        10                       15

Ala  Lys  Lys  Leu  Pro  Ile  Gln
                  20

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Ile  Leu  Gln  Glu  Leu  Gly  Leu  Asn  Gln  Glu  Gln  Phe  Val  Asp  Leu  Cys
   1                   5                        10                       15

Ile  Leu  Leu  Gly  Ser
                  20

( 2 ) INFORMATION FOR SEQ ID NO:23:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear (  i  i  ) MOLECULE TYPE: peptide ( x i ) SEQUENCE DESCRIPTION: SEQ ID NO:23:

Arg Gly Ile Gly Pro Lys Arg Ala Val Asp Leu Ile Gln Lys His Lys
1               5                   10                  15

Ser Ile Glu Glu Ile Val Arg Arg
            20

( 2 ) INFORMATION FOR SEQ ID NO:24:

( i ) SEQUENCE CHARACTERISTICS:
( A ) LENGTH: 20 amino acids
( B ) TYPE: amino acid
( C ) STRANDEDNESS: single
( D ) TOPOLOGY: linear (  i  i  ) MOLECULE TYPE: peptide ( x i ) SEQUENCE DESCRIPTION: SEQ ID NO:24:

Pro Glu Asn Trp Leu His Lys Glu Ala His Gln Leu Phe Leu Glu Pro
1               5                   10                  15

Glu Val Leu Asp
            20

( 2 ) INFORMATION FOR SEQ ID NO:25:

( i ) SEQUENCE CHARACTERISTICS:
( A ) LENGTH: 22 amino acids
( B ) TYPE: amino acid
( C ) STRANDEDNESS: single
( D ) TOPOLOGY: linear (  i  i  ) MOLECULE TYPE: peptide ( x i ) SEQUENCE DESCRIPTION: SEQ ID NO:25:

Trp Ser Glu Pro Asn Glu Glu Leu Ile Lys Phe Met Cys Gly Glu
1               5                   10                  15

Lys Gln Phe Ser Glu Glu
            20

( 2 ) INFORMATION FOR SEQ ID NO:26:

( i ) SEQUENCE CHARACTERISTICS:
( A ) LENGTH: 22 amino acids
( B ) TYPE: amino acid
( C ) STRANDEDNESS: single
( D ) TOPOLOGY: linear (  i  i  ) MOLECULE TYPE: peptide ( x i ) SEQUENCE DESCRIPTION: SEQ ID NO:26:

Ser Lys Ser Arg Gln Gly Ser Thr Gln Gly Arg Leu Asp Asp Phe Phe
1               5                   10                  15

Lys Val Thr Gly Ser Leu
            20

( 2 ) INFORMATION FOR SEQ ID NO:27:

( i ) SEQUENCE CHARACTERISTICS:
( A ) LENGTH: 16 amino acids
( B ) TYPE: amino acid
( C ) STRANDEDNESS: single
( D ) TOPOLOGY: linear (  i  i  ) MOLECULE TYPE: peptide ( x i ) SEQUENCE DESCRIPTION: SEQ ID NO:27:

```
Lys Glu Pro Glu Pro Lys Gly Ser Thr Lys Lys Lys Ala Lys Thr Gly
 1               5                   10                  15
```

(2) INFORMATION FOR SEQ ID NO:28:

(i) SEQUENCE CHARACTERISTICS:
  (A) LENGTH: 1144 base pairs
  (B) TYPE: nucleic acid
  (C) STRANDEDNESS: single
  (D) TOPOLOGY: linear (ii) MOLECULE TYPE: DNA (polynucleotide)

(xi) SEQUENCE DESCRIPTION: SEQ ID NO:28:

```
ATGGAATTC  AAGGCCTGGC  CAAACTAATT  GCTGATGTGG  CCCCCAGTGC  CATCCGGGAG      60
AATGACATCA  AGAGCTACTT  TGGCCGTAAG  GTGGCCATTG  ATGCCTCTAT  GAGCATTTAT     120
CAGTTCCTGA  TTGCTGTTCG  CCAGGGTGGG  GATGTGCTGC  AGAATGAGGA  GGGTGAGACC     180
ACCAGCCACC  TGATGGGCAT  GTTCTACCGC  ACCATTCGCA  TGATGGAGAA  CGGCATCAAG     240
CCCGTGTATG  TCTTTGATGG  CAAGCCGCCA  CAGCTCAAGT  CAGGCGAGCT  GGCCAAACGC     300
AGTGAGCGGC  GGGCTGAGGC  AGAGAAGCAG  CTGCAGCAGG  CTCAGGCTGC  TGGGGCCGAG     360
CAGGAGGTGG  AAAAATTCAC  TAAGCGGCTG  GTGAAGGTCA  CTAAGCAGCA  CAATGATGAG     420
TGCAAACATC  TGCTGAGCCT  CATGGGCATC  CCTTATCTTG  ATGCACCCAG  TGAGGCAGAG     480
GCCAGCTGTG  CTGCCCTGGT  GAAGGCTGGC  AAAGTCTATG  CTGCGGCTAC  CGAGGACATG     540
GACTGCCTCA  CCTTCGGCAG  CCCTGTGCTA  ATGCGACACC  TGACTGCCAG  TGAAGCCAAA     600
AAGCTGCCAA  TCCAGGAATT  CCACCTGAGC  CGGATTCTGC  AGGAGCTGGG  CCTGAACCAG     660
GAACAGTTTG  TGGATCTGTG  CATCCTGCTA  GGCAGTGACT  ACTGTGAGAG  TATCCGGGGT     720
ATTGGGCCCA  AGCGGGCTGT  GGACCTCATC  CAGAAGCACA  AGAGCATCGA  GGAGATCGTG     780
CGGCGACTTG  ACCCCAACAA  GTACCCTGTG  CCAGAAAATT  GGCTCCACAA  GGAGGCTCAC     840
CAGCTCTTCT  TGGAACCTGA  GGTGCTGGAC  CCAGAGTCTG  TGGAGCTGAA  GTGGAGCGAG     900
CCAAATGAAG  AAGAGCTGAT  CAAGTTCATG  TGTGGTGAAA  AGCAGTTCTC  TGAGGAGCGA     960
ATCCGCAGTG  GGGTCAAGAG  GCTGAGTAAG  AGCCGCCAAG  GCAGCACCCA  GGGCCGCCTG    1020
GATGATTTCT  TCAAGGTGAC  CGGCTCACTC  TCTTCAGCTA  AGCGCAAGGA  GCCAGAACCC    1080
AAGGGATCCA  CTAAGAAGAA  GGCAAAGACT  GGGGCAGCAG  GGAAGTTTAA  AAGGGGAAAA    1140
TAAA                                                                     1144
```

(2) INFORMATION FOR SEQ ID NO:29:

(i) SEQUENCE CHARACTERISTICS:
  (A) LENGTH: 45 base pairs
  (B) TYPE: nucleic acid
  (C) STRANDEDNESS: single
  (D) TOPOLOGY: linear (ii) MOLECULE TYPE: DNA (oligonucleotide)

(xi) SEQUENCE DESCRIPTION: SEQ ID NO:29:

```
TGGGAATTCA  AGGCCTGGCC  AAACTAATTG  CTGATGTGGC  CCCCA                      45
```

(2) INFORMATION FOR SEQ ID NO:30:

(i) SEQUENCE CHARACTERISTICS:
  (A) LENGTH: 35 base pairs
  (B) TYPE: nucleic acid
  (C) STRANDEDNESS: single
  (D) TOPOLOGY: linear ( i i ) MOLECULE TYPE: DNA (oligonucleotide)

( x i ) SEQUENCE DESCRIPTION: SEQ ID NO:30:

TGACATCAAG AGCTACTTTG GCCGTAAGGT GGCCA 35

( 2 ) INFORMATION FOR SEQ ID NO:31:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:31:

TGCCTCTATG AGCATTTATC AGTTCCTGAT TGCTGTT 37

( 2 ) INFORMATION FOR SEQ ID NO:32:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:32:

GGATGTGCTG CAGAATGAGG AGGGTGAGAC CAC 33

( 2 ) INFORMATION FOR SEQ ID NO:33:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:33:

TGGGCATGTT CTACCGCACC ATTCGCATGA TGGAGAACG 39

( 2 ) INFORMATION FOR SEQ ID NO:34:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:34:

CTTTGATGGC AAGCCGCCAC AGCTCAAGTC AGGCGAGCTG G 41

( 2 ) INFORMATION FOR SEQ ID NO:35:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:35:

AGCAGCTGCA GCAGGCTCAG GCTGCTGGGG CC 32

(2) INFORMATION FOR SEQ ID NO:36:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:36:

AATTCACTAA GCGGCTGGTG AAGGTCACTA AGCAG 35

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:37:

ATGATGAGTG CAAACATCTG CTGAGCCTCA TG 32

(2) INFORMATION FOR SEQ ID NO:38:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:38:

ATCCCTTATC TTGATGCACC CAGTGAGGCA GAGGCCA 37

(2) INFORMATION FOR SEQ ID NO:39:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:39:

GCCCTGGTGA AGGCTGGCAA AGTCTATGCT GCGGCTACCG AGGA 44

(2) INFORMATION FOR SEQ ID NO:40:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:40:

CTTCGGCAGC CCTGTGCTAA TGCGACACCT GAC 33

(2) INFORMATION FOR SEQ ID NO:41:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( i i ) MOLECULE TYPE: DNA (oligonucleotide)

( x i ) SEQUENCE DESCRIPTION: SEQ ID NO:41:

CAGGAATTCC ACCTGAGCCG GATTCTGCAG GAGCTG 36

( 2 ) INFORMATION FOR SEQ ID NO:42:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:42:

CCTGAACCAG GAACAGTTTG TGGATCTGTG CATCCT 36

( 2 ) INFORMATION FOR SEQ ID NO:43:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:43:

AGGCAGTGAC TACTGTGAGA GTATCCGGGG TATTGGGCCC A 41

( 2 ) INFORMATION FOR SEQ ID NO:44:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:44:

GGCTGTGGAC CTCATCCAGA AGCACAAGAG CATCGAGGA 39

( 2 ) INFORMATION FOR SEQ ID NO:45:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:45:

CAAGTACCCT GTGCCAGAAA ATTGGCTCCA CAAGGAGGCT 40

( 2 ) INFORMATION FOR SEQ ID NO:46:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:46:

CTGAGGTGCT GGACCCAGAG TCTGTGGAGC TGAAGTGG    38

( 2 ) INFORMATION FOR SEQ ID NO:47:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:47:

GATCAAGTTC ATGTGTGGTG AAAAGCAGTT CTCTGAGGAG C    41

( 2 ) INFORMATION FOR SEQ ID NO:48:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:48:

ATCCGCAGTG GGGTCAAGAG GCTGAGTAAG AGCCGCCA    38

( 2 ) INFORMATION FOR SEQ ID NO:49:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:49:

GCAGCACCCA GGGCCGCCTG GATGATTTCT TC    32

( 2 ) INFORMATION FOR SEQ ID NO:50:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:50:

CGGCTCACTC TCTTCAGCTA AGCGCAAGGA GCCA    34

( 2 ) INFORMATION FOR SEQ ID NO:51:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:51:

CCCAAGGGAT CCACTAAGAA GAAGGCAAAG ACTGGGGCAG C 41

( 2 ) INFORMATION FOR SEQ ID NO:52:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:52:

CACGTTGACT GAATC 15

( 2 ) INFORMATION FOR SEQ ID NO:53:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:53:

ACCGTCTTGA GGCAGAGT 18

( 2 ) INFORMATION FOR SEQ ID NO:54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:54:

GGACTCTGCC TCAAGACGGT AGTCAACGTG 30

( 2 ) INFORMATION FOR SEQ ID NO:55:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:55:

CATGTCAAGC AGTCCTAACT TTGAGGCAGA GTCC 34

( 2 ) INFORMATION FOR SEQ ID NO:56:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:56:

CACGTTGACT ACCGTC 16

( 2 ) INFORMATION FOR SEQ ID NO:57:

( i ) SEQUENCE CHARACTERISTICS:
　　　　( A ) LENGTH: 25 base pairs
　　　　( B ) TYPE: nucleic acid
　　　　( C ) STRANDEDNESS: single
　　　　( D ) TOPOLOGY: linear ( i i ) MOLECULE TYPE: DNA (oligonucleotide)

( x i ) SEQUENCE DESCRIPTION: SEQ ID NO:57:

GTAGGAGATG TCCCTTGATG AATTC　　　　　　　　　　　　　　　　　　　　　25

( 2 ) INFORMATION FOR SEQ ID NO:58:

( i ) SEQUENCE CHARACTERISTICS:
　　　　( A ) LENGTH: 16 base pairs
　　　　( B ) TYPE: nucleic acid
　　　　( C ) STRANDEDNESS: single
　　　　( D ) TOPOLOGY: linear ( i i ) MOLECULE TYPE: DNA (oligonucleotide)

( x i ) SEQUENCE DESCRIPTION: SEQ ID NO:58:

CAGCAACGCA AGCTTG　　　　　　　　　　　　　　　　　　　　　　　　　16

( 2 ) INFORMATION FOR SEQ ID NO:59:

( i ) SEQUENCE CHARACTERISTICS:
　　　　( A ) LENGTH: 19 base pairs
　　　　( B ) TYPE: nucleic acid
　　　　( C ) STRANDEDNESS: single
　　　　( D ) TOPOLOGY: linear ( i i ) MOLECULE TYPE: DNA (oligonucleotide)

( x i ) SEQUENCE DESCRIPTION: SEQ ID NO:59:

TAGCAGGCTG CAGGTCGAC　　　　　　　　　　　　　　　　　　　　　　　19

( 2 ) INFORMATION FOR SEQ ID NO:60:

( i ) SEQUENCE CHARACTERISTICS:
　　　　( A ) LENGTH: 30 base pairs
　　　　( B ) TYPE: nucleic acid
　　　　( C ) STRANDEDNESS: single
　　　　( D ) TOPOLOGY: linear ( i i ) MOLECULE TYPE: DNA (oligonucleotide)

( x i ) SEQUENCE DESCRIPTION: SEQ ID NO:60:

GTCGACCTGC AGCCCAAGCT TGCGTTGCTG　　　　　　　　　　　　　　　　　30

( 2 ) INFORMATION FOR SEQ ID NO:61:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: DNA (oligonucleotide)

( x i ) SEQUENCE DESCRIPTION: SEQ ID NO:61:

AGGCTGCAGG TCGAC　　　　　　　　　　　　　　　　　　　　　　　　　15

( 2 ) INFORMATION FOR SEQ ID NO:62:

( i ) SEQUENCE CHARACTERISTICS:
　　　　( A ) LENGTH: 33 base pairs
　　　　( B ) TYPE: nucleic acid
　　　　( C ) STRANDEDNESS: single
　　　　( D ) TOPOLOGY: linear ( i i ) MOLECULE TYPE: DNA (oligonucleotide)

( x i ) SEQUENCE DESCRIPTION: SEQ ID NO:62:

ATGTGGAAAA TCTCTAGCAG GCTGCAGGTC GAC 33

( 2 ) INFORMATION FOR SEQ ID NO:63:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:63:

TGCTAGAGAT TTTCCACAT 19

We claim:

1. An isolated polynucleotide encoding a Fen-1 polypeptide as shown in SEQ ID NO 1 or SEQ ID NO 3, or a fragment of said polypeptide having flap endonucleolytic cleavage activity.

2. An isolated polynucleotide, wherein said polynucleotide comprises a nucleotide sequence selected from the group of sequences consisting of SEQ. ID. NOS: 29–51.

3. An isolated polynucleotide of claim 2, wherein said polynucleotide comprises the sequence of SEQ. ID. NO:28.

4. A host cell comprising the polynucleotide of claim 1.

5. A non-mammalian host cell comprising a mammalian FEN-1 polypeptide of claim 1.

6. The polynucleotide of claim 1 that is full-length.

* * * * *